(12) United States Patent
Osterkamp et al.

(10) Patent No.: US 10,961,199 B2
(45) Date of Patent: Mar. 30, 2021

(54) NEUROTENSIN RECEPTOR LIGANDS

(71) Applicant: 3B Pharmaceuticals GmbH, Berlin (DE)

(72) Inventors: Frank Osterkamp, Berlin (DE); Christiane Smerling, Berlin (DE); Ulrich Reineke, Berlin (DE); Christian Haase, Berlin (DE); Jan Ungewiß, Berlin (DE)

(73) Assignee: 3B PHARMACEUTICALS GMBH, Berlin (DE)

( * ) Notice: Subject to any disclaimer, the term of this patent is extended or adjusted under 35 U.S.C. 154(b) by 0 days.

(21) Appl. No.: 14/650,437

(22) PCT Filed: Dec. 6, 2013

(86) PCT No.: PCT/EP2013/003700
§ 371 (c)(1),
(2) Date: Jun. 8, 2015

(87) PCT Pub. No.: WO2014/086499
PCT Pub. Date: Jun. 12, 2014

(65) Prior Publication Data
US 2015/0299133 A1    Oct. 22, 2015

(30) Foreign Application Priority Data

Dec. 7, 2012 (EP) .................................. 12008208

(51) Int. Cl.
*A61K 51/00* (2006.01)
*A61M 36/14* (2006.01)
(Continued)

(52) U.S. Cl.
CPC ........ *C07D 231/14* (2013.01); *A61K 51/0482* (2013.01); *C07D 403/12* (2013.01)

(58) Field of Classification Search
CPC ............... C07D 231/14; C07D 403/12; A61K 51/0482
(Continued)

(56) References Cited

U.S. PATENT DOCUMENTS 4,110,321 A    8/1978 Folkers
4,425,269 A    1/1984 Christy et al.
(Continued)

FOREIGN PATENT DOCUMENTS

CA    2220827        10/1996
EP    0477049 A1     3/1992
(Continued)

OTHER PUBLICATIONS

Alshoukr et al. Bioconjugate Chem. 2011, 22, 1374-1385.*
Gully et al. JPET 1997, 280, 802-812.*
Andre et al. Chem. Commun. 1998, 1301-1302.*
Holland et al. J. Nucl. Med. 2010, 51, 1293-1300.*
Keliher et al. Bioconj. Chem. 2011, 22, 2383-2389.*
Lipinski et al. Adv. Drug Del. Rev. 46, 2001, 3-16.*
Maschauer et al. ACS Med. Chem. Lett. 2010, 1, 224-228.*
(Continued)

*Primary Examiner* — Michael G. Hartley
*Assistant Examiner* — Sean R Donohue
(74) *Attorney, Agent, or Firm* — DLA Piper LLP US

(57) ABSTRACT

The present invention is related to a compound of formula (I) wherein $R^1$ is selected from the group consisting of hydrogen, methyl and cyclopropylmethyl; AA-COOH is an amino acid selected from the group consisting of 2-amino-2-adamantane carboxylic acid, cyclohexylglycine and 9-amino-bicyclo[3.3.1]nonane-9-carboxylic acid; $R^2$ is selected from the group consisting of $(C_1-C_6)$alkyl, $(C_3-C_8)$ cycloalkyl, $(C_3-C_5)$cycloalkylmethyl, halogen, nitro and trifluoromethyl; ALK is $(C_2-C_5)$alkylidene; $R^3$, $R^4$ and $R^5$ are each and independently selected from the group consisting of hydrogen and $(C_1-C_4)$alkyl under the proviso that one of $R^3$, $R^4$ and $R^5$ is of the formula (II) wherein ALK' is $(C_2-C_5)$alkylidene; $R^6$ is selected from the group consisting of hydrogen and $(C_1-C_4)$alkyl; and $R^7$ is selected from the group consisting of H and an Effector moiety; or a pharmacologically acceptable salt, solvate or hydrate thereof.

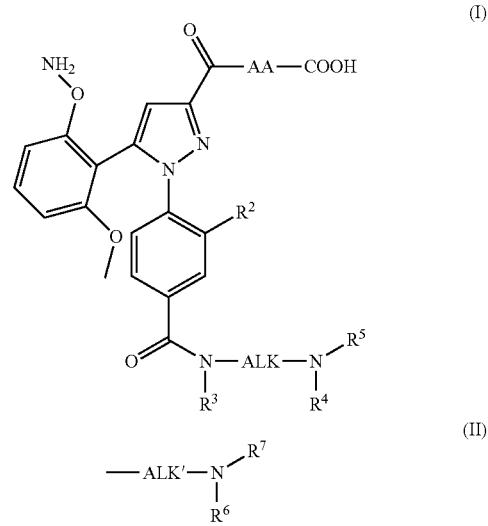

26 Claims, 9 Drawing Sheets
Specification includes a Sequence Listing.

(51) Int. Cl.
 *C07D 231/14* (2006.01)
 *C07D 403/12* (2006.01)
 *A61K 51/04* (2006.01)

(58) Field of Classification Search
 USPC ........................................................ 424/1.65
 See application file for complete search history.

(56) References Cited

U.S. PATENT DOCUMENTS

| | | | |
|---|---|---|---|
| 4,439,359 A | 3/1984 | Holley et al. | |
| 4,885,363 A | 12/1989 | Tweedle et al. | |
| 5,021,556 A | 6/1991 | Srinivasan | |
| 5,075,099 A | 12/1991 | Srinivasan et al. | |
| 5,364,613 A | 11/1994 | Sieving et al. | |
| 5,367,080 A | 11/1994 | Toner et al. | |
| 5,407,916 A | 4/1995 | Wise et al. | |
| 5,420,141 A | 5/1995 | Boigegrain et al. | |
| 5,607,958 A | 3/1997 | Boigegrain et al. | |
| 5,616,592 A | 4/1997 | Boigegrain et al. | |
| 5,635,526 A | 6/1997 | Boigegrain et al. | |
| 5,720,934 A | 2/1998 | Dean et al. | |
| 5,723,483 A | 3/1998 | Labeeuw et al. | |
| 5,744,491 A | 4/1998 | Boigegrain et al. | |
| 5,744,493 A | 4/1998 | Boigegrain et al. | |
| 5,886,142 A | 3/1999 | Thakur et al. | |
| 5,925,661 A | 7/1999 | Labeeuw et al. | |
| 5,936,123 A | 8/1999 | Labeeuw et al. | |
| 5,939,449 A | 8/1999 | Labeeuw et al. | |
| 5,965,579 A | 10/1999 | Labeeuw et al. | |
| 6,172,239 B1 | 1/2001 | Labeeuw et al. | |
| 2005/0112065 A1* | 5/2005 | Drummond | A61K 9/1272 424/9.321 |
| 2006/0062729 A1 | 3/2006 | Carraway | |
| 2010/0256055 A1 | 10/2010 | Castaigne et al. | |
| 2011/0263819 A1* | 10/2011 | Olma | C07D 207/26 530/328 |
| 2011/0305633 A1* | 12/2011 | Forgez | C12Q 1/6886 424/1.69 |

FOREIGN PATENT DOCUMENTS

| | | |
|---|---|---|
| EP | 0606804 A2 | 7/1994 |
| WO | 1995022341 A1 | 8/1995 |
| WO | 96/32382 | 10/1996 |
| WO | 1996031531 A2 | 10/1996 |
| WO | 1997004311 A2 | 2/1997 |
| WO | 1998001472 A1 | 1/1998 |
| WO | 98/33531 A1 | 8/1998 |
| WO | 1999052539 A1 | 10/1999 |
| WO | 2000078796 A2 | 12/2000 |
| WO | 2009109332 A1 | 9/2009 |
| WO | 2011006985 A1 | 1/2011 |
| WO | 2011/156557 A2 | 12/2011 |

OTHER PUBLICATIONS

Cachin et al. J. Clin. Oncol. 2006, 3026-3031.*
International Search Report and Written Opinion, PCT/EP2013/003700, dated Feb. 4, 2014, 13 pages.
Achilefu et al., Novel Bioactive and Stable Neurotensin Peptide Analogues Capable of Delivering Radiopharmaceuticals and Molecular Beacons to Tumors, J. Med. Chem., 2003, 46: 3403-3411.
Alifano et al., Neurotensin Receptor 1 Determines the Outcome of Non-Small Cell Lung Cancer, Clin. Cancer Res., 2010, 16:4401-4410 (and figure) (11 pages).
Alifano et al., Neurotensin expression and outcome of malignant pleural mesothelioma, Biochimie, 2010, 92:164-170.
Almeida et al., Differential expression of new splice variants of the neurotensin receptor 1 gene in human prostate cancer cell lines, Peptides, 2010, 31:242-247.
Alshoukr et al., Novel Neurotensin Analogues for Radioisotope Targeting to Neurotensin Receptor-Positive Tumors, Bioconjugate Chem., 2009, 20:1602-1610.

Alshoukr et al., Novel DOTA-Neurotensin Analogues for 111In Scintigraphy and 68Ga PET Imaging of Neurotensin Receptor-Positive Tumors, Bioconjugate Chem., 2011, 22:1374-1385.
Amorino et al., Neurotensin stimulates mitogenesis of prostate cancer cells through a novel c-Src/Stat5b pathway, Oncogene, 2007, 26:745-756.
Babich et al., Technetium-.99m-Labeled Hydrazino Nicotinamide Derivatized Chemotactic Peptide Analogs for Imaging Focal Sites of Bacterial Infection, J. Nucl. Med., 1993, 34: 1964-1974.
Babich et al., Effect of "Co-ligand" on the Biodistribution of 99mTc-labeled Hydrazino Nicotinic Acid Derivatized Chemotactic Peptides, Nucl. Med. Biol., 1995, 22:25-30.
Banerjee et al., New directions in the coordination chemistry of 99mTc: a reflection on technetium core structures and a strategy for new chelate design, Nucl. Med. Biol., 2005, 32:1-20.
Bergmann et al., Biodistribution and catabolism of 18F-labeled neurotensin(8-13) analogs, Nucl. Med. Biol., 2002, 29:61-72.
Blauenstein et al., Improving the Tumor Uptake of 99mTc-Labeled Neuropeptides Using Stabilized Peptide Analogues, Cancer Biother. Radiopharm., 2004, 19:181-188.
Bodei et al., Receptor Radionuclide Therapy of Tumors: A Road from Basic Research to Clinical Applications, J. Nucl. Med., 2006, 47:375-377.
Bossard et al., Over-expression of neurotensin high-affinity receptor 1 (NTS1) in relation with its ligand neurotensin (NT) and nuclear ß-catenin in inflammatory bowel disease-related oncogenesis, Peptides, 2007, 28:2030-2035.
Boudin et al., Cellular distribution of neurotensin receptors in rat brain: immunohistochemical study using an antipiptide antibody against the cloned high affinity receptor, J. Comp. Neurol., 1996, 373:76-89.
Brechbiel et al., Backbone-Substituted DTPA Ligands for 90Y Radioimmunotherapy, Bioconj. Chem., 1991, 2:187-194.
Bruehlmeier et al., Stabilization of neurotensin analogues: effect on peptide catabolism, biodistribution and tumor binding, Nucl. Med. Biol., 2002, 29:321-327.
Buchegger et al., Radiolabeled Neurotensin Analog, 99mTc-NT-XI, Evaluated in Ductal Pancreatic Adenocarcinoma Patients, J. Nucl. Med., 2003, 44:1649-1654.
Bugni et al., The neurotensin receptor-1 promotes tumor development in a sporadic but not an inflammation-associated mouse model of colon cancer, Int. J. Cancer, 2012, 130:1798-1805.
Carraway et al., The Isolation of a new hypotensive peptide, neurotensin, from bovine hypothalami, J. Biol. Chem., 1973, 248:6854-6861.
Cescato et al., Internalization of sst2, sst3, and sst5 Receptors: Effects of Somatostatin Agonists and Antagonists, J. Nucl. Med., 2006, 47:502-511.
Chao et al., Gastrointestinal Hormone Receptors in Primary Human Colorectal Carcinomas, J. Surg. Res., 2005, 129:313-321.
De Visser et al., Stabilised 111In-labelled DTPA- and DOTA-conjugated neurotensin analogues for imaging and therapy of exocrine pancreatic cancer, Eur. J. Nucl. Med. Mol. Imaging, 2003, 30:1134-1139.
Doulias et al., Endosomal and lysosomal effects of desferrioxamine: protection of hela cells from hydrogen peroxide-induced dna damage and induction of cell-cycle arrest, Free Radic. Biol. Med., 2003, 35:719-728.
Dupouy et al., The Neurotensin Receptor-1 Pathway Contributes to Human Ductal Breast Cancer Progression, PLoS One, 2009, 4:e4223;1-7.
Ehlers et al., Gut Peptide Receptor Expression in Human Pancreatic Cancers, Ann. Surg., 2000, 231:838-848.
Fani et al., Unexpected Sensitivity of sst2 Antagonists to N-Terminal Radiometal Modifications, J. Nucl. Med., 2012, 53:1481-1489.
Friry et at., Production of recombinant large proneurotensin/neuromedin N-derived peptides and characterization of their binding and biological activity, Biochem. Biophys. Res. Commun., 2002, 290:1161-1168.
Fritzberg et al., Targeted Proteins for Diagnostic Imaging: Does Chemistry Make a Difference, J. Nucl. Med., 1992, 33:394-397.

(56) References Cited

OTHER PUBLICATIONS

Gabriel et al., [99mTc] Demotensin VI: Biodistribution and Initial Clinical Results in Tumor Patients of a Pilot/Phase I Study, Cancer Biother. Radiopharm., 2011, 26:557-563.
Garcia-Garayoa et al., In vitro and in vivo evaluation of new radiolabeled neurotensin(8-13) analogues with high affinity for NT1 receptors, Nucl. Med. Biol., 2001, 28:75-84.
Garcia-Garayoa et al., Preclinical Evaluation of a New, Stabilized Neurotensin(8-13) Pseudopeptide Radiolabeled with 99mTc, J. Nucl. Med., 2002, 43:374-383.
Garcia-Garayoa et al., Double-stabilized neurotensin analogues as potential radiopharmaceuticals for NTR-positive tumors, Nucl. Med. Biol., 2006, 33:495-503.
Garcia-Garayoa et al., A stable neurotensin-based radiopharmaceutical for targeted imaging and therapy of neurotensin receptor-positive tumours, Eur. J. Nucl. Med. Mol. Imaging, 2009, 36:37-47.
Ginj et al., Radiolabeled somatostatin receptor antagonists are preferable to agonists for in vivo peptide receptor targeting of tumors, Proc. Natl. Acad. Sci. USA, 2006, 103:16436-16441.
Gromova et al., Neurotensin Receptor 1 Is Expressed in Gastrointestinal Stromal Tumors but Not in Interstitial Cells of Cajal, PLoS One, 2011, 6:e14710;1-10.
Gui et al., Increased neurotensin receptor-1 expression during progression of colonic adenocarcinoma, Peptides, 2008, 29:1609-1615.
Haase et al., Neurotensin receptors in adeno- and squamous cell carcinoma, Anitcancer Res., 2006, 26:3527-3533.
Iwase et al., Inhibition of Neurotensin-Induced Pancreatic Carcinoma Growth by a Nonpeptide Neurotensin Receptor Antagonist, SR48692, Cancer, 1997, 79:1787-1793.
Janssen et al., Five stabilized 111In-labeled neurotensin analogs in nude mice bearing HT29 tumors, Cancer Biother. Radiopharm., 2007, 22:374-381.
Koenig et al., Endocytosis and recycling of G protein-coupled receptors, Trends Pharmacol. Sci., 1997, 18:276-287.
Li et al., Development of an in vitro model for assessing the in vivo stability of lanthanide chelates, Nucl. Med. Biol., 2001, 28:145-154.
Eisenwiener et al., NODAGATOC, a new chelator-coupled somatostatin analogue labeled with [67/68Ga] and [111In] for SPECT, PET, and targeted therapeutic applications of somatostatin receptor (hsst2) expressing tumors, Bioconj. Chem., 2002, 13:530-541.
Maes et al., Novel 99mTc-Labeled Neurotensin Analogues with Optimized Biodistribution Properties, J. Med. Chem., 2006, 49:1833-1836.
Maina et al., [99mTc] Demotensin 5 and 6 in the NTS1-R-targeted imaging of tumours: synthesis and preclinical results, Eur. J. Nucl. Med. Mol. Imaging, 2007, 34:1804-1814.
Martin et al., Neurotensin receptor-1 and-3 complex modulates the cellular signaling of neurotensin in the Ht29 cell line, Gastroenterology, 2002, 123:1135-1143.
Mazella et al., Structure, Functional Expression, and Cerebral Localization of the Levocabastine-Sensitive Neurotensin/Neuromedin N Receptor from Mouse Brain, J. Neurosci., 1996, 16:5613-5620.
Mazella, Sortilin/neurotensin receptor-3: a new tool to investigate neurotensin signaling and cellular trafficking?, Cell Signal., 2001, 13:1-6.
Moody, SR48692 is a neurotensin receptor antagonist which inhibits the growth of small cell lung cancer cells, Panminerva Med., 2006, 48:19-26.
Moody et al., SR48692 is a neurotensin receptor antagonist which inhibits the growth of small cell lung cancer cells, Peptides, 2001, 22:109-115.
Nock et al., CCK-2/Gastrin Receptor—Targeted Tumor Imaging with 99mTc-Labeled Minigastrin Analogs, J. Nucl. Med., 2005, 46:1727-1736.
Nock et al., Toward Stable N4-Modified Neurotensins for NTS1-Receptor-Targeted Tumor Imaging with 99mTc, J. Med. Chem., 2006, 49:4767-4776.

Ocejo-Garcia et al., Use of RT-PCR to detect co-expression of neuropeptides and their receptors in lung cancer, Lung Cancer, 2001, 33:1-9.
Palmedo et al., Breast cancer imaging with PET and SPECT agents: an in vivo comparison, Nucl. Med. Biol., 2002, 29:809-815.
Pelaprat, Interactions between neurotensin receptors and G proteins, Peptides, 2006, 27:2476-2487.
Ramez et al., Functional Characterization of Neurotensin Receptors in Human Cutaneous T Cell Lymphoma Malignant Lymphocytes, J. Invest. Dermatol., 2001, 117:687-693.
Rettenbacher et al., Localization and characterization of neuropeptide receptors in human colon, Naunyn-Schmiedeberg's Arch. Pharmacol., 2001, 364:291-304.
Reubi et al., Neurotensin receptors: a new marker for human ductal pancreatic adenocarcinoma, Gut, 1998, 42:546-550.
Reubi et al., Neurotensin receptors in human neoplasms: high incidence in Ewing's sarcomas, Int. J. Cancer, 1999, 82:213-218.
Rodriguez et al., Neurotensin and neurotensin receptor 1 expression in human myometrium and uterine leiomyomas, Biol. Reprod., 2010, 83:641-647 (16 pages).
Rodriguez et al., Comparative Analysis of the ERa/ERb Ratio and Neurotensin and its High-affinity Receptor in Myometrium, Uterine Leiomyoma, Atypical Leiomyoma, and Leiomyosarcoma, Int. J. Gynecol. Pathol., 2011, 30:354-363.
Schwartz et al., Preparation of Hydrazino-Modified Proteins and Their Use for the Synthesis of 99mTc-Protein Conjugates, Bioconj. Chem., 1991, 2:333-336.
Shimizu et al., Identification of a novel therapeutic target for head and neck squamous cell carcinomas: A role for the neurotensin-neurotensin receptor 1 oncogenic signaling pathway, Int. J. Cancer, 2008, 123:1816-1823.
Souaze et al., Expression of Neurotensin and NT1 Receptor in Human Breast Cancer: A Potential Role in Tumor Progression, Cancer Res., 2006, 66:6243-6249.
Swift et al., Altered expression of neurotensin receptors is associated with the differentiation state of prostate cancer, Cancer Res., 2010, 70:347-356 (16 pages).
Tanaka et at., Structure and functional expression of the cloned rat neurotensin receptor, Neuron, 1990, 4:847-854.
Taylor et al., Prostate Cancer Targeting Motifs: Expression of $\alpha v\beta 3$, Neurotensin Receptor 1, Prostate Specific Membrane Antigen, and Prostate Stem Cell Antigen in Human Prostate Cancer Cell Lines and Xenografts, The Prostate, 2012, 72:523-532.
Valerie et al., Inhibition of Neurotensin Receptor 1 Selectively Sensitizes Prostate Cancer to Ionizing Radiation, Cancer Res., 2011, 71:6817-6826.
Vincent et at., Neurotensin and neurotensin receptors, Trends Pharmacol. Sci., 1999, 20:302-309.
Wadas et al., Coordinating Radiometals of Copper, Gallium, Indium, Yttrium, and Zirconium for PET and SPECT Imaging of Disease, Chem. Rev., 2010, 110:2858-2902.
Wang et al., Pancreatic cancer bears overexpression of neurotensin and neurotensin receptor subtype-1 and SR 48692 counteracts neurotensin induced cell proliferation in human pancreatic ductal carcinoma cell line PANC-1, Neuropeptides, 2011, 45:151-156.
Wang et al., Neurotensin Receptor-1 mRNA Analysis in Normal Pancreas and Pancreatic Disease, Clin. Cancer Res. 2000, 6:566-571.
Burian et al., "Novel neurotensin-based radio-tracers for imaging and therapy of ductal pancreatic adenocarcinoma", Eur J Nuclear Medicine Molecular Imaging Oct. 2012; 39(Suppl 2).
Cáceda et al., "The role of endogenous neurotensin in psychostimulant-induced disruption of prepulse inhibition and locomotion," Schizophrenia Research. Apr. 2012;136(1-3):88-95. doi: 10.1016/j.schres.2011.10.013. Epub Nov. 21, 2011.
Michaud et al., "Effects of neurotensin receptor antagonists on the firing rate of rat ventral pallidum neurons," Neuropharmacoloby. Neuroreport. May 15, 2000;11(7)1437-41.
Sarau et al., "Nonpeptide tachykinin receptor antagonists: I. Pharmacological and pharmacokinetic characterization of SB 223412, a novel, potent and selective neurokinin-3 receptor antagonist," J Pharmacol Exp Ther. Jun. 1997; 281 (3), 1303-1311.

(56) References Cited

OTHER PUBLICATIONS

Schioth et al., "Characterization of the binding of MSH-B, HB-228, GHRP-6 and 153N-6 to the human melanocortin receptor subtypes," Neuropeptides. Dec. 1997; 31(6), 565-71.
Shen et al., "Molecular cloning and expression of a 5-hydroxytryptamine7 serotonin receptor subtype," J Biol Chem. Aug. 25, 1993; 268(24), 18200-18204.
Simonin et al., "The human delta-opioid receptor: genomic organization, cDNA cloning, functional expression, and distribution in human brain," Mol Pharmacol. Dec. 1994; 46(6), 1015-21.
Smit et al., "Regulation of the human histamine H1 receptor stably expressed in Chinese hamster ovary cells," Br. J. Pharmacol. Mar. 1996;117(6), 1071-1080.
Sorensen et al., "Rat brain dendrotoxin receptors associated with voltage-gated potassium channels: dendrotoxin binding and receptor solubilization," Mol Pharmacol. Nov. 1989; 36(5), 689-98.
Speth et al., "Benzodiazepine receptors: temperature dependence of [3H]flunitrazepam binding," Life Sci. Jan. 22, 1979; 24(4), 351-7.
Tahara et al., "Pharmacological characterization of the human vasopressin receptor subtypes stably expressed in Chinese hamster ovary cells," Br. J. Pharmacol. Dec. 1998; 125(7), 1463-70.
Tatsumi et al., "Pharmacological profile of neuroleptics at human monoamine transporters," Eur J Pharmacol. Mar. 5, 1999; 368(2-3), 277-83.
Townsend-Nicholson et al., "A threonine residue in the seventh transmembrane domain of the human A1 adenosine receptor mediates specific agonist binding," J Biol Chem. Jan. 28, 1994; 269(4), 2373-6.
Tsuji et al., "Inhibitory effects of quinolone antibacterial agents on gamma-aminobutyric acid binding to receptor sites in rat brain membranes," Antimicrob Agents Chemother. Feb. 1988; 32(2), 190-4.
Uhlen et al., "Rat spinal cord alpha 2-adrenoceptors are of the alpha 2A-subtype: comparison with alpha 2A- and alpha 2B-adrenoceptors in rat spleen, cerebral cortex and kidney using 3H-RX821002 ligand binding," Pharmacol Toxicol. Nov. 1991; 69(5), 341-50.
Visser et al., "Stabilised 111In-labelled DTPA- and DOTA-conjugated neurotensin analogues for imaging and therapy of exocrine pancreatic cancer," Eur J Nucl Med Mol Imaging. Aug. 2003; 30(8), 1134-9. Epub May 24, 2003.
Vita et al., "Cloning and expression of a complementary DNA encoding a high affinity human neurotensin receptor," FEBS Lett. Feb. 8, 1993; 317(1-2), 139-42.
Wang et al., "Human mu opiate receptor. cDNA and genomic clones, pharmacologic characterization and chromosomal assignment," FEBS Lett. Jan. 31, 1994; 338(2), 217-22.
White et al., "Identification of a potent, selective non-peptide CXCR2 antagonist that inhibits interleukin-8-induced neutrophil migration," J Biol Chem. Apr. 24, 1998; 273(17), 10095-8.
Wieland et al., "Subtype selectivity and antagonistic profile of the nonpeptide Y1 receptor antagonist BIBP 3226," J Pharmacol Exp Ther. Oct. 1995; 275(1), 143-9.
Witt-Enderby et al., "Characterization and regulation of the human ML1A melatonin receptor stably expressed in Chinese hamster ovary cells," Mol Pharmacol. Jul. 1996; 50(1), 166-74.
Zhou et al., "Cloning and expression of human and rat D1 dopamine receptors," Nature. Sep. 6, 1990; 347(6288), 76-80.
Choi et al., "The human serotonin 5-HT2B receptor: Pharmacological link between 5-HT2 and 5-HT1D receptors," FEBS Lett., Oct. 3, 1994; 352(3), 393-399.
Couvineau et al., "Molecular identification and structural requirement of vasoactive intestinal peptide (VIP) receptors in the human colon adenocarcinoma cell line, HT-29," Biochem J., Oct. 1, 1985; 231(1): 139-143.
Dörje et al., "Antagonist binding profiles of five cloned human muscarinic receptor subtypes," J. Pharmacol. Exp. Ther., Feb. 1991; 256(2), 727-733.
Fuhlendorff et al., "[Leu31, Pro34]neuropeptide Y: a specific Y1 receptor agonist," Proc. Natl. Acad. Sci. U.S.A., Jan. 1, 1990; 87(1), 182-186.

Grandy et al., "Cloning of the cDNA and gene for a human D2 dopamine receptor," Proc. Natl. Acad. Sci. U.S.A., Dec. 1, 1989; 86(24), 9762-9766.
Greengrass et al., "Binding characteristics of 3H-prazosin to rat brain α-adrenergic receptors," Eur. J. Pharmacol., May 1, 1979; 55(3), 323-326.
Hope et al., "Characterization of a human 5-hydroxytryptamine3 receptor type A (h5-HT3R-AS) subunit stably expressed in HEK 293 cells," Brit. J. Pharmacol., Jul. 1996; 118(5), 1237-1245.
Hoyer et al., "Characterization of the 5-HT1B recognition site in rat brain: Binding studies with (-)[125I] Iodocyanopindolol," Eur. J. Pharmacol., Nov. 26, 1985; 118(1-2), 1-12.
Hugues et al., "Preparation of a pure monoiodo derivative of the bee venom neurotoxin apamin and its binding properties to rat brain synaptosomes," J. Biol. Chem., Mar. 25, 1982; 257, 2762-2769.
Joseph et al., "Binding of (-)-[3H]-CGP12177 at two sites in recombinant human β1-adrenoreceptors and interaction with β-blockers," Naun. -Sch. Arch. Pharm., 2004, 369, 525-532.
Le et al., "Ligand binding and functional properties of human angiotensin AT1 receptors in transiently and stably expressed CHO-K1 cells," Eur. J. Pharmacol., Apr. 18, 2005; 513(1-2), 35-45.
Leurs et al., "Pharmacological characterization of the human histamine H2 receptor stably expressed in Chinese hamster ovary cells," Brit. J. Pharmacol., Jul. 1994; 112(3), 847-854.
Levin et al., "The Myocardium-protective Gly-49 Variant of the β1-Adrenergic Receptor Exhibits Constitutive Activity and Increased Desensitization and Down-regulation," J. Biol. Cham., May 28, 2002; 277(34), 30429-30435.
Lewin et al., "meta- and para-isothiocyanato-t-butylbicycloorthobenzoate: irreversible ligands of the gamma-aminobutyric acid-regulated chloride ionophore," Mol. Pharmacol., Feb. 1989; 35(2), 189-194.
Luthin et al., "Characterization of two affinity states of adenosine A2a receptors with a new radioligand, 2-[2-(4-amino-3-[125I]iodophenyl)ethylamino]adenosine," Mol. Pharmacol., Feb. 1995; 47(2), 307-313.
Maecke et al., "NODAGATOC, a New Chelator-Coupled Somatostatin Analogue Labeled with [67/68Ga] and [111In] for SPECT, PET, and Targeted Therapeutic Applications of Somatostatin Receptor (hsst2) Expressing Tumors," Bioconj. Chem., 2002, 13(3), 530-541.
Matentzoglu et al., "Ubiquitin-fusion protein system: a powerful tool for ectopic protein expression in mammalian cells," BioTechniques, Jan. 2009; 46(1), 21-28.
Meng et al., "Cloning and pharmacological characterization of a rat kappa opioid receptor," Proc. Natl. Acad. Sci. U.S.A., Nov. 1, 1993; 90(21), 9954-9958.
Monsma et al., "Cloning and expression of a novel serotonin receptor with high affinity for tricyclic psychotropic drugs," Mol. Pharmacol., Mar. 1993; 43(3), 320-327.
Mulheron et al., "Human 5-HT1A receptor expressed in insect cells activates endogenous G(o)-like G protein(s)," J. Biol. Chem., Apr. 29, 1994; 269(17), 12954-12962.
Neote et al., "Molecular cloning, functional expression, and signaling characteristics of a C—C chemokine receptor," Cell, Feb. 12, 1993; 72(3), 415-425.
Pacholczyk et al., "Expression cloning of a cocaine-and antidepressant-sensitive human noradrenaline transporter," Nature, Mar. 28, 1991; 350, 350-354.
Peralta et al., "Distinct primary structures, ligand-binding properties and tissue-specific expression of four human muscarinic acetylcholine receptors," EMBO. J., Dec. 1987; 6(13), 3923-3929.
Pristupa et al., "Pharmacological heterogeneity of the cloned and native human dopamine transporter: disassociation of [3H]WIN 35,428 and [3H]GBR 12,935 binding," Mol. Pharmacol., Jan. 1994; 45(1), 125-135.
Pruneau et al., "LF 16.0335, a novel potent and selective nonpeptide antagonist of the human bradykinin B2 receptor," Brit. J. Pharmacol., Sep. 1998; 125(2), 365-372.
Rees et al., "Cloning and characterisation of the human 5-HT5A serotonin receptor," FEBS Lett., Dec. 5, 1994; 355, 242-246.
Rettenbacher et al., "Localization and characterization of neuropeptide receptors in human colon," Naunyn Schmiedebergs Arch. Pharmacol., Oct. 2001; 364(4), 291-304.

(56) References Cited

OTHER PUBLICATIONS

Reynolds et al., "(-)-[3H] desmethoxyverapamil labels multiple calcium channel modulator receptors in brain and skeletal muscle membranes: differentiation by temperature and dihydropyridines," J. Pharmacol. Exp. Ther., Jun. 1986; 237(3), 731-738.

Rinaldi-Carmona et al., "Characterization of two cloned human CB1 cannabinoid receptor isoforms," J. Pharmacol. Exp. Ther., Aug. 1996; 278(2), 871-878.

Salvatore et al., "Molecular cloning and characterization of the human A3 adenosine receptor," Proc. Natl. Acad. Sci. U.S.A., Nov. 1, 1993; 90(21), 10365-10369.

Abramovitz et al., "The utilization of recombinant prostanoid receptors to determine the affinities and selectivities of prostaglandins and related analogs," Biochem. Biophys. Acta., Jan. 17, 2000; 1483(2), 285-293.

Aharony et al., "Pharmacological characterization of cloned human NK-2 (neurokinin A) receptor expressed in a baculovirus/Sf-21 insect cell system," Mol. Pharmacol., Aug. 1993; 44(2), 356-363.

Ardati et al., "Interaction of [3H]Orphanin FQ and 125I-Tyr14-Orphanin FQ with the Orphanin FQ Receptor: Kinetics and Modulation by Cations and Guanine Nucleotides," Mol. Pharmacol., May 1997; 51(5), 816-824.

Banker et al., "Development and validation of a 96-well equilibrium dialysis apparatus for measuring plasma protein binding," J. Pharm. Sci., May 2003; 92(5), 967-974.

Bignon et al., "SR146131: A New Potent, Orally Active, and Selective Nonpeptide Cholecystokinin Subtype 1 Receptor Agonist. I: In Vitro Studies," J. Pharmacol. Exp. Ther., May 1999; 289(2), 742-751.

Bloomquist et al., "Cloning and Expression of the Human Galanin Receptor GalR2," Biochem. Biophys. Res. Commun., Feb. 13, 1998; 243(2), 474-479.

Bonhaus et al., "The pharmacology and distribution of human 5-hydroxytryptamine2B (5-HT2b) receptor gene products: comparison with 5-HT2a and 5-HT2c receptors ," Brit. J. Pharmacol., Jun. 1995; 115(4), 622-628.

Brown et al., "Identification of somatostatin receptors by covalent labeling with a novel photoreactive somatostatin analog," J. Biol. Chem., Oct. 15, 1990; 265, 17995-18004.

Buchan et al., "Characterization of three non-peptide endothelin receptor ligands using human cloned ETA and ETB receptors ," Br. J. Pharmacol., Aug. 1994; 112(4), 1251-1257.

Smerlng et al, "Novel neurotensin-based radio-tracers for imaging and therapy of ductal pancreatic adenocarcinoma", NP2D Meeting, 3 pages, (2010).

Osterkamp et al, "Novel Neurotensin-based Radio-tracers for Imaging and Therapy of Ductal Pancreatic Adenocarcinoma", EANM Annual meeting, 2 pages, (2012).

\* cited by examiner

SEQUENCE LISTING

```
<160> NUMBER OF SEQ ID NOS: 3

<210> SEQ ID NO 1
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: Neurotensin
```

```
<400> SEQUENCE: 1

Glu Leu Tyr Glu Asn Lys Pro Arg Arg Pro Tyr Ile Leu
1               5                   10

<210> SEQ ID NO 2
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: Eight C-terminal amino acids of neurotensin

<400> SEQUENCE: 2

Lys Pro Arg Arg Pro Tyr Ile Leu
1               5

<210> SEQ ID NO 3
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Six C-terminal amino acids of neurotensin

<400> SEQUENCE: 3

Arg Arg Pro Tyr Ile Leu
1               5
```

NEUROTENSIN RECEPTOR LIGANDS

CROSS REFERENCE TO RELATED APPLICATIONS

This application is a U.S. National Stage Application of International Application No. PCT/EP2013/003700 filed Dec. 6, 2013, which claims priority from EP Patent Application No. 12 008 208.6 filed Dec. 7, 2012. The entirety of all the above-listed applications are incorporated herein by reference.

REFERENCE TO SEQUENCE LISTING

The instant application contains a Sequence Listing which has been submitted in ASCII format via EPS-Web and is hereby incorporated by reference in its entirety. Said ASCII copy, created on Dec. 7, 2012, is named TBP_001_SequenceListing.txt and is 941 bytes in size.

The present invention is related to a chemical compound; an antagonist of neurotensin receptor; a composition comprising the compound and antagonist, respectively; the compound, the antagonist and the composition, respectively, for use in a method for the diagnosis of a disease; the compound, the antagonist and the composition, respectively, for use in a method for the treatment of a disease; the compound, the antagonist and the composition, respectively, for use in a method of diagnosis and treatment of a disease which is also referred to as "thera(g)nosis" or "thera(g)nostics"; the compound, the antagonist and the composition, respectively, for use in a method for delivering an effector to a neurotensin expressing tissue; a method for the diagnosis of a disease using the compound, the antagonist and the composition, respectively; a method for the treatment of a disease using the compound, the antagonist and the composition, respectively; a method for the diagnosis and treatment of a disease which is also referred to as "thera(g)nosis" or "thera(g)nostics, using the compound, the antagonist and the composition, respectively; a method for the delivery of an effector to a neurotensin receptor expressing tissue using the compound, the antagonist and the composition, respectively.

Neurotensin NT is a 13 amino acid neuropeptide (pyro-Glu$^1$-Leu$^2$-Tyr$^3$-Glu$^4$-Asn$^5$-Lys$^6$-Pro$^7$-Arg$^8$-Arg$^9$-Pro$^{10}$-Tyr$^{11}$-Ile$^{12}$-Leu$^{13}$-OH) (SEQ ID NO: 1) that is implicated in the regulation of luteinizing hormone and prolactin release and has significant interaction with the dopaminergic system. Neurotensin was first isolated from extracts of bovine hypothalamus based on its ability to cause a visible vasodilation in the exposed cutaneous regions of anesthetized rats (Carraway et al., *J. Biol. Chem.*, 1973, 248, 6854-6861).

Neurotensin is distributed throughout the central nervous system, with highest levels in the hypothalamus, amygdala and nucleus accumbens. It induces a variety of effects, including analgesia, hypothermia and increased locomotor activity. It is also involved in regulation of dopamine pathways. In the periphery, neurotensin is found in endocrine cells of the small intestine, where it leads to secretion and smooth muscle contraction (Friry et al., *Biochem. Biophys. Res. Commun.*, 2002, 290, 1161-1168).

Neurotensin is bound by neurotensin receptors. Three neurotensin receptors are known, namely neurotensin receptor 1, also referred to as NTR1, neurotensin receptor 2, also referred to as NTR2, and neurotensin receptor 3, also referred to as NTR3. These neurotensin receptors are transmembrane receptors that bind the neurotransmitter neurotensin (Vincent et al., *Trends Pharmacol. Sci.*, 1999, 20, 302-309; Pelaprat, *Peptides*, 2006, 27, 2476-2487). NTR1 and NTR2 which are encoded by the NTSR1 and NTSR2 genes, contain seven transmembrane helices and are G protein coupled. NTR3 has a single transmembrane domain and is encoded by the SORT1 gene.

The neurotensin receptor 1 (NTR1) was cloned in 1990 from rat brain and found to act as a high affinity, levocabastine insensitive receptor for neurotensin (Tanaka et al., *Neuron*, 1990, 4, 847-854). The affinity of neurotensin for the receptor could be decreased by both sodium ions and guanosine triphosphate (GTP) (Vincent et al., *Trends Pharmacol. Sci.*, 1999, 20, 302-309). NTR1 is expressed predominantly in the central nervous system and intestine (smooth muscle, mucosa and nerve cells). In the central nervous system, expression has been found in the diagonal band of Broca, medial septal nucleus, nucleus basalis magnocellularis, suprachiasmatic nucleus, supramammillary area, substantia nigra and ventral tegmental area. The receptor is also expressed in the dorsal root ganglion neurones of the spinal cord. The predominant response upon activation of the receptor by neurotensin is activation of phospholipase C, causing an increase in intracellular calcium levels. The receptor can also stimulate cAMP formation, MAP kinase activation and the induction of growth related genes, such as krox-24 (Vincent et al., *Trends Pharmacol. Sci.*, 1999, 20, 302-309).

Neurotensin receptor 2 (NTR2) is a protein that in humans is encoded by the NTSR2 gene (Vincent et al., *Trends Pharmacol. Sci.*, 1999, 20, 302-309; Mazella et al., *J. Neurosci.*, 1996, 16, 5613-5620; Ramez et al., *J. Invest. Dermatol.*, 2001, 117, 687-693). The protein encoded by this gene belongs to the G protein-coupled receptor family that activates a phosphatidylinositol-calcium second messenger system. Binding and pharmacological studies demonstrate that this receptor binds neurotensin as well as several other ligands already described for NTR1. However, unlike NTR1, NTR2 recognizes, with high affinity, levocabastine, a histamine H1 receptor antagonist previously shown to compete with neurotensin for low-affinity binding sites in the central nervous system. These activities suggest that this receptor may be of physiological importance and that a natural agonist for the receptor may exist.

Neurotensin receptor 3 (NTR3) is a non-G-protein coupled receptor. The cDNA encodes an 833-amino acid protein 100% identical to the recently cloned gp95/sortilin and was then designated NTR3/gp95/sortilin (Mazella, *Cell Signal.*, 2001, 13, 1-6; Vincent et al., *Trends Pharmacol. Sci.*, 1999, 20, 302-309). NTR3 is a sorting protein involved in cellular trafficking and neuropeptide signalling. The physiological and cellular roles of sortilin/NTR3 are putative in many aspects and still under discussion.

Apart from the central nervous system, NTR1 is highly expressed in a mammalian body and a human body in particular on several neoplastic cells in several tumor indications, whereas the expression of NTR1 in most other tissues of the mammalian and the human body is either not existent or low. Only for colon weak or moderate expression under physiological conditions is described.

The following table summarizes the expression of NTR1 as described in the prior art indicating the tissue, degree of expression, detection method and the respective references.

| Tissue | Expression | Detection method Reference |
| --- | --- | --- |
| Central Nervous System (e.g. substantia nigra, suprachiasmatic nucleus) | +++ | Autoradiography, immunohistochemistry, in situ hybridization e.g. Boudin et al., *J. Comp. Neurol.*, 1996, 373, 76-89 (and references herein) |
| Colon (mucosa, normal) | +/− | In situ hybridization Gui et al., *Peptides*, 2008, 29, 1609-15 |
| Colon (smooth muscle, normal) | +/++ | Autoradiography Rettenbacher et al., *Naunyn Schmiedebergs Arch. Pharmacol.*, 2001, 364, 291-304 |
| Ductal pancreatic adenocarcinoma | +++ | Autoradiography, RT-PCR, Immunohistochemistry, cell line studies Reubi et al., *Gut*, 1998, 42, 546-50; Ehlers et al., *Ann. Surg.*, 2000, 231, 838-48; Iwase et al., *Cancer*, 1997, 79, 1787-1793; Wang et al., *Neuropeptides*, 2011, 45, 151-156; Wang et al., *Clin. Cancer Res.*, 2000, 6, 566-571 |
| Small cell lung cancer | ++ | Autoradiography, cell line studies Reubi et al., *Int. J. Cancer*, 1999, 82, 213-218; Moody et al., *Peptides*, 2001, 22, 109-115 |
| Prostate cancer | ++ | RT-PCR (xenografts), functional studies, Taylor et al., *Prostate*, 2012, 72, 523-32; Amorino et al., *Oncogene*, 2007, 26, 745-756; Valerie et al., *Cancer Res.*, 2011, 71, 6817-6826; Swift et al., *Cancer Res.*, 2010, 70, 347-356; Almeida et al., *Peptides*, 2010, 31, 242-247 |
| Colorectal carcinoma | ++/+++ | RT-PCR, in situ hybridization, immunohistochemistry, mouse model, cell line studies Chao et al., *J. Surg. Res.*, 2005, 129, 313-321; Gui et al., *Peptides*, 2008, 29, 1609-1615; Bossard et al., *Peptides*, 2007, 28, 2030-2035; Bugni et al., *Int. J. Cancer*, 2012, 130, 1798-1805, Haase et al., *Anitcancer Res.*, 2006, 26, 3527-3533; Martin et al., *Gastroenterology*, 2002, 123, 1135-1143 |
| Breast cancer | + | Immunohistochemistry Souaze et al., *Cancer Res.*, 2006, 66, 6243-6249; Dupouy et al., *PLoS One*, 2009, 4, e4223 |
| Meningioma | +++ | Autoradiography Reubi et al., *Int. J. Cancer*, 1999, 82, 213-218 |
| Ewing's Sarcoma | +++ | Autoradiography Reubi et al., *Int. J. Cancer*, 1999, 82, 213-218 |
| Pleural Mesothelioma | ++ | Immunohistochemistry Alifano et al., *Biochimie*, 2010, 92, 164-170 |
| Head and Neck Cancer | + | Functional study Shimizu et al., *Int. J. Cancer*, 2008, 123, 1816-1823 |
| Lung Cancer | ++ | Immunohistochemistry, cell line studies, RT-PCR Alifano et al., *Clin. Cancer Res.*, 2010, 16, 4401-4410; Moody et al., *Panminerva Med.*, 2006, 48, 19-26; Ocejo-Garcia et al., *Lung Cancer*, 2001, 33, 1-9 |
| Gastrointestinal Stromal Tumors | ++ | Gromova et al., *PLoS One*, 2011, 6, e14710 |
| Uterine Leiomyoma | ++ | Immunohistochemistry, RT-PCR Rodriguez et al., *Biol. Reprod.*, 2010, 83, 641-647; Rodriguez et al., *Int. J. Gynecol Pathol*, 2011, 30, 354-363 |
| Cutaneous T-Cell Lymphoma | ++ | Flow cytometry Ramez et al., *J. Invest. Dermatol*, 2001, 117, 687-693 |

Expression: +/− scattered or heterogeneous; + weak; ++ moderate; +++ strong

These NTR1 expressing tumor indications include but are not limited to ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma. A preferred group of NTR1 expressing tumor indications are ductal pancreatic adenocarcinoma, small cell lung cancer, prostate cancer, colorectal cancer, breast cancer, meningioma and Ewing's sarcoma.

Because of this selective expression of NTR1, NTR1 is regarded as a suitable target for drugs and diagnostic agents. Agonists and antagonists binding to NTR1 have been described in the prior art. One class of such NTR1 agonists are peptides binding to NTR1.

Most of these agonist peptides are derivatives of neurotensin, its C-terminal eight amino acids Lys$^6$-Pro$^7$-Arg$^8$-Arg$^9$-Pro$^{10}$-Tyr$^{11}$-Ile$^{12}$-Leu$^{13}$ (NT6-13) (SEQ ID NO: 2) or its C-terminal six amino acids Arg$^8$-Arg$^9$-Pro$^{10}$-Tyr$^{11}$-Ile$^{12}$-Leu$^{13}$ (NT8-13) (SEQ ID NO: 3). Modifications include for example N-methylations, reduced amide bonds, β-Ala or D-Lys at position 7, Gly(PipAm) at position 8, Dab or Phe(4-Gu) at position 9, Dmt at position 11, Tle or tBuGly at position 12, D-Leu or Cha at position 13 as well as combinations thereof. U.S. Pat. No. 4,439,359 discloses cyclic octapeptide analogs of neurotensin. U.S. Pat. No. 4,425,269 discloses metabolically protected analogs of neurotensin. WO 1999/052539 discloses neurotensin analogs with the novel non-natural amino acid Neo-tryptophan. WO 2000/078796 discloses labeled neurotensin derivatives, some of them with improved resistance to enzymatic degradation. WO 1995/022341 discloses labeled peptide compounds. US 2010/0256055 discloses conjugates of neurotensin or neurotensin analogs and uses thereof. U.S. Pat. No. 4,110,321 discloses a synthetic tridecapeptide [Gln$^4$]-neurotensin having hormonal activity. WO 2011006985 discloses neurotensin analogues for radioisotope targeting to neurotensin receptor-positive tumors. EP 0606804, WO 1996/031531, WO 1997/004311 and WO 1998/001472 disclose marker for the neurotensin receptor including fluorescently labeled markers. U.S. Pat. No. 5,407,916 discloses neurotensin mimetics as central nervous system agents.

These peptides as well as the further ligands of NTR1, namely neuromedin N and xenin, can be used for imaging purposes and therapeutic purposes. Typically, the agonist carries a therapeutically or diagnostically active effector such as a chelated metal label and more specifically a chelated radiolabel suitable for therapy and diagnosis, respectively. The effector bearing agonist binds to the receptor and, upon binding to the receptor, the effector bearing agonist is internalized by the receptor and the effector bearing agonist thus trapped in the target cell. It will be understood by a person skilled in the art that such trapping of the effector bearing agonist may go along with the release of the effector from the agonist. Additionally, upon such trapping, the effector and/or the agonist may be subject to metabolic conversion. Such metabolic conversion may occur through the metabolism and enzymatic activities in particular of the organism to which the effector bearing agonist has been administered and more specifically the metabolism of the cell and tissue, respectively, into which the effector bearing agonist has been internalized.

The potential utility of metal labeled neurotensin receptor specific peptidic agonists for scintigraphic or SPECT or PET imaging and radiotherapy is exemplified by the $^{99m}$Tc-labelled neurotensin (NT) analog NT-XI (Buchegger et al., J. Nucl. Med., 2003, 44, 1649-1654) or $^{99m}$Tc-labelled neurotensin (NT) analog $^{99m}$Tc-Demotensin VI (Gabriel et al., Cancer Biother. Radiopharm., 2011, 26, 557-563).

Metal labeled neurotensin receptor specific ligands have also been used for preclinical tumor imaging for example of NTR1-expressing HT29 xenograft tumors using $^{99m}$Tc-NTXIX (Garcia-Garayoa et al., Eur. J. Nucl. Med. Mol. Imaging, 2009, 36, 37-47). Such neurotensin receptor specific ligands are NT(8-13) analogs (Garcia-Garayoa et al., Nucl. Med. Biol., 2001, 28, 75-84; Garcia-Garayoa et al., J. Nucl. Med., 2002, 43, 374-383; Garcia-Garayoa et al., Nucl. Med. Biol., 2006, 33, 495-503; Garcia-Garayoa et al., Eur. J. Nucl. Med. Mol. Imaging, 2009, 36, 37-47; Bergmann et al., Nucl. Med. Biol., 2002, 29, 61-72; Bruehlmeier et al., Nucl. Med. Biol., 2002, 29, 321-327; Blauenstein et al., Cancer Biother. Radiopharm., 2004, 19, 181-188; Maes et al., J. Med. Chem., 2006, 49, 1833-1836), demotensins (Nock et al., J. Med. Chem., 2006, 49, 4767-4776; Maina et al., Eur. J. Nucl. Med. Mol. Imaging, 2007, 34, 1804-1814), NT(6-13) analogs (Alshoukr et al., Bioconjug. Chem., 2009, 20, 1602-1610; Alshoukr et al., Bioconjug. Chem., 2011, 22, 1374-1385) and neurotensin analogs developed by Biosynthema (Achilefu et al., J. Med. Chem., 2003, 46: 3403-3411; de Visser et al., Eur. J. Nucl. Med. Mol. Imaging, 2003, 30, 1134-1139; and Janssen et al., Cancer Biother. Radiopharm., 2007, 22, 374-381).

It was found that (most) neurotensin-derived metal labeled peptides have a very short circulation half-life due to rapid renal clearance as often observed for peptidic molecules. Consequently, tumor accumulation is rather limited for such molecules.

International patent application WO 98/33531 discloses methods for the detection and localization of malignant human tumors using neurotensin, peptide NTR agonists and peptide NTR antagonists, respectively. The example part of WO 98/33531 shows the use of $^{125}$I labeled and unlabeled neurotensin and fragments thereof acting as agonists in receptor autoradiography of cryostat sections of tumor samples.

U.S. Pat. No. 5,723,483 discloses small molecule compounds which are active as NTR1 antagonists such as SR142948. These small molecule compounds and SR142948 in particular, however, cross the blood-brain barrier and are thus suitable neither for the radionuclide therapy of tumors nor for the radioactive diagnosis of tumors and imaging in particular, whereby the tumors are preferably those expressing NTR1, since irradiation of the central nervous system may have detrimental effects on the patient Additionally, the radiolabeling of these compounds is difficult. Even more difficult is designing and synthesizing a radiolabeled derivative of these compounds without diminishing or destroying the original and desired high NTR1 affinity.

The above overview of the prior art attempting to provide a compound which can be used in the diagnosis and/or therapy of NTR1-expressing tumors, whereby such diagnosis and therapy typically makes use of a radiolabeled version of such compound, illustrates the difficulties in designing this kind of compounds being effective and thus suitable for such diagnostic and therapeutic purpose. It is imperative that the compound has appropriate in vivo targeting and pharmacokinetic properties. It is, however, well known that the radionuclide chemistry and associated linkages are crucial particularly with respect to the attachment to the compound of an effector which provides the signal needed for diagnosis or which provides the therapeutically effective activity. Such effector can be attached to the compound either directly or through a connecting moiety. In case the effector is a radiolabel and the radiolabel is attached to the compound by a connecting moiety such as, for example, a chelator, the labeling of such a connecting moiety and chelator, respectively, is a further crucial step in the identification of a suitable compound (Fritzberg et al., J. Nucl. Med., 1992, 33, 394-397). Hence the type of radionuclide, the type of compound which mediates target binding, and the method used for linking them to one another may have unpredictable effects on the properties of the radiolabeled version of the compound. Theoretically, a high affinity of the compound as such, i.e. without the radiolabel, a connecting moiety and/or chelator, respectively, if any, for the target receptor facilitates retention of the compound and the radiolabeled version thereof in particular in target receptor expressing tissues. However, it is well known that the affinity and receptor specificity of the compound as such, i.e. without the radiolabel and the linker and chelator, respectively, if any, may be completely altered during chemical modification and radionuclide labeling (Fani et al., *J. Nucl. Med.*, 2012, 53, 1481-1489). Therefore, an optimal compound and even more so a radiolabeled version thereof suitable for diagnosis and therapy, respectively, of a disease is a matter of luck rather than of a rational and predictable development process.

The problem underlying the present invention is the provision of a compound which is suitable as a diagnostic agent and/or a pharmaceutical agent, particularly if conjugated to a diagnostically and/or therapeutically active effector. A further problem underlying the present invention is the provision of a compound which is suitable as a diagnostic agent and/or a pharmaceutical agent, particularly if conjugated to a diagnostically and/or therapeutically active effector, and which does not penetrate the blood-brain barrier. A further problem underlying the present invention is the provision of a compound which is suitable as a diagnostic agent and/or a pharmaceutical agent, particularly if conjugated to a diagnostically and/or therapeutically active effector, in the diagnosis and/or therapy of a disease where the diseased cells and/or diseased tissues express NTR1. A still further problem underlying the instant invention is the provision of a compound which is suitable for delivering a diagnostically and/or therapeutically effective agent to a diseased cell and/or diseased tissue, respectively, and more particularly an NTR1-expressing diseased cell and/or diseased tissue. Also, a problem underlying the present invention is the provision of a method for the diagnosis of a disease, of a method for the treatment and/or prevention of a disease, and a method for the combined diagnosis and treatment of a disease; preferably such disease is a disease involving NTR1-expressing cells and/or tissues. A still further problem underlying the present invention is the provision of a method for the identification of a subject, wherein the subject is likely to respond or likely not to respond to a treatment of a disease, a method for the selection of a subject from a group of subjects, wherein the subject is likely to respond or likely not to respond to a treatment of a disease. Also, a problem underlying the present invention is the provision of a pharmaceutical composition containing a compound having the characteristics as outlined above. Furthermore, a problem underlying the present invention is the provision of a kit which is suitable for use in any of the above methods These and other problems are solved by the subject matter of the attached independent claims. Preferred embodiments may be taken from the attached dependent claims.

These and other problems underlying the present invention are also solved by the following embodiments.

Embodiment 1

A compound of formula (I):

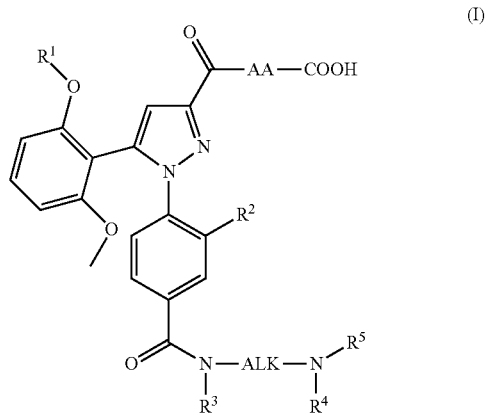

wherein
R¹ is selected from the group consisting of hydrogen, methyl and cyclopropylmethyl;
AA-COOH is an amino acid selected from the group consisting of 2-amino-2-adamantane carboxylic acid, cyclohexylglycine and 9-amino-bicyclo[3.3.1]nonane-9-carboxylic acid;
R² is selected from the group consisting of $(C_1\text{-}C_6)$alkyl, $(C_3\text{-}C_8)$cycloalkyl, $(C_3C_8)$cycloalkylmethyl, halogen, nitro and trifluoromethyl;
ALK is $(C_2\text{-}C_5)$alkylidene;
R³, R⁴ and R⁵ are each and independently selected from the group consisting of hydrogen and $(C_1\text{-}C_4)$alkyl under the proviso that one of R³, R⁴ and R⁵ is of the following formula (II)

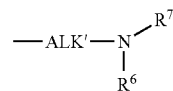

wherein
ALK' is $(C_2\text{-}C_5)$alkylidene;
R⁶ is selected from the group consisting of hydrogen and $(C_1\text{-}C_4)$alkyl; and
R⁷ is selected from the group comprising H and an Effector moiety;
or a pharmacologically acceptable salt, solvate or hydrate thereof Embodiment 2

The compound of embodiment 1, wherein the Effector moiety is comprising or capable of comprising an Effector, wherein the Effector is selected from the group comprising a diagnostically active agent, a therapeutically active agent and a combination thereof.

Embodiment 3

The compound of embodiments 1 to 2, wherein the Effector moiety is selected from the group comprising Acceptor, -[Acceptor-Effector], -[Linker-Acceptor], and -[Linker-Acceptor-Effector], wherein Acceptor is a moiety which mediates linking of an Effector to the N atom of formula (II) or which mediates linking of the Effector to the Linker, Effector is selected from the group comprising a diagnostically active agent and a therapeutically active agent, Linker is a moiety which links the Acceptor to the N atom of formula (II), -[Acceptor-Effector] is a moiety where the Effector is complexed or covalently bound to the Acceptor, -[Linker-Acceptor] is a moiety where the Linker is conjugated to the Acceptor, and -[Linker-Acceptor-Effector] is a moiety where the Linker is conjugated to the Acceptor, whereby the Effector is complexed or covalently bound to the Acceptor;

or a pharmacologically acceptable salt, solvate or hydrate thereof.

Embodiment 4

The compound of any one of embodiments 1, 2 and 3, wherein $R^1$ is methyl.

Embodiment 5

The compound of any one of embodiments 1, 2, 3, 4, and 5, wherein AA-COOH is an amino acid selected from the group consisting of 2-amino-2-adamantane carboxylic acid and cyclohexylglycine.

Embodiment 6

The compound of embodiment 5, wherein AA-COOH is 2-amino-2-adamantane carboxylic acid.

Embodiment 7

The compound of embodiment 5, wherein AA-COOH is cyclohexylglycine.

Embodiment 8

The compound of any one of embodiments 1, 2, 3, 4, 5, 6 and 7 preferably any one of embodiments 1, 2 and 3 wherein $R^2$ is isopropyl.

Embodiment 9

The compound of any one of embodiments 1, 2, 3, 4, 5, 6, 7 and 8 preferably any one of embodiments 1, 2 and 3, wherein $R^3$, $R^4$ and $R^5$ are each and independently selected from the group consisting of hydrogen and methyl under the proviso that one of $R^3$, $R^4$ and $R^5$ is of the following formula (II)

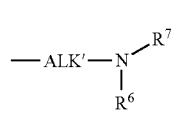

(II)

wherein
ALK' is $(C_2-C_5)$alkylidene;
$R^6$ is selected from the group consisting of hydrogen and $(C_1-C_4)$alkyl.

Embodiment 10

The compound of embodiment 9, wherein $R^6$ is selected from the group consisting of hydrogen and methyl.

Embodiment 11

The compound of any one of embodiments 1, 2, 3, 4, 5, 6, 7, 8, 9 and 10, preferably any one of embodiments 1, 2 and 3, wherein $R^7$ is H.

Embodiment 12

The compound of any one of embodiments 1, 2, 3, 4, 5, 6, 7, 8, 9 and 10, wherein Effector is a diagnostically active nuclide, preferably a diagnostically active radionuclide, or a therapeutically active nuclide, preferably a therapeutically active radionuclide.

Embodiment 13

The compound of any one of embodiments 1, 2, 3, 4, 5, 6, 7, 8, 10, 11 and 12, preferably any one of embodiments 9, 10 and 12, wherein $R^7$ is selected from the group comprising Acceptor, -[Acceptor-Effector], -[Linker-Acceptor] and -[Linker-Acceptor-Effector].

Embodiment 14

The compound of embodiments 13, wherein $R^7$ is Acceptor and one of $R^3$, $R^4$ and $R^5$ is of formula (IIa):

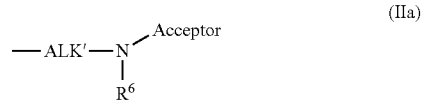

(IIa)

Embodiment 15

The compound of embodiment 14, wherein Acceptor is a chelator.

Embodiment 16

The compound of embodiment 14, wherein Acceptor comprises an aromatic moiety, wherein the aromatic moiety is selected from the group comprising indole and benzene, preferably benzene is substituted with at least one heteroatom, wherein the heteroatom is selected from the group comprising an O, an N and S.

Embodiment 17

The compound of embodiment 13, wherein $R^7$ is -[Acceptor-Effector] and one of $R^3$, $R^4$ and $R^5$ is of formula (IIb):

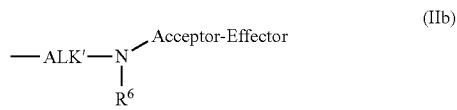

(IIb)

Embodiment 18

The compound of embodiment 17, wherein Acceptor is a chelator and Effector is a diagnostically active nuclide, preferably a diagnostically active radionuclide, or a therapeutically active nuclide, preferably a therapeutically active radionuclide.

Embodiment 19

The compound of embodiment 17, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S, and wherein Effector is a diagnostically active nuclide, preferably a diagnostically active radionuclide, or a therapeutically active nuclide, preferably a therapeutically active radionuclide.

Embodiment 20

The compound of embodiment 13, wherein $R^7$ is -[Linker-Acceptor] and one of $R^3$, $R^4$ and $R^5$ is of formula (IIc):

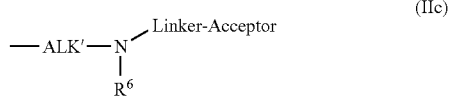

Embodiment 21

The compound of embodiment 20, wherein Linker is a moiety which covalently links the N atom of the group of formula (II) with the Acceptor, wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 22

The compound of any one of embodiments 20 and 21, preferably embodiment 21, wherein Acceptor is a chelator.

Embodiment 23

The compound of any one of embodiments 20 and 21, preferably embodiment 21, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 24

The compound of embodiment 13, wherein $R^7$ is -[Linker-Acceptor-Effector] and one of $R^3$, $R^4$ and $R^5$ is of formula (IId):

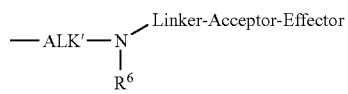

Embodiment 25

The compound of embodiment 24, wherein
Effector is a diagnostically active nuclide, preferably a diagnostically active radionuclide, or a therapeutically active nuclide, preferably a therapeutically active radionuclide,
Acceptor is a chelator, and
Linker is a moiety which covalently links the N atom of the group of formula (II) with the Acceptor, wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 26

The compound of embodiment 24, wherein
Effector is a diagnostically active nuclide, preferably a diagnostically active radionuclide, or a therapeutically active nuclide, preferably a therapeutically active radionuclide,
Acceptor comprises an aromatic moiety, wherein the aromatic moiety is selected from the group comprising indole and benzene, preferably benzene is substituted with at least one heteroatom, wherein the heteroatom is selected from the group comprising O, N and S, and
Linker is a moiety which covalently links the N atom of the group of formula (II) with the Acceptor, wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 27

The compound of any one of embodiments 1, 2, 3, 4, 5, 6, 7, 8, 9, 10, 11, 12, 13, 14, 15, 16, 17, 18, 19, 20, 21, 22, 23, 24, 25 and 26, preferably any one of embodiments 1, 2, 3, 12, 13, 14, 15, 16, 17, 18, 19, 20, 21, 22, 23, 24, 25 and 26, wherein $R^3$, $R^4$ and $R^5$ are each and independently methyl under the proviso that one of $R^3$, $R^4$ and $R^5$ is of the following formula (II):

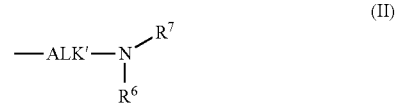

wherein
ALK' is $(C_2-C_5)$alkylidene;
$R^6$ is selected from the group consisting of hydrogen and methyl.

Embodiment 28

The compound of any one of embodiments 1, 2, 3, 4, 5, 6, 7, 8, 9, 10, 11, 12, 13, 14, 15, 16, 17, 18, 19, 20, 21, 22, 23, 24, 25, 26 and 27, preferably any one of embodiments 1, 2, 3 and 27, wherein ALK and ALK' are both propylene, or wherein either ALK is propylene and ALK' is ($C_2$-$C_5$)alkylidene or ALK is ($C_2$-$C_5$)alkylidene and ALK' is propylene.

Embodiment 29

The compound of any one of embodiments 1, 2 and 3, wherein
$R^1$ is methyl;
AA-COOH is an amino acid selected from the group consisting of 2-amino-2-adamantane carboxylic acid and cyclohexylglycine; and
$R^2$ is isopropyl.

Embodiment 30

The compound of any one of embodiments 1, 2, 3 and 29, wherein
$R^3$, $R^4$ and $R^5$ are each and independently selected from the group consisting of hydrogen and methyl under the proviso that one of $R^3$, $R^4$ and $R^5$ is of the following formula (II):

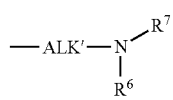
(II)

wherein
ALK' is ($C_2$-$C_5$)alkylidene;
$R^6$ is selected from the group consisting of hydrogen and methyl.

Embodiment 31

The compound of any one of embodiments 1, 2, 3, 29 and 30, preferably any one of embodiments 29 and 30, wherein $R^7$ is Acceptor and one of $R^3$, $R^4$ and $R^5$ is of formula (IIa):

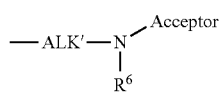
(IIa)

Embodiment 32

The compound of embodiment 31, wherein Acceptor is a chelator.

Embodiment 33

The compound of embodiment 31, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 34

The compound of any one of embodiments 1, 2, 3, 29 and 30, preferably any one of embodiments 29 and 30, wherein $R^7$ is -[Acceptor-Effector] and one of $R^3$, $R^4$ and $R^5$ is of formula (IIb):

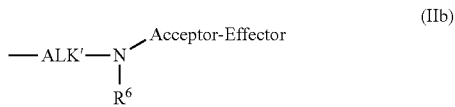
(IIb)

Embodiment 35

The compound of embodiment 34, wherein Acceptor is a chelator and Effector is a diagnostically active nuclide, preferably a diagnostically active radionuclide, or a therapeutically active nuclide, preferably a therapeutically active radionuclide.

Embodiment 36

The compound of embodiment 34, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S, and wherein Effector is a diagnostically active nuclide, preferably a diagnostically active radionuclide, or a therapeutically active nuclide, preferably a therapeutically active radionuclide.

Embodiment 37

The compound of any one of embodiments 1, 2, 3, 29 and 30, preferably any one of embodiments 29 and 30, wherein $R^7$ is -[Linker-Acceptor] and one of $R^3$, $R^4$ and $R^5$ is of formula (IIc):

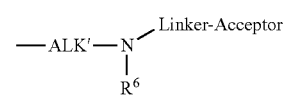
(IIc)

Embodiment 38

The compound of embodiment 37, wherein Linker is a moiety which covalently links the N atom of the group of formula (II) with the Acceptor, wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 39

The compound of any one of embodiments 37 and 38, preferably embodiment 38, wherein Acceptor is a chelator.

Embodiment 40

The compound of any one of embodiments 37 and 38, preferably embodiment 38, wherein Acceptor comprises an aromatic moiety, wherein the aromatic moiety is selected from the group comprising indole and benzene, preferably

Embodiment 41

The compound of any one of embodiments 1, 2, 3, 29 and 30, preferably any one of embodiments 29 and 30, wherein $R^7$ is -[Linker-Acceptor-Effector] and one of $R^3$, $R^4$ and $R^5$ is of formula (IId):

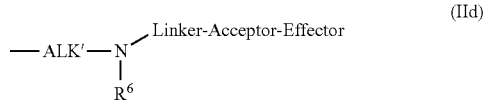

(IId)

Embodiment 42

The compound of embodiment 41, wherein
Effector is a diagnostically active nuclide, preferably a diagnostically active radionuclide, or a therapeutically active nuclide, preferably a therapeutically active radionuclide,
Acceptor is a chelator, and
Linker is a moiety which covalently links the N atom of the group of formula (II) with the acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 43

The compound of embodiment 41, wherein
Effector is a diagnostically active nuclide, preferably a diagnostically active radionuclide, or a therapeutically active nuclide, preferably a therapeutically active radionuclide,
Acceptor comprises an aromatic moiety, wherein the aromatic moiety is selected from the group comprising indole and benzene, preferably benzene is substituted with at least one heteroatom, wherein the heteroatom is selected from the group comprising O, N and S, and
Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 44

The compound according to any one of embodiments 1, 2 and 3, wherein
$R^1$ is methyl;
AA-COOH is an amino acid selected from the group consisting of 2-amino-2-adamantane carboxylic acid and cyclohexylglycine; and
$R^2$ is isopropyl.

Embodiment 45

The compound of embodiment 44, wherein $R^7$ is Acceptor and one of $R^3$, $R^4$ and $R^5$ is of formula (IIa):

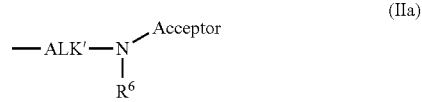

(IIa)

Embodiment 46

The compound of embodiment 45, wherein Acceptor is a chelator.

Embodiment 47

The compound of embodiment 45, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 48

The compound of embodiment 44, wherein $R^7$ is -[Acceptor-Effector] and one of $R^3$, $R^4$ and $R^5$ is of formula (IIb):

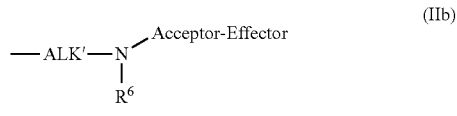

(IIb)

Embodiment 49

The compound of embodiment 48, wherein Acceptor is a chelator and Effector is a diagnostically active nuclide, preferably a diagnostically active radionuclide, or a therapeutically active nuclide, preferably a therapeutically active radionuclide.

Embodiment 50

The compound of embodiment 48, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S; and wherein Effector is a diagnostically active nuclide, preferably a diagnostically active radionuclide, or a therapeutically active nuclide, preferably a therapeutically active radionuclide.

Embodiment 51

The compound of embodiment 44, wherein $R^7$ is -[Linker-Acceptor] and one of $R^3$, $R^4$ and $R^5$ is of formula (IIc):

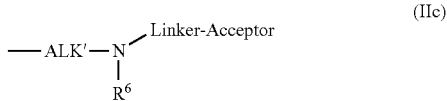

(IIc)

Embodiment 52

The compound of embodiment 51, wherein Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 53

The compound of any one of embodiments 51 and 52, preferably embodiment 52, wherein Acceptor is a chelator.

Embodiment 54

The compound of any one of embodiments 51 and 52, preferably embodiment 52, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 55

The compound of embodiment 44, wherein $R^7$ is -[Linker-Acceptor-Effector] and one of $R^3$, $R^4$ and $R^5$ is of formula (IId):

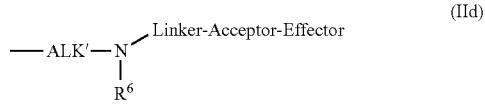

(IId)

Embodiment 56

The compound of embodiment 55, wherein
Effector is a diagnostically active nuclide, preferably a diagnostically active radionuclide, or a therapeutically active nuclide, preferably a therapeutically active radionuclide,
Acceptor is a chelator, and
Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 57

The compound of embodiment 55, wherein
Effector is a diagnostically active nuclide, preferably a diagnostically active radionuclide, or a therapeutically active nuclide, preferably a therapeutically active radionuclide,
Acceptor comprises an aromatic moiety, wherein the aromatic moiety is selected from the group comprising indole and benzene, preferably benzene is substituted with at least one heteroatom, wherein the heteroatom is selected from the group comprising O, N and S, and
Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 58

The compound of any one of embodiments 1, 2 and 3, wherein
$R^1$ is methyl;
AA-COOH is an amino acid selected from the group consisting of 2-amino-2-adamantane carboxylic acid and cyclohexylglycine;
$R^2$ is isopropyl;
$R^3$, $R^4$ and $R^5$ are each and independently selected from the group consisting of hydrogen and methyl under the proviso that one of $R^3$, $R^4$ and $R^5$ is of the following formula (II):

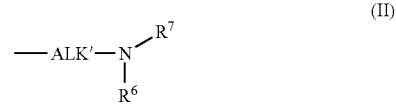

(II)

wherein
ALK' is $(C_2\text{-}C_5)$alkylidene; and
$R^6$ is selected from the group consisting of hydrogen and methyl.

Embodiment 59

The compound of embodiment 58, wherein $R^7$ is Acceptor and one of $R^3$, $R^4$ and $R^5$ is of formula (IIa):

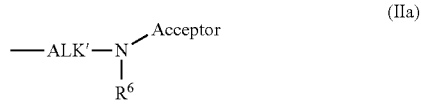

(IIa)

Embodiment 60

The compound of embodiment 59, wherein Acceptor is a chelator.

Embodiment 61

The compound of embodiment 59, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 62

The compound of embodiment 58, wherein $R^7$ is -[Acceptor-Effector] and one of $R^3$, $R^4$ and $R^5$ is of formula (IIb):

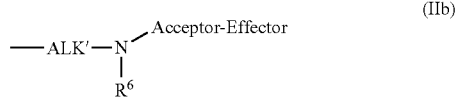
(IIb)

Embodiment 63

The compound of embodiment 62, wherein Acceptor is a chelator and Effector is a diagnostically active nuclide, preferably a diagnostically active radionuclide, or a therapeutically active nuclide, preferably a therapeutically active radionuclide.

Embodiment 64

The compound of embodiment 62, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S, and wherein Effector is a diagnostically active nuclide, preferably a diagnostically active radionuclide, or a therapeutically active nuclide, preferably a therapeutically active radionuclide.

Embodiment 65

The compound of embodiment 58, wherein $R^7$ is -[Linker-Acceptor] and one of $R^3$, $R^4$ and $R^5$ is of formula (IIc):

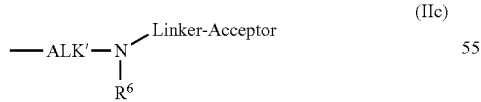
(IIc)

Embodiment 66

The compound of embodiment 65, wherein Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 67

The compound of any one of embodiments 65 and 66, preferably embodiment 66, wherein Acceptor is a chelator.

Embodiment 68

The compound of any one of embodiments 65 and 66, preferably embodiment 66, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 69

The compound of embodiment 58, wherein $R^7$ is -[Linker-Acceptor-Effector] and one of $R^3$, $R^4$ and $R^5$ is of formula (IId):

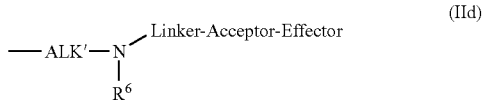
(IId)

Embodiment 70

The compound of embodiment 69, wherein
Effector is a diagnostically active nuclide, preferably a diagnostically active radionuclide, or a therapeutically active nuclide, preferably a therapeutically active radionuclide,
Acceptor is a chelator, and
Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 71

The compound of embodiment 69, wherein
Effector is a diagnostically active nuclide, preferably a diagnostically active radionuclide, or a therapeutically active nuclide, preferably a therapeutically active radionuclide,
Acceptor comprises an aromatic moiety, wherein the aromatic moiety is selected from the group comprising indole and benzene, preferably benzene is substituted with at least one heteroatom, wherein the heteroatom is selected from the group comprising O, N and S, and
Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 72

The compound of any one of embodiments 1, 2, 3, 29, 30, 31, 32, 33, 34, 35, 36, 37, 38, 39, 40, 41, 42, 56, 57, 58, 59, 60, 61, 62, 63, 64, 65, 66, 67, 68, 69, 70 and 71, preferably any one of embodiments 29 and 30, wherein $R^3$, $R^4$ and $R^5$ are each and independently methyl under the proviso that one of $R^3$, $R^4$ and $R^5$ is of the following formula (II):

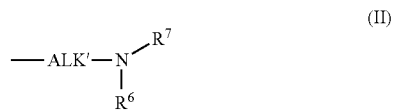

(II)

wherein

ALK' is ($C_2$-$C_5$)alkylidene; and $R^6$ is selected from the group consisting of hydrogen and methyl.

Embodiment 73

The compound of any one of embodiments 1, 2 and 3, wherein $R^1$ is methyl;

AA-COOH is an amino acid selected from the group consisting of 2-amino-2-adamantane carboxylic acid and cyclohexylglycine; and $R^2$ is isopropyl.

Embodiment 74

The compound of any one of embodiments 1, 2, 3 and 73, wherein $R^1$ is methyl;

AA-COOH is an amino acid selected from the group consisting of 2-amino-2-adamantane carboxylic acid and cyclohexylglycine;

$R^2$ is isopropyl;

$R^3$, $R^4$ and $R^5$ are each and independently methyl under the proviso that one of $R^3$, $R^4$ and $R^5$ is of the following formula (II)

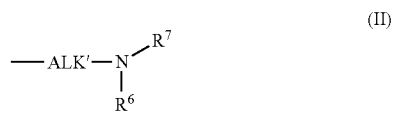

(II)

wherein

ALK' is ($C_2$-$C_5$)alkylidene; and $R^6$ is selected from the group consisting of hydrogen and methyl.

Embodiment 75

The compound of embodiment 74, wherein $R^7$ is Acceptor and one of $R^3$, $R^4$ and $R^5$ is of formula (IIa):

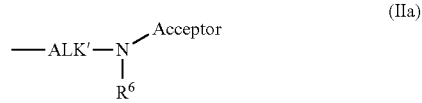

(IIa)

Embodiment 76

The compound of embodiment 75, wherein Acceptor is a chelator.

Embodiment 77

The compound of embodiment 75, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 78

The compound of embodiment 74, wherein $R^7$ is -[Acceptor-Effector] and one of $R^3$, $R^4$ and $R^5$ is of formula (IIb):

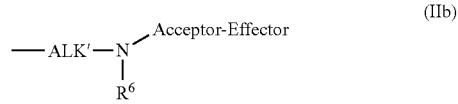

(IIb)

Embodiment 79

The compound of embodiment 78, wherein Acceptor is a chelator and Effector is a diagnostically active nuclide, preferably a diagnostically active radionuclide, or a therapeutically active nuclide, preferably a therapeutically active radionuclide.

Embodiment 80

The compound of embodiment 78, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S, and wherein Effector is a diagnostically active nuclide, preferably a diagnostically active radionuclide, or a therapeutically active nuclide, preferably a therapeutically active radionuclide.

Embodiment 81

The compound of embodiment 74, wherein $R^7$ is -[Linker-Acceptor] and one of $R^3$, $R^4$ and $R^5$ is of formula (IIc):

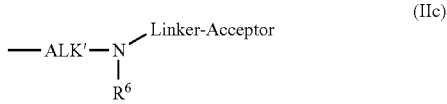

Embodiment 82

The compound of embodiment 81, wherein Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 83

The compound of any one of embodiments 81 and 82, preferably embodiment 82, wherein Acceptor is a chelator.

Embodiment 84

The compound of any one of embodiments 81 and 82, preferably embodiment 82, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 85

The compound of embodiment 74, wherein $R^7$ is -[Linker-Acceptor-Effector] and one of $R^3$, $R^4$ and $R^5$ is of formula (IId):

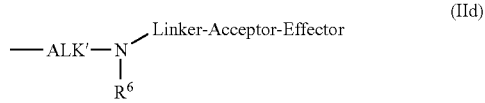

Embodiment 86

The compound of embodiment 85, wherein
Effector is a diagnostically active nuclide, preferably a diagnostically active radionuclide, or a therapeutically active nuclide, preferably a therapeutically active radionuclide,
Acceptor is a chelator, and
Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 87

The compound of embodiment 85, wherein
Effector is a diagnostically active nuclide, preferably a diagnostically active radionuclide, or a therapeutically active nuclide, preferably a therapeutically active radionuclide,
Acceptor comprises an aromatic moiety, wherein the aromatic moiety is selected from the group comprising indole and benzene, preferably benzene is substituted with at least one heteroatom, wherein the heteroatom is selected from the group comprising O, N and S, and
Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 88

The compound of any one of embodiments 1, 2, 3, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86 and, preferably, embodiments 29, 30, 31, 32, 33, 34, 35, 36, 37, 38, 39, 40, 41, 42 and 43, wherein
ALK and ALK' are both propylene, or wherein either ALK is propylene and ALK' is $(C_2-C_5)$alkylidene or ALK is $(C_2-C_5)$alkylidene and ALK' is propylene.

Embodiment 89

The compound according to any one of embodiments 1, 2 and 3, wherein
$R^1$ is methyl;
AA-COOH is an amino acid selected from the group consisting of 2-amino-2-adamantane carboxylic acid and cyclohexylglycine;
$R^2$ is isopropyl; and
ALK and ALK' are both propylene, or wherein either ALK is propylene and ALK' is $(C_2-C_5)$alkylidene or ALK is $(C_2-C_5)$alkylidene and ALK' is propylene.

Embodiment 90

The compound according to embodiment 1, wherein
$R^1$ is methyl;
AA-COOH is an amino acid selected from the group consisting of 2-amino-2-adamantane carboxylic acid and cyclohexylglycine;
$R^2$ is isopropyl;
$R^3$, $R^4$ and $R^5$ are each and independently selected from the group consisting of hydrogen and methyl under the proviso that one of $R^3$, $R^4$ and $R^5$ is of the following formula (II).

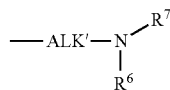
(II)

wherein
R⁶ is selected from the group consisting of hydrogen and methyl; and
ALK and ALK' are both propylene, or wherein either ALK is propylene and ALK' is (C₂-C₅)alkylidene or ALK is (C₂-C₅)alkylidene and ALK' is propylene.

Embodiment 91

The compound according to any one of embodiments 1, 2 and 3, wherein
R¹ is methyl;
AA-COOH is an amino acid selected from the group consisting of 2-amino-2-adamantane carboxylic acid and cyclohexylglycine;
R² is isopropyl;
R³, R⁴ and R⁵ are each and independently methyl under the proviso that one of R³, R⁴ and R⁵ is of the following formula (II):

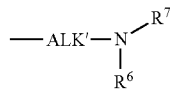
(II)

wherein
R⁶ is methyl;
ALK and ALK' are both propylene, or wherein either ALK is propylene and ALK' is (C₂-C₅)alkylidene or ALK is (C₂-C₅)alkylidene and ALK' is propylene; and
R⁷ is selected from the group comprising Acceptor, -[Acceptor-Effector], -[Linker-Acceptor], and -[Linker-Acceptor-Effector].

Embodiment 92

The compound of embodiment 91, wherein R⁷ is Acceptor and one of R³, R⁴ and R⁵ is of formula (IIa):

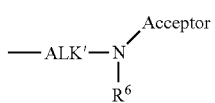
(IIa)

Embodiment 93

The compound of embodiment 92, wherein Acceptor is a chelator.

Embodiment 94

The compound of embodiment 92, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 95

The compound of embodiment 91, wherein R⁷ is -[Acceptor-Effector] and one of R³, R⁴ and R⁵ is of formula (IIb):

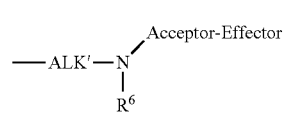
(IIb)

Embodiment 96

The compound of embodiment 95, wherein Acceptor is a chelator and Effector is a diagnostically active nuclide, preferably a diagnostically active radionuclide, or a therapeutically active nuclide, preferably a therapeutically active radionuclide.

Embodiment 97

The compound of embodiment 95, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S, and wherein Effector is a diagnostically active nuclide, preferably a diagnostically active radionuclide, or a therapeutically active nuclide, preferably a therapeutically active radionuclide.

Embodiment 98

The compound of embodiment 91, wherein R⁷ is -[Linker-Acceptor] and one of R³, R⁴ and R⁵ is of formula (IIc):

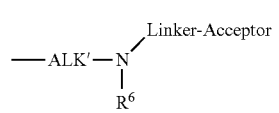
(IIc)

Embodiment 99

The compound of embodiment 98, wherein Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 100

The compound of any one of embodiments 98 and 99, preferably embodiment 99, wherein Acceptor is a chelator.

Embodiment 101

The compound of any one of embodiments 98 and 99, preferably embodiment 99, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 102

The compound of embodiment 91, wherein $R^7$ is -[Linker-Acceptor-Effector] and one of $R^3$, $R^4$ and $R^5$ is of formula (IId):

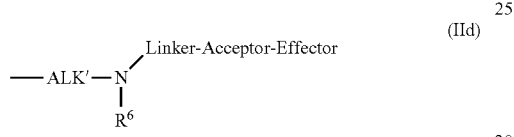

(IId)

Embodiment 103

The compound of embodiment 102, wherein

Effector is a diagnostically active nuclide, preferably a diagnostically active radionuclide, or a therapeutically active nuclide, preferably a therapeutically active radionuclide, Acceptor is a chelator, and Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 104

The compound of embodiment 102, wherein

Effector is a diagnostically active nuclide, preferably a diagnostically active radionuclide, or a therapeutically active nuclide, preferably a therapeutically active radionuclide, Acceptor comprises an aromatic moiety, wherein the aromatic moiety is selected from the group comprising indole and benzene, preferably benzene is substituted with at least one heteroatom, wherein the heteroatom is selected from the group comprising O, N and S, and Linker is a moiety which covalently links the N atom of the group of formula (II) with the Acceptor wherein the type of covalent linkage between the Linker and the N atom of the group of formula (II) is selected from the group comprising amide, urea, thiourea and alkylamine; and the type of covalent linkage between the Linker and the Acceptor is selected from the group comprising amide, alkylamine, urea, ether, thioether, thiourea and carbamate.

Embodiment 105

The compound of any one of embodiments 1 to 104 under the proviso that the compound comprises Effector and Effector is a chelator, wherein Effector is a chelator selected from the group consisting of DOTA, NOTA, DTPA, TETA, EDTA, NODAGA, NODASA, TRITA, CDTA, BAT, DFO, or HYNIC, preferably the chelator is DOTA.

Embodiment 106

The compound of any one of embodiments 1 to 105, wherein the compound is selected from the group consisting of a compound of formula (III), a compound of formula (IIIa), a compound of formula (IIIb), a compound of formula (IIIc), a compound of formula (IIId), a compound of formula (IIIe), a compound of formula (IIIf), a compound of formula (IIIg), a compound of formula (IV), a compound of formula (IVa), a compound of formula (IVb), a compound of formula (V), a compound of formula (Va) and a compound of formula (Vb), wherein the compound of formula (III) is

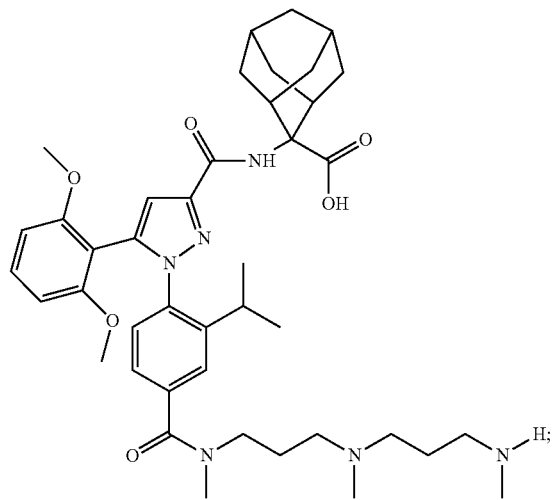

(III)

the compound of formula (IIIa) is
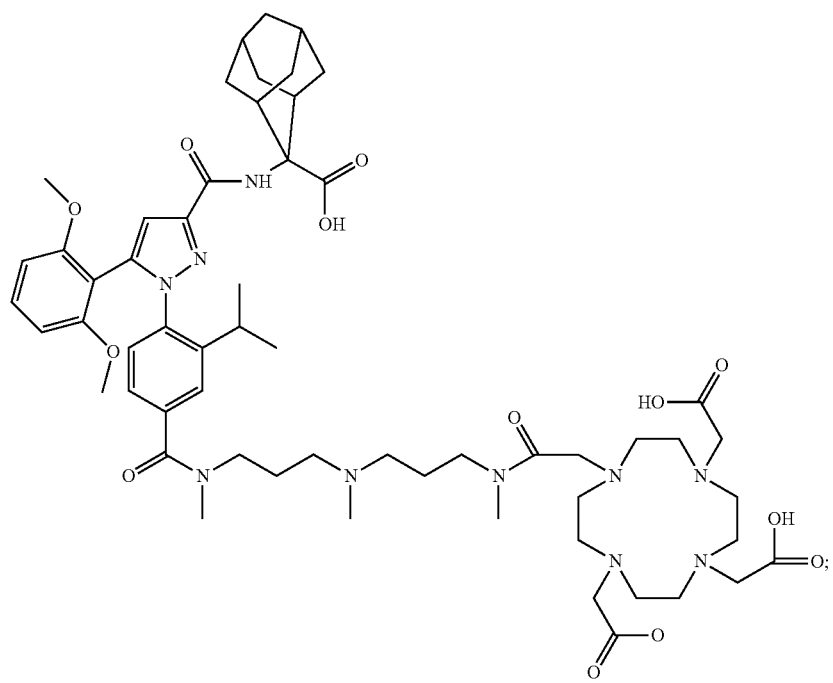
(IIIa)
the compound of formula (IIIb) is
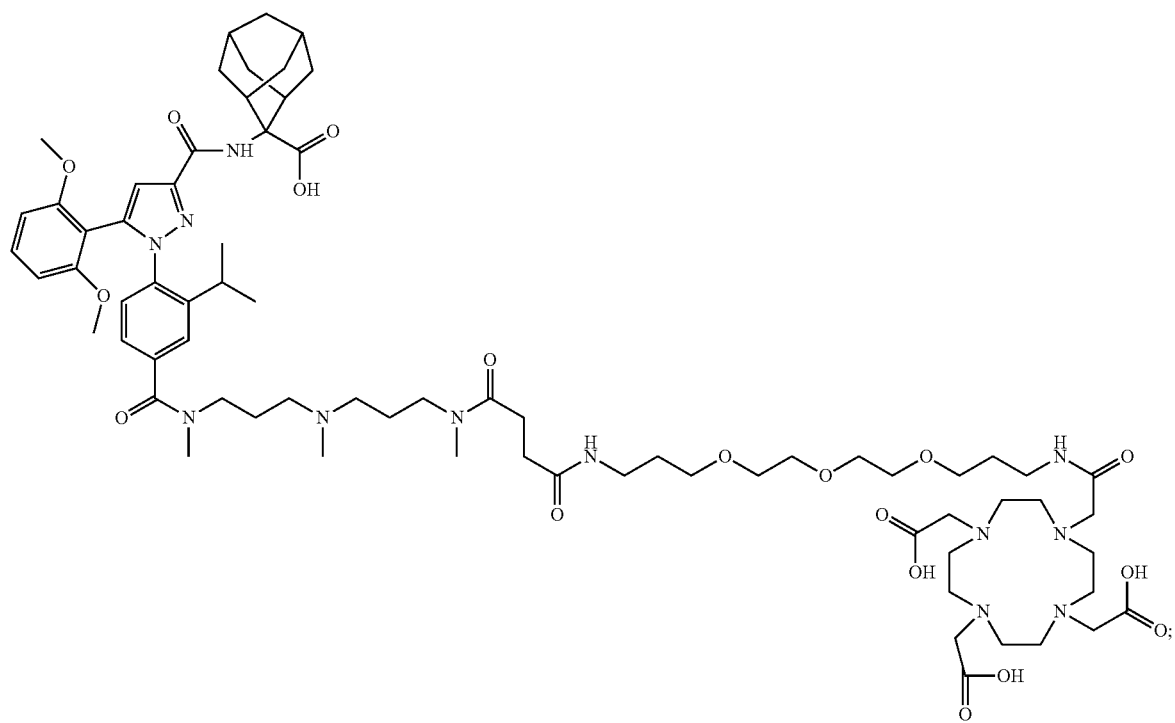
(IIIb)

the compound of formula (IIIc) is
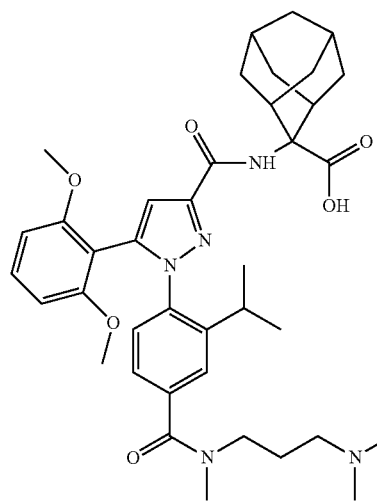
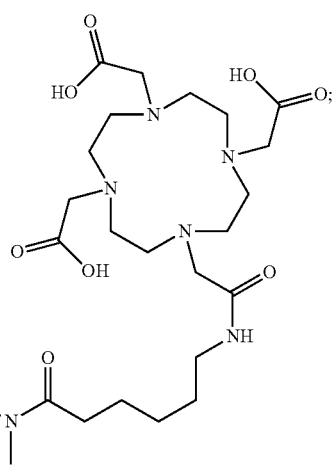
(IIIc)
the compound of formula (IIId) is
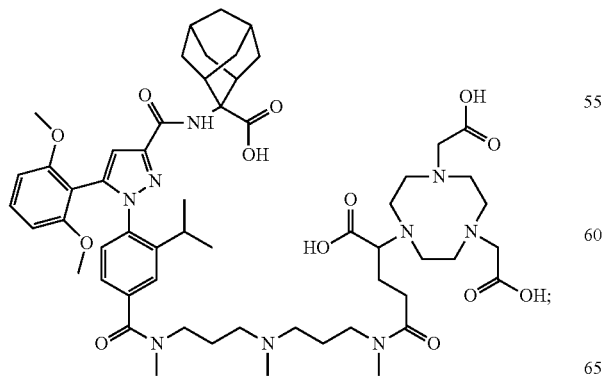
(IIId)

the compound of formula (IIIe) is
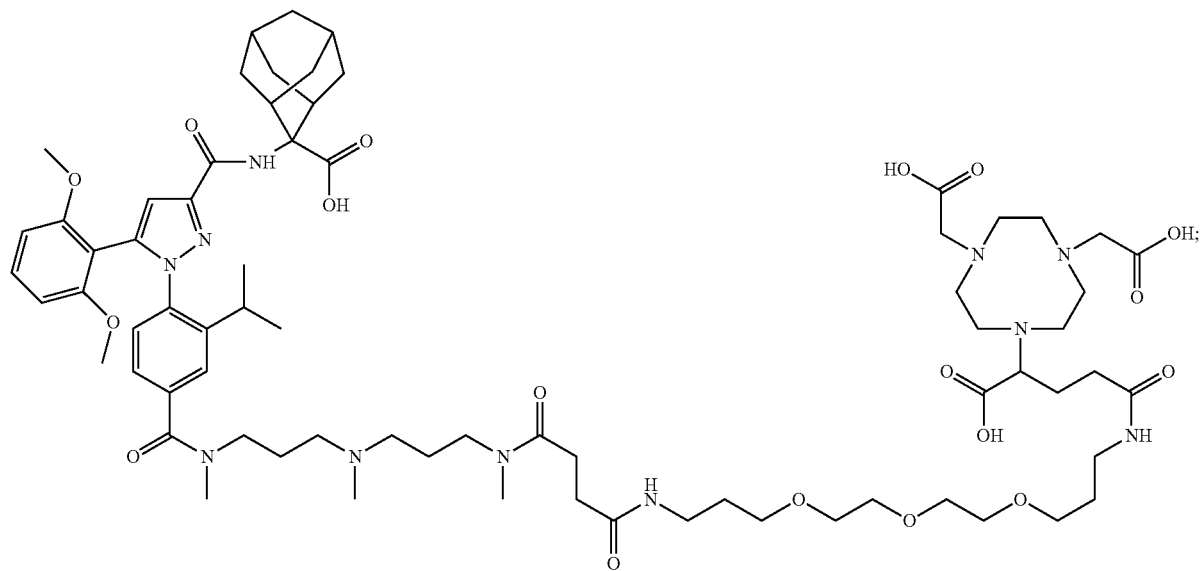
(IIIe)
the compound of formula (IIIf) is
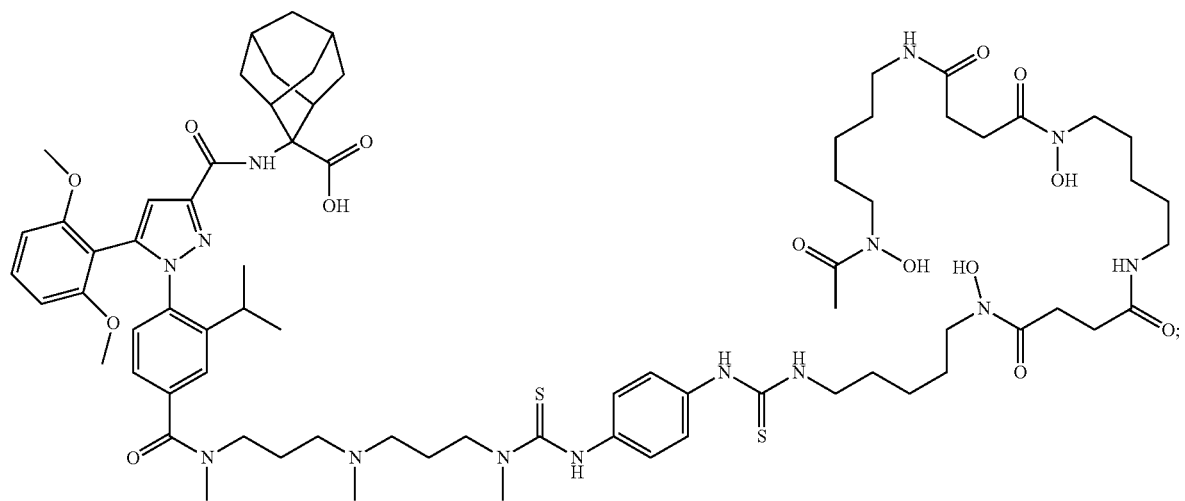
(IIIf)

the compound of formula (IIIg) is
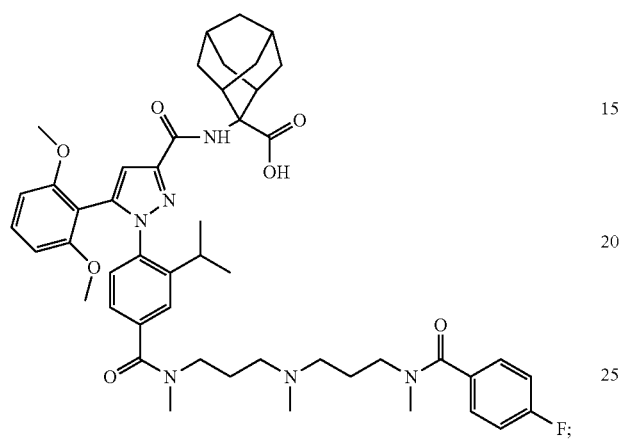
(IIIg)
the compound of formula (IV) is
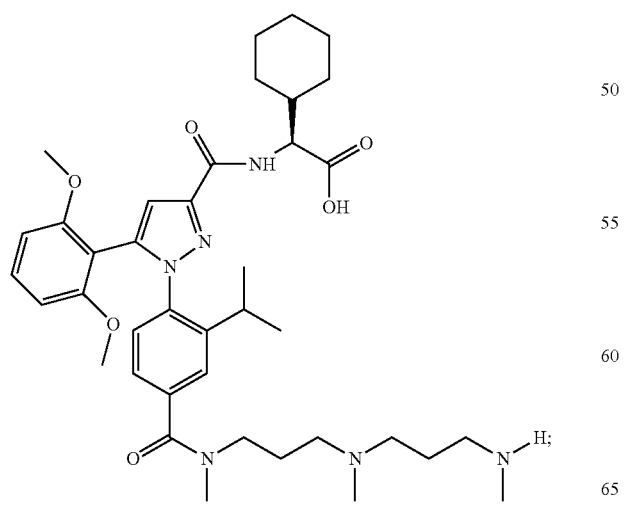
(IV)

the compound of formula (IVa) is
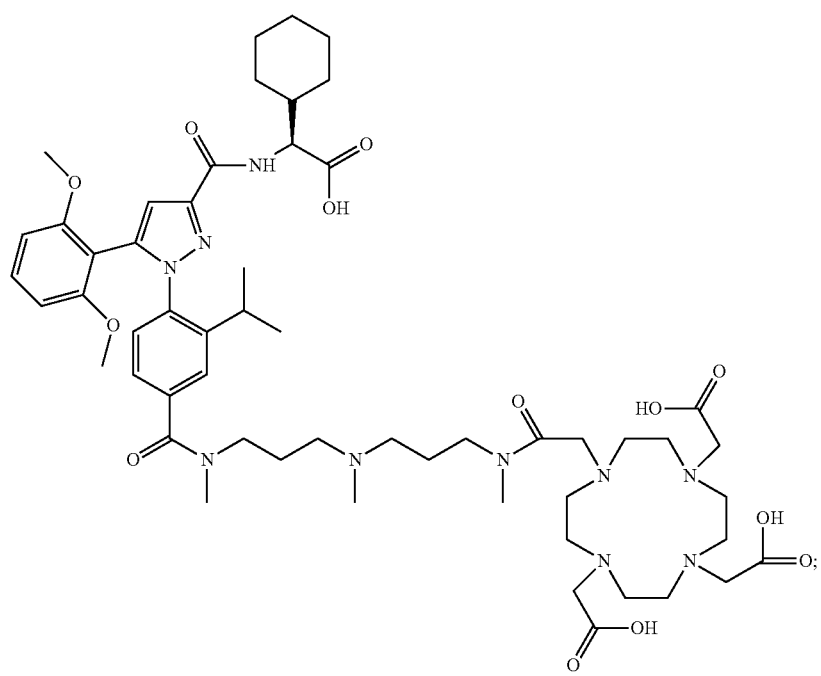
the compound of formula (IVb) is
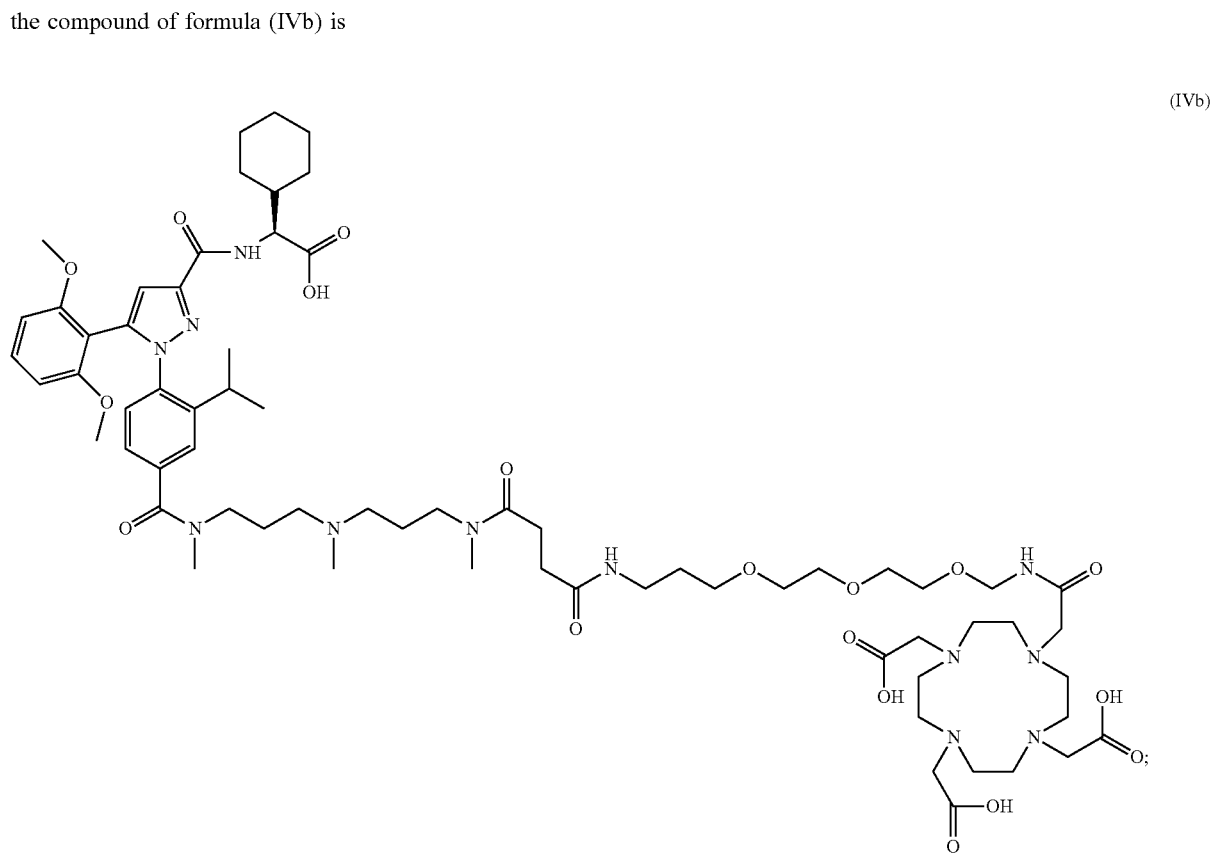

the compound of formula (V) is
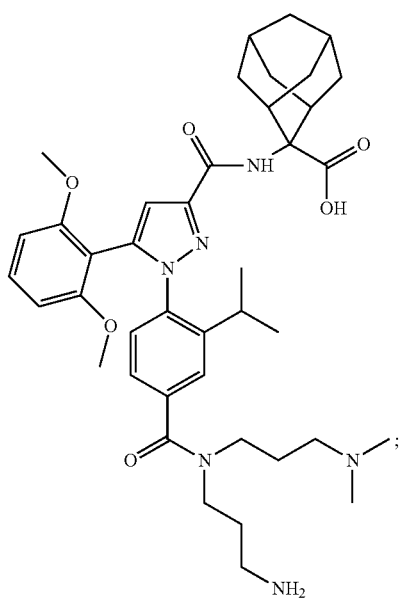
(V)
the compound of formula (Va) is
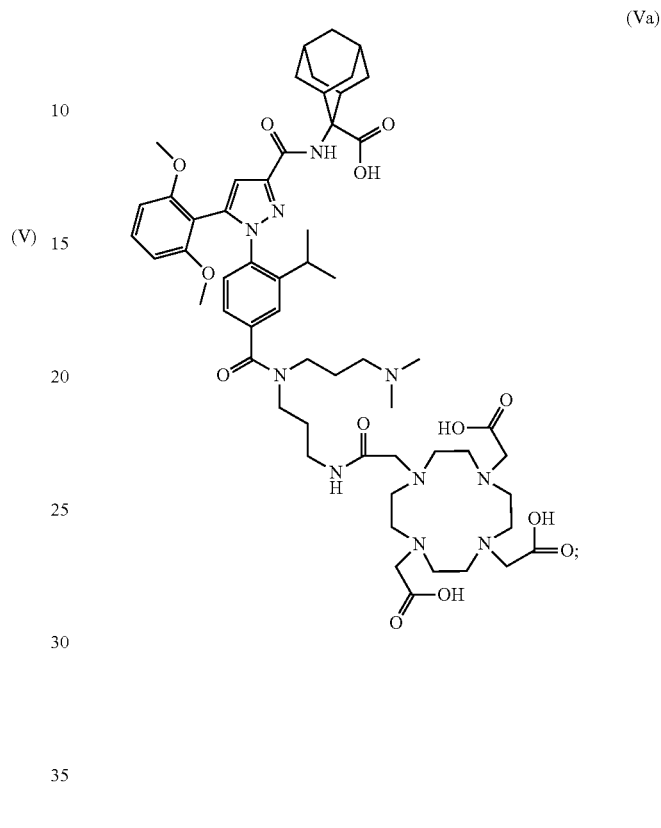
(Va)
and the compound of formula (Vb) is
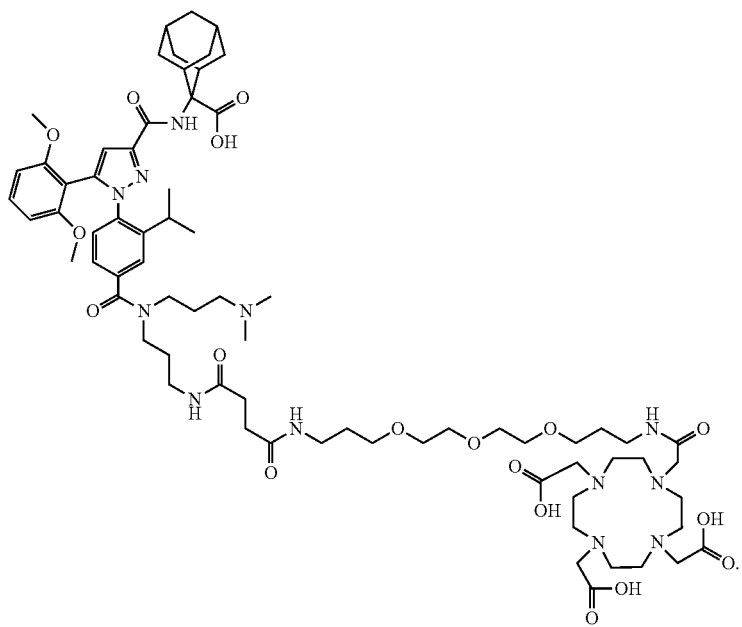
(Vb)

Embodiment 107

The compound of embodiment 106, wherein the compound comprises a diagnostically active nuclide, preferably a diagnostically active radionuclide or a therapeutically active nuclide, preferably a therapeutically active radionuclide.

Embodiment 108

The compound of embodiment 107, wherein the diagnostically active nuclide or the therapeutically active radionuclide is chelated by the chelator of any one of formulae (IIIa), (IIIb), (IIIc), (IVa), (IVb), (Va) and (Vb).

Embodiment 109

The compound of embodiment 108, wherein the diagnostically active radionuclide and the therapeutically active radionuclide is individually and independently chelated by the chelator of formula (IIIa); preferably the diagnostically active radionuclide and the therapeutically active radionuclide is individually and independently selected from the group comprising $^{111}$In, $^{177}$Lu, $^{89}$Zr, $^{67}$Ga, $^{68}$Ga, $^{64}$Cu and $^{90}$Y.

Embodiment 110

The compound of any one of embodiments 1 to 109, wherein the compound interacts with a neurotensin receptor, wherein the neurotensin receptor is preferably selected from the group comprising neurotensin receptor 1 (NTR1) and neurotensin receptor 2 (NTR2).

Embodiment 111

The compound of embodiment 110, wherein the compound is an antagonist of the neurotensin receptor 1.

Embodiment 112

The compound of any one of embodiments 1 to 111, wherein the compound has an $IC_{50}$ of 100 nM or less, preferably 50 nM or less.

Embodiment 113

The compound of any one of embodiments 1 to 112, for use in a method for the diagnosis of a disease.

Embodiment 114

The compound of embodiment 113, wherein the disease is a disease involving neurotensin receptor, preferably the disease is a disease involving neurotensin receptor 1.

Embodiment 115

The compound of embodiment 114, wherein the disease is a disease not involving tissue of the central nervous system and/or cells of the central nervous system.

Embodiment 116

The compound of any one of embodiments 113 to 115, wherein the disease is selected from the group comprising tumors and hematological malignancies.

Embodiment 117

The compound of embodiment 116, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma and Ewing's sarcoma.

Embodiment 118

The compound of any one of embodiments 113 to 117, wherein Effector is a radioactive metal, wherein preferably the radioactive metal is chelated by Acceptor, wherein Acceptor is a chelator.

Embodiment 119

The compound of embodiment 118, wherein the radioactive metal is a diagnostically effective radioactive metal.

Embodiment 120

The compound of embodiment 119, wherein the radioactive metal is selected from the group comprising $^{113m}$In, $^{99m}$Tc, $^{67}$Ga, $^{52}$Fe, $^{68}$Ga, $^{72}$As, $^{111}$In, $^{97}$Ru, $^{203}$Pb, $^{62}$Cu, $^{64}$Cu, $^{51}$Cr, $^{52m}$Mn, $^{157}$Gd, $^{64}$Cu, $^{89}$Zr, and $^{177}$Lu; more preferably the radioactive metal is selected from the group comprising $^{99m}$Tc, $^{67}$Ga, $^{68}$Ga, $^{111}$In, $^{89}$Zr and $^{177}$Lu; and more preferably the radioactive metal is $^{111}$In, $^{177}$Lu or $^{89}$Zr.

Embodiment 121

The compound of any one of embodiments 113 to 117, wherein Effector is a radionuclide, wherein preferably the radionuclide is covalently bound by Acceptor, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 122

The compound of embodiment 121, wherein the radionuclide is a diagnostically effective radioactive halogen.

Embodiment 123

The compound of embodiment 122, wherein the radioactive halogen is selected from the group comprising $^{18}$F, $^{123}$I, $^{124}$I, $^{125}$I, $^{131}$I, $^{75}$Br, $^{76}$Br, $^{77}$Br, $^{82}$Br and $^{211}$At; more preferably the radionuclide is selected from the group comprising $^{123}$I, $^{124}$I.

Embodiment 124

The compound of any one of embodiments 113 to 123, wherein the method for the diagnosis is an imaging method.

Embodiment 125

The compound of embodiment 124, wherein the imaging method is selected from the group consisting of scintigraphy, Single Photon Emission Computed Tomography (SPECT) and Positron Emission Tomography (PET).

Embodiment 126

The compound of any one of embodiments 113 to 125, wherein the method comprises the administration of a diagnostically effective amount of the compound to a subject, preferably to a mammal, wherein the mammal is selected from the group comprising man, companion animals, pets and livestock, more preferably the subject is selected from the group comprising man, dog, cat, horse and cow, and most preferably the subject is a human being.

Embodiment 127

The compound of any one of embodiments 1 to 113, for use in a method for the treatment of a disease.

Embodiment 128

The compound of embodiment 127, wherein the disease is a disease involving neurotensin receptor, preferably the disease is a disease involving neurotensin receptor 1.

Embodiment 129

The compound of embodiment 128, wherein the disease is a disease not involving tissue of the central nervous system and/or cells of the central nervous system.

Embodiment 130

The compound of any one of embodiments 127 to 128, wherein the disease is selected from the group comprising tumors and hematological malignancies.

Embodiment 131

The compound of embodiment 130, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma and Ewing's sarcoma.

Embodiment 132

The compound of any one of embodiments 129 to 131, wherein Effector is a therapeutically active agent.

Embodiment 133

The compound of any one of embodiments 127 to 132, wherein the method comprises the administration of a therapeutically effective amount of the compound to a subject, preferably to a mammal, wherein the mammal is selected from the group comprising man, companion animals, pets and livestock, more preferably the subject is selected from the group comprising man, dog, cat, horse and cow, and most preferably the subject is a human being.

Embodiment 134

The compound of any one of embodiments 127 to 131, wherein Effector is a radioactive metal, wherein preferably the radioactive metal is chelated by Acceptor, wherein Acceptor is a chelator.

Embodiment 135

The compound of embodiment 134, wherein the radioactive metal is selected from the group comprising $^{186}$Re, $^{90}$Y, $^{67}$Cu, $^{68}$Ga, $^{69}$Er, $^{121}$Sn, $^{127}$Te, $^{142}$Pr, $^{143}$Pr, $^{198}$Au, $^{199}$Au, $^{161}$Tb, $^{109}$Pd, $^{188}$Rd, $^{188}$Re, $^{77}$As, $^{166}$Dy, $^{166}$Ho, $^{149}$Pm, $^{151}$Pm, $^{153}$Sm, $^{159}$Gd, $^{172}$Tm, $^{90}$Y, $^{111}$In, $^{169}$Yb, $^{175}$Yb, $^{177}$Lu, $^{105}$Rh, $^{111}$Ag, $^{213}$Bi, $^{225}$Ac, $^{64}$Cu, $^{177m}$Sn and $^{227}$Th, preferably the radioactive metal is selected from the group comprising $^{186}$Re, $^{188}$Re, $^{90}$Y, $^{153}$Sm, $^{68}$Ga, and $^{177}$Lu; and more preferably the radioactive metal is selected from the group comprising $^{90}$Y and $^{177}$Lu.

Embodiment 136

The compound of any one of embodiments 127 to 133, wherein Effector is a radionuclide, wherein preferably the radionuclide is covalently bound by Acceptor, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 137

The compound of embodiment 136, wherein the radionuclide is a radioactive halogen.

Embodiment 138

The compound of embodiment 137, wherein the radioactive halogen is selected from the group comprising $^{123}$I, $^{125}$I and $^{129}$I.

Embodiment 139

The compound of any one of embodiments 1 to 112, for use in a method for the identification of a subject, wherein the subject is likely to respond or likely not to respond to a treatment of a disease, wherein the method for the identification of a subject comprises carrying out a method of diagnosis using the compound of any one of embodiments 1 to 110, preferably a method for the diagnosis of a disease as described in any one of embodiments 111 to 124.

Embodiment 140

The compound of any one of embodiments 1 to 112, for use in a method for the selection of a subject from a group of subjects, wherein the subject is likely to respond or likely not to respond to a treatment of a disease, wherein the method for the selection of a subject from a group of subjects comprises carrying out a method of diagnosis using the compound of any one of embodiments 1 to 112, preferably a method for the diagnosis of a disease as described in any one of embodiments 113 to 126.

Embodiment 141

The compound of any one of embodiments 1 to 112, for use in a method for the stratification of a group of subjects into subjects which are likely to respond to a treatment of a disease, and into subjects which are not likely to respond to a treatment of a disease, wherein the method for the stratification of a group of subjects comprises carrying out a method of diagnosis using the compound of any one of embodiments 1 to 112, preferably a method for the diagnosis of a disease as described in any one of embodiments 113 to 126.

Embodiment 142

The compound of any one of embodiments 139 to 141, wherein the disease is a disease involving neurotensin receptor, preferably the disease is a disease involving neurotensin receptor 1.

Embodiment 143

The compound of embodiment 142, wherein the disease is a disease not involving tissue of the central nervous system and/or cells of the central nervous system.

Embodiment 144

The compound of any one of embodiments 139 to 143, wherein the disease is selected from the group comprising tumors and hematological malignancies.

Embodiment 145

The compound of embodiment 144, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma and Ewing's sarcoma.

Embodiment 146

The compound of any one of embodiments 139 to 145, wherein the method of diagnosis is an imaging method.

Embodiment 147

The compound of embodiment 146, wherein the imaging method is selected from the group comprising scintigraphy, Single Photon Emission Computed Tomography (SPECT) and Positron Emission Tomography (PET).

Embodiment 148

The compound of any one of embodiments 139 to 147, preferably any one of embodiments 146 and 147 wherein Effector is a radioactive metal, wherein preferably the radioactive metal is chelated by Acceptor, wherein Acceptor is a chelator.

Embodiment 149

The compound of any one of embodiments 139 to 147, preferably any one of embodiments 146 and 147, wherein Effector is a radioactive halogen, wherein preferably the radioactive halogen is covalently bound by Acceptor, wherein Acceptor comprises an aromatic moiety, wherein the aromatic moiety is selected from the group comprising indole and benzene, preferably benzene is substituted with at least one heteroatom, wherein the heteroatom is selected from the group comprising O, N and S.

Embodiment 150

The compound of any one of embodiments 1 to 112, for use in a method for delivering an effector to neurotensin receptor, preferably neurotensin receptor 1, wherein the effector is selected from the group comprising a diagnostically active agent and a therapeutically active agent.

Embodiment 151

The compound of embodiment 150, wherein the neurotensin receptor is expressed by a cell and/or a tissue, wherein preferably the neurotensin expressing cell and/or neurotensin expressing tissue is different from a cell of the central nervous system and/or tissue of the central nervous system.

Embodiment 152

The compound of any one of embodiments 150 to 151, wherein the NTR1 expressing tissue is NTR1 expressing tissue of a tumor or NTR1 expressing tissue of a hematological malignancy, and wherein the NTR1 expressing cell is a NTR1 expressing tumor cell or an NTR1 expressing hematological malignancy cell.

Embodiment 153

The compound of embodiment 152, wherein the tumor is selected from the group comprising ductal pancreatic adenocarcinoma, small cell lung cancer, prostate cancer, colorectal cancer, breast cancer, meningioma, Ewing's sarcoma, pleural mesothelioma, head and neck cancer, non-small cell lung cancer, gastrointestinal stromal tumors, uterine leiomyoma and cutaneous T-cell lymphoma, preferably ductal pancreatic adenocarcinoma, small cell lung cancer, prostate cancer, colorectal cancer, breast cancer, meningioma and Ewing's sarcoma.

Embodiment 154

The compound of any one of embodiments 139 to 142, wherein the effector is a radionuclide, preferably a metal radioactive or a halogen radioactive, more preferably the effector is Effector of the compound of any one of embodiments 1 to 112.

Embodiment 155

The compound of any one of embodiments 150 to 154, wherein the method comprises the administration of an effective amount of the compound and/or of the effector to a subject, preferably to a mammal, wherein the mammal is selected from the group comprising man, companion animals, pets and livestock, more preferably the subject is selected from the group comprising man, dog, cat, horse and cow, and most preferably the subject is a human being.

Embodiment 156

The compound of any one of embodiments 150 to 155, wherein the delivery is for diagnosis, treatment and/or a combination of diagnosis and treatment.

Embodiment 157

The compound of any one of embodiments 155 to 156, wherein the effective amount is a diagnostically effective amount and/or a therapeutically effective amount.

Embodiment 158

A composition, preferably a pharmaceutical composition, wherein the composition comprises a compound according to any one of embodiments 1 to 112 and a pharmaceutically acceptable excipient.

Embodiment 159

The composition of embodiment 158 for use in any method as defined in any of the preceding embodiments.

Embodiment 160

A method for the diagnosis of a disease in a subject, wherein the method comprises administering to the subject a diagnostically effective amount of a compound according to any one of embodiments 1 to 112.

Embodiment 161

The method of embodiment 160, wherein the compound comprises a diagnostically active agent, whereby the agent is preferably a radionuclide.

Embodiment 162

A method for the treatment of a disease in a subject, wherein the method comprises administering to the subject a therapeutically effective amount of a compound according to any one of embodiments 1 to 112.

Embodiment 163

The method of embodiment 162, wherein the compound comprises a therapeutically active agent, whereby the agent is preferably a radionuclide.

Embodiment 164

The method according to any one of embodiments 160 to 163, wherein the disease is a disease involving neurotensin receptor, preferably the disease is a disease involving neurotensin receptor 1.

Embodiment 165

The method according to any one of embodiments 160 to 163, wherein the disease is selected from the group comprising tumors and hematological malignancies.

Embodiment 166

A kit comprising a compound according to any one of embodiments 1 to 112, one or more optional excipient(s) and optionally one or more device(s), whereby the device(s) is/are selected from the group comprising a labeling device, a purification device, a handling device, a radioprotection device, an analytical device or an administration device.

Embodiment 167

The kit of embodiment 166 for use in any method as defined in any of the preceding embodiments.

It will be acknowledged by a person skilled in the art that a or the compound of the invention is any compound disclosed herein, including but not limited to any compound described in any of the above embodiments and any of the following embodiments.

It will be acknowledged by a person skilled in the art that a or the method of the invention is any method disclosed herein, including but not limited to any method described in any of the above embodiments and any of the following embodiments.

It will be acknowledged by a person skilled in the art that a or the composition of the invention is any composition disclosed herein, including but not limited to any composition described in any of the above embodiments and any of the following embodiments.

It will be acknowledged by a person skilled in the art that a or the kit of the invention is any kit disclosed herein, including but not limited to any kit described in any of the above embodiments and any of the following embodiments.

The present invention is based on the surprising finding of the present inventors that the compound of the invention is not only binding to NTR1 with a high affinity, but is also not crossing the blood-brain barrier. This characteristic allows the use of the compound of the invention in the diagnosis as well as in the treatment of diseases such as, but not limited to, tumors, particularly tumors different from tumors of the central nervous system in its various forms, more particularly those forms thereof which require passage of the diagnostically and/or therapeutically effective agent across the blood-brain barrier. Along with this characteristics go a high and persistent uptake by tumors and NTR1 expressing tumors in particular as well as NTR1 expressing hematological malignancies, combined with a low uptake and rapid clearance in non-target organs thus providing an excellent tumor-to-background ratio. Using the compound of the invention the tumor-to-background ratio is at least 1.5, preferably greater than 2, and more preferably greater than 5. The tumor-to-background ratio is preferably defined as the signal intensity of the tumor divided by the background signal intensity. Signal intensities are typically measured with a region-of-interest (ROI) analysis of the tumor and ROI analysis of surrounding healthy tissue as background (see Palmedo et al., *Nucl Med Biol*, 2002, 29, 809-815).

Finally, the present inventors have surprisingly found that the modification of the compound of the invention such as, for example, by covalently linking a chelator will result in a significantly reduced binding characteristic of the thus modified compound of the invention to NTR1 if the modification is made at a position which a person skilled in the art understands as being chemically most simple and thus suitable for such modification, namely substituent AA-COOH of the compound of the invention.

A still further characteristic of the compound of the invention is its weak binding to NTR2 which is predominantly expressed in the central nervous system (CNS). Such weak binding to NTR2 of the compound of the invention either as such or if conjugated to a diagnostically and/or therapeutically active effector, is insofar advantageous as less side effects are observed which would otherwise arise from a less discriminating or more promiscuous binding of the compound of the invention to neurotensin receptors and NTR1 and NTR2 in particular.

The compound of the invention is an antagonist to NTR1. The suitability of an antagonist to NTR1 for use in the diagnosis and/or therapy of diseases and diseases involving NTR1 expressing cells and NTR1 expressing tissue in particular, is a surprising finding. The prevailing understanding in the art is that in order to provide a suitable means for diagnosis and/or therapy of such diseases an agonist to NTR1 is to be used, particularly if the diagnostically active agent or the therapeutically active agent, generally referred to as effector, is a radiolabel such as a radionuclide. The rationale behind this understanding in the art is that an effective in vivo diagnosis and therapy, particular in case such diagnosis and therapy makes use of a radiolabel such as a radionuclide attached to a compound having an affinity to a target molecule such as a receptor, requires that such compound shows good internalization properties leading to a high in vivo accumulation and retention of the compound and thus of the effector in the tissue and cells, respectively, expressing the target molecule. As well-known from molecular-pharmacologic investigations efficient internalization is usually provided predominantly by agonists (Bodei et al., *J. Nucl. Med.*, 2006, 47, 375-377; Koenig et al., *Trends Pharmacol. Sci.*, 1997, 18, 276-287; Cescato et al., *J. Nucl. Med.*, 2006, 47, 502-511; Ginj et al., *Proc. Natl. Acad. Sci. USA*, 2006, 103, 16436-16441) thus suggesting the use of target molecule agonists rather than target molecule antagonists. In accordance therewith and as evident from the prior art recited above, the compound suitable for use in the diagnosis and/or therapy of a disease whereby the disease involves NTR1 expressing cells and NTR1 expressing tissue, respectively, is to produce or elicit a diagnostic or therapeutic effect by NTR1 upon interaction with NTR1, whereby the compound is subsequently internalized into NTR1 expressing cells. Because of this, this kind of compound of the prior art acts as an agonist to NTR1. Such internalization preferably occurs by means of endycytosis. In contrast thereto, an antagonist to NTR1 as the compound of the invention counteracts the effect of an agonist to NTR1 and is preferably not internalized into NTR1 expressing cells. In connection therewith it is noteworthy that the present inventors found that the compound of the invention surprisingly binds to a higher number of binding sites compared to an agonist of comparable binding affinity.

The compounds of the invention differ from the prior art and U.S. Pat. No. 5,723,483 in particular by group (II)

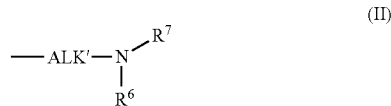

(II)

which can be attached at different positions in a compound of the invention of formula (I). As outlined herein, the compounds of the invention are potent NTR1 antagonists showing superior characteristics. This applies to the compounds of the invention regardless of whether $R^7$ is hydrogen or an Effector moiety. For example, compounds of formulae (III) and (V) where $R^7$ is H, were active with single digit nanomolar IC50 values in both the functional Ca-mobilisation assay and the radioligand binding assay as shown in the example part.

A further finding underlying the present invention is, as shown in the example part, that in case $R^7$ is an Effector moiety and thus different from hydrogen, such Effector moiety does not have an impact on the overall binding characteristics of the compounds of the invention, at least not to such extent which would render the binding of the compounds of the invention unspecific such as, preferably resulting in an IC50 value greater than 10 μM or which would not allow the use of the compound of the invention in the various methods disclosed herein and in particular methods for the treatment and/or prevention of a disease as defined herein and methods for the diagnosis of a disease as defined herein. Insofar, $R^7$ is a moiety which does not seem to interfere with the binding of the compound of the invention to NTR1. Because of this, the effector moiety represented by $R^7$ in the compound of the invention can vary in a broad manner as is evident from the example part.

As disclosed herein in more detail, an Effector moiety is a moiety which comprises or is capable of comprising an Effector, whereby the Effector is preferably selected from the group consisting of a diagnostically active agent, a therapeutically active agent, an agent which is suitable as both a diagnostically active agent and a therapeutically active agent, and a combination of a diagnostically active agent and a therapeutically active agent. In other words, an Effector moiety can be an effector which is already complexed by or covalently bound to the compound of formula (I), whereby such complexing or binding is realized with $R^7$ being a structure of [Acceptor-Effector] or of [Linker-Acceptor-Effector]). Alternatively, the compound of the invention is capable of reacting readily with an Effector, whereby in such case $R^7$ is a structure of [Acceptor] or of [Linker-Acceptor]). In both cases, the Linker is an optional element and the Acceptor, preferably, is a moiety, e.g. a chelator, which "accepts" the Effector.

Using a structurally diverse set of Linkers and/or Acceptors in compounds where $R^7$ was either [Linker-Acceptor] or [Acceptor], it was demonstrated that these moieties act independently and all of them yield very attractive and highly similar NTR1 affinities as shown in the example art and the NTR1 assays in particular. More specifically, starting from compound of formula (III) various compounds were prepared all of which contained a DOTA-moiety as Acceptor; however compound of formula (IIIa) contained no Linker, compound of formula (IIIc) contained Ahx, a medium size, hydrophobic spacer as Linker and compound of formula (IIIb) contained Ttds as Linker which is more hydrophilic and can span approximately twice the distance of Ahx. All compounds with Linker moieties of different size and properties displayed high affinity to NTR1 (Ca IC50 between 12 and 20 nM and RLB IC50 between 3 and 6 nM). Thus, a wide range of Linkers is acceptable which is insofar surprising as a person skilled in the art would have expected that the use of a Linker moiety is obligatory for preserving NTR1 binding. As a matter of fact, a person skilled in the art would have expect that in compounds of the invention without Linker the Acceptor or Acceptor-Effector might interfere with the NTR1 binding part of the compound. However, these Effector moieties act independently from the NTR1 binding part of the molecules as demonstrated by these examples.

Similar experiments were carried out using a different Acceptor, namely NODAGA, with a different ring size compared to DOTA. In these experiments, compound of formula (IIIe) comprising Ttds as a Linker was compared to compound of formula (IIId) not comprising any Linker. Again, the affinities of both compounds were very high and similar to each other, as well as very similar to the corresponding compounds from the DOTA-series (and more specifically compound of formula (IIIb) and compound of formula (IIIa)).

Finally, a totally different Acceptor was tested as realized in compound of formula (IIIf). DFO as linear Acceptor was selected in combination with a rigid para-substituted aromatic Linker, in this case linked at both ends via a thiourea functionality to the Acceptor and to the nitrogen of formula of formula (II). The affinities were again very high and similar to the ones of compounds having different types of [Linker-Acceptor]moieties and [Acceptor] moieties (Ca IC50 17.5 and RLB IC50 3 nM).

Furthermore, it has been demonstrated by respective experiments that the above is true irrespective of whether the group of formula (II) represents $R^4$ and $R^5$, respectively, which are equivalent from a chemical point of view, or $R^3$.

That the NTR1 binding property of the compound of the invention is mainly determined by the choice of substituents in the NTR1 binding part, has been shown by modifying compound of formula (IIIa) as to its NTR1 binding part. More specifically, 2-amino-adamantane carboxylic acid in compound of formula (IIIa) has been replaced by cyclohexylglycine resulting in compound of formula (IVa). Both compound of formula (IIIa) and compound of formula (IVa) contain no Linker and DOTA as Acceptor.

Experimental evidence is also available confirming that the Effector does not have an impact on NTR1 binding of the compounds of the invention to an extent which does not allow their use as disclosed herein. More specifically, compound of formula (IIIa) was complexed with In, Ga, Y and Lu. Surprisingly, all complexes exhibited improved affinities compared to the corresponding compounds without Effector (Ca IC50 between 5 and 7 nM and RLB IC50 between 0.6 and 1.2 nM). Accordingly, a variety of differently sized metals is well tolerated and all have very similar and attractive affinities. Similar trends in terms of improvement of affinity after metal complexation were observed for other metal complexes such as Lu complexes in case of compound of formula (IIIb) (Lu-(IIIb)), Ga complexes in case of compound of formula (IIId) (Ga-(IIId)), In complexes in case of compound of formula (IVa) (In-(IVa)) and In complexes in case of compound of formula (Va) (In-(Va)). Also, the Zirconium-complex of compound of formula (IIIf) (Zr-(IIIf)) showed the same NTR1 affinity as the uncomplexed compound of formula (IIIf). Finally, also compound of formula (IIIg) where a halogen (F) as Effector is covalently bound to an aromate (benzoic acid) without any Linker showed an affinity within a typical range (Ca IC50 14.5 and RLB IC50 2 nM).

The expression alkyl as preferably used herein refers each and individually to a saturated, straight-chain or branched hydrocarbon group and is usually accompanied by a qualifier which specifies the number of carbon atoms it may contain. For example the expression $(C_1-C_6)$alkyl means each and individually any of methyl, ethyl, n-propyl, isopropyl, n-butyl, isobutyl, sec-butyl, tert-butyl, n-pentyl, 1-methyl-butyl, 1-ethyl-propyl, 3-methyl-butyl, 1,2-dimethyl-propyl, 2-methyl-butyl, 1,1-dimethyl-propyl, 2,2-dimethylpropyl, n-hexyl, 1,1-dimethyl-butyl and any other isoform of alkyl groups containing six saturated carbon atoms.

In an embodiment and as preferably used herein, $(C_1-C_4)$ alkyl means each and individually any of methyl, ethyl, n-propyl, isopropyl, n-butyl, isobutyl, sec-butyl and tert-butyl.

In an embodiment and as preferably used herein, $(C_2-C_5)$ alkyl means each and individually any of ethyl, n-propyl, isopropyl, n-butyl, isobutyl, sec-butyl, tert-butyl, n-pentyl, 1-methyl-butyl, 1-ethyl-propyl, 3-methyl-butyl, 1,2-dimethyl-propyl, 2-methyl-butyl, 1,1-dimethyl-propyl and 2,2-dimethylpropyl.

In an embodiment and as preferably used herein, $(C_1-C_5)$ alkyl means each and individually any of methyl, ethyl, n-propyl, isopropyl, n-butyl, isobutyl, sec-butyl, tert-butyl, n-pentyl, 1-methyl-butyl, 1-ethyl-propyl, 3-methyl-butyl, 1,2-dimethyl-propyl, 2-methyl-butyl, 1,1-dimethyl-propyl and 2,2-dimethylpropyl.

In an embodiment and as preferably used herein, $(C_1-C_6)$ alkyl means each and individually any of methyl, ethyl, n-propyl, isopropyl, n-butyl, isobutyl, sec-butyl, tert-butyl, n-pentyl, 1-methyl-butyl, 1-ethyl-propyl, 3-methyl-butyl, 1,2-dimethyl-propyl, 2-methyl-butyl, 1,1-dimethyl-propyl, 2,2-dimethylpropyl, n-hexyl, 1-methyl-pentyl, 1-ethyl-butyl, 4-methyl-pentyl, 1,3-dimethyl-butyl, 1-ethyl-2-methyl-propyl, 1,1-dimethyl-butyl, 2-methyl-pentyl, 3-methyl-pentyl, 1,2-dimethyl-butyl, 1-ethyl-1-methyl-propyl, 2,3-dimethyl-butyl, 1,1,2-trimethyl-propyl, 3,3-dimethyl-butyl, 1,2,2-trimethyl-propyl and 2,2-dimethyl-butyl.

In an embodiment and as preferably used herein, $(C_3-C_6)$ alkyl means each and individually any of n-propyl, isopropyl, n-butyl, isobutyl, sec-butyl, tert-butyl, n-pentyl, 1-methyl-butyl, 1-ethyl-propyl, 3-methyl-butyl, 1,2-dimethyl-propyl, 2-methyl-butyl, 1,1-dimethyl-propyl, 2,2-dimethylpropyl, n-hexyl, 1-methyl-pentyl, 1-ethyl-butyl, 4-methyl-pentyl, 1,3-dimethyl-butyl, 1-ethyl-2-methyl-propyl, 1,1-dimethyl-butyl, 2-methyl-pentyl, 3-methyl-pentyl, 1,2-dimethyl-butyl, 1-ethyl-1-methyl-propyl, 2,3-dimethyl-butyl, 1,1,2-trimethyl-propyl, 3,3-dimethyl-butyl, 1,2,2-trimethyl-propyl and 2,2-dimethyl-butyl.

The expression alkylidene as preferably used herein refers to a saturated straight chain or branched hydrocarbon group wherein two points of substitution are specified. Simple alkyl chains wherein the two points of substitutions are in a maximal distance to each other like ethane-1,2-diyl, propane-1,3-diyl, butane-1,4-diyl and pentane-1,5-diyl are also referred to as ethylene (which is also referred to as ethane-1,2-diyl), propylene (which is also referred to as propane-1,3-diyl), butylene (which is also referred to as butane-1,4-diyl) and pentylene (which is also referred to as pentane-1,5-diyl).

In an embodiment and as preferably used herein, $(C_1-C_4)$ alkylidene means each and individually any of methylene, ethane-1,2-diyl, propane-1,3-diyl, propane-1,2-diyl, butane-1,4-diyl, butane-1,3-diyl, butane-1,2-diyl, 2-methyl-propane-1,2-diyl and 2-methyl-propane-1,3-diyl.

In an embodiment and as preferably used herein, $(C_2-C_5)$ alkylidene means each and individually any of ethane-1,2-diyl, propane-1,3-diyl, propane-1,2-diyl, butane-1,4-diyl, butane-1,3-diyl, butane-1,2-diyl, 2-methyl-propane-1,2-diyl, 2-methyl-propane-1,3-diyl, pentane-1,5-diyl, pentane-1,4-diyl, pentane-1,3-diyl, pentane-1,2-diyl, pentane-2,3-diyl, pentane-2,4-diyl and any other branched isomer with 5 carbon atoms, preferably $(C_2-C_5)$alkylidene means each and individually any of ethane-1,2-diyl, propane-1,3-diyl, butane-1,4-diyl and pentane-1,5-diyl.

In an embodiment and as preferably used herein, $(C_2-C_{10})$alkylidene means each and individually any of ethane-1,2-diyl, propane-1,3-diyl, propane-1,2-diyl, butane-1,4-diyl, butane-1,3-diyl, butane-1,2-diyl, 2-methyl-propane-1,2-diyl, 2-methyl-propane-1,3-diyl, pentane-1,5-diyl, pentane-1,4-diyl, pentane-1,3-diyl, pentane-1,2-diyl, pentane-2,3-diyl, pentane-2,4-diyl, any other isomer with 5 carbon atoms, hexane-1,6-diyl, any other isomer with 6 carbon atoms, heptane-1,7-diyl, any other isomer with 7 carbon atoms, octane-1,8-diyl, any other isomer with 8 carbon atoms, nonane-1,9-diyl, any other isomer with 9 carbon atoms, decane-1,10-diyl and any other isomer with 10 carbon atoms, preferably $(C_2-C_{10})$alkylidene means each and individually any of ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl and decane-1,10-diyl.

In an embodiment and as preferably used herein, ($C_3$-$C_5$) cycloalkyl means each and individually any of cyclopropyl, cyclobutyl, cyclopentyl, cyclohexyl, cycloheptyl and cyclooctyl.

In an embodiment and as preferably used herein, ($C_3$-$C_8$) cycloalkylmethyl means each and individually any of cyclopropylmethyl, cyclobutylmethyl, cyclopentylmethyl, cyclohexylmethyl, cycloheptylmethyl and cyclooctylmethyl.

In an embodiment and as preferably used herein, the term "halogen" or "halogenide" means each and individually any of F, Cl, Br, I and At.

In an embodiment and as preferably used herein atoms with unspecified atomic mass numbers in any structural formula or in any passage of the instant specification including the claims are either of unspecified isotopic composition, naturally occurring mixtures of isotopes or individual isotopes. This applies in particular to halogen atoms, including, but not limited to F Cl, Br, I and At and to metal atoms, including but not limited to Sc, Cr, Mn, Co, Fe, Cu, Ga, Sr, Zr, Y, Mo, Tc, Ru, Rh, Pd, Pt, Ag, In, Sb, Sn, Te, I, Pr, Pm, Dy, Sm, Gd, Tb, Ho, Dy, Er, Yb, Tm, Lu, Sn, Re, Rd, Os, Ir, Au, Pb, Bi, Po, Fr, Ra, Ac, Th and Fm.

In an embodiment and as preferably used herein, a chelator is a compound which is capable of forming a chelate, whereby a chelate is a compound, preferably a cyclic compound where a metal or a moiety having an electron gap or a lone pair of electrons participates in the formation of the ring. More preferably, a chelator is this kind of compound where a single ligand occupies more than one coordination site at a central atom.

In an embodiment and as preferably used herein an antagonist to NTR1 is a compound which inhibits the activity of a ligand on NTR1 such as neurotensin, and more specifically inhibits the receptor mediated effects which arise from the binding of the ligand to NTR1. More preferably, the antagonist to NTR1 is binding to NTR1.

In an embodiment and as preferably used herein, an effector is a compound which is diagnostically and/or therapeutically active in the diagnosis and therapy, respectively, of a disease.

In an embodiment and as preferably used herein, a diagnostically active compound is a compound which is suitable for or useful in the diagnosis of a disease.

In an embodiment and as preferably used herein, a diagnostic agent or a diagnostically active agent is a compound which is suitable for or useful in the diagnosis of a disease.

In an embodiment and as preferably used herein, a therapeutically active compound is a compound which is suitable for or useful in the treatment of a disease.

In an embodiment and as preferably used herein, a therapeutic agent or a therapeutically active agent is a compound which is suitable for or useful in the treatment of a disease.

In an embodiment and as preferably used herein, a theragnostically active compound is a compound which is suitable for or useful in both the diagnosis and therapy of a disease.

In an embodiment and as preferably used herein, a theragnostical agent or a theragnostically active agent is a compound which is suitable for or useful in both the diagnosis and therapy of a disease.

In an embodiment and as preferably used herein, theragnostics is a method for the combined diagnosis and therapy of a disease; preferably, the combined diagnostically and therapeutically active compounds used in theragnostics are radiolabeled.

In an embodiment and as preferably used herein, treatment of a disease is treatment and/or prevention of a disease.

In an embodiment and as preferably used herein, a disease involving neurotensin receptor is a disease where cells expressing neurotensin receptor and tissue expressing neurotensin receptor, respectively, are either a or the cause for the disease and/or the symptoms of the disease, or are part of the pathology underlying the disease. In an embodiment of the disease, preferably when used in connection with the treatment, treating and/or therapy of the disease, affecting the cells, the tissue and pathology, respectively, results in cure, treatment or amelioration of the disease and/or the symptoms of the disease. In an embodiment of the disease, preferably when used in connection with the diagnosis and/or diagnosing of the disease, labeling of the neurotensin receptor expressing cells and/or of the neurotensin receptor expressing tissue allows discriminating or distinguishing said cells and/or said tissue from healthy or neurotensin receptor non-expressing cells and/or healthy or neurotensin receptor non-expressing tissue. More preferably such discrimination or distinction forms the basis for said diagnosis and diagnosing, respectively. In an embodiment thereof, labeling means the interaction of a detectable label either directly or indirectly with the neurotensin receptor expressing cells and/or with the neurotensin receptor expressing tissue; more preferably such interaction involves or is based on the interaction of the label or a compound bearing such label with the neurotensin receptor.

In an embodiment and as preferably used herein, a disease involving neurotensin receptor 1 (NTR1) is a disease where cells expressing NTR1 and tissue expressing NTR1, respectively, are either a or the cause for the disease and/or the symptoms of the disease, or are part of the pathology underlying the disease. In an embodiment of the disease, preferably when used in connection with the treatment, treating and/or therapy of the disease, affecting the cells, the tissue and pathology, respectively, results in cure, treatment or amelioration of the disease and/or the symptoms of the disease. In an embodiment of the disease, preferably when used in connection with the diagnosis and/or diagnosing of the disease, labeling of the NTR1 expressing cells and/or of the NTR1 expressing tissue allows discriminating or distinguishing said cells and/or said tissue from healthy or NTR1 non-expressing cells and/or healthy or NTR1 non-expressing tissue. More preferably such discrimination or distinction forms the basis for said diagnosis and diagnosing, respectively, of the disease. In an embodiment thereof, labeling means the interaction of a detectable label either directly or indirectly with the NTR1 expressing cells and/or with the NTR1 expressing tissue; more preferably such interaction involves or is based on the interaction of the label or a compound bearing such label with the NTR1 receptor.

In an embodiment and as preferably used herein, a target cell is a cell which is expressing NTR1 and is a or the cause for a disease and/or the symptoms of a disease, or are part of the pathology underlying a disease.

In an embodiment and as preferably used herein, a non-target cell is a cell which is either not expressing NTR1 and/or is not a or the cause for a disease and/or the symptoms of a disease, or is part of the pathology underlying a disease.

In an embodiment and as preferably used herein a linkage is an attachment of two atoms of two independent moieties. A preferred linkage is a chemical bond or a plurality of chemical bonds. More preferably a chemical bond is a covalent bond or a plurality of chemical bonds. Most preferably the linkage is a covalent bond or a coordinate bond. As preferably used herein, an embodiment of a coordinate bond is a bond or group of bonds as realized when a metal is bound by a chelator. Depending on the type of atoms linked and their atomic environment different types of linkages are created. These types of linkage are defined by the type of atom arrangements created by the linkage. For instance, the linking of a moiety comprising an amine with a moiety comprising a carboxylic acid leads to a linkage named amide (which is also referred to as amide linkage, —CO—N—, —N—CO—). It will be acknowledged by a person in the art that the linking of a moiety comprising an isothiocyanate with a moiety comprising an amine leads to thiourea (which is also referred to as a thiourea linkage, —N—CS—N—), and linking of a moiety comprising a C atom with a moiety comprising a thiol-group (—C—SH) leads to thioether (which is also referred to as a thioether linkage, —C—S—C—).

In an embodiment and as preferably used herein, alkylamine is a type of linkage, wherein a N atom is bound to an aliphatic C atom (which is also referred to as a alkylamine linkage, —N—C—). In one embodiment the alkylamine linkage is formed by reacting a moiety comprising an amine with a moiety comprising an aldehyde either under reductive conditions or followed by subsequent reduction.

In an embodiment and as preferably used herein the term "mediating a linkage" means that a linkage or a type of linkage is established, preferably a linkage between two moieties. In a preferred embodiment the linkage and the type of linkage is as defined herein.

To the extent it is referred in the instant application to a range indicated by a lower integer and a higher integer such as, for example, 1-4, such range is a representation of the lower integer, the higher integer and any integer between the lower integer and the higher integer. Insofar, the range is actually an individualized disclosure of said integer. In said example, the range of 1-4 thus means 1, 2, 3 and 4.

In the compound of the invention the moiety -[Acceptor-Effector] is, in an embodiment, directly attached to the N atom of the moiety of formula (II) as illustrated in formula (IIb):

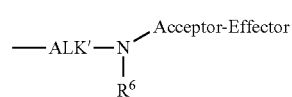
(IIb)

In an alternative embodiment, a linker is introduced linking the N atom of the moiety of formula (II) with the moiety -[Acceptor-Effector] as illustrated in formula (IId):

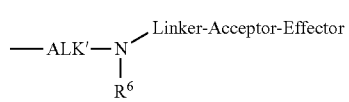
(IId)

As preferably used herein, a Linker which is used or present in the compound of the invention is a moiety which links or is capable of linking the N atom of the group of formula (IIc) with the Acceptor of the group of formula (IIc), whereby the linking is preferably a covalent linking:

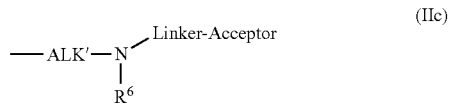
(IIc)

or the N atom of the group of formula (IId) with the Acceptor of the moiety -[Acceptor-Effector] of the group of formula (IId):

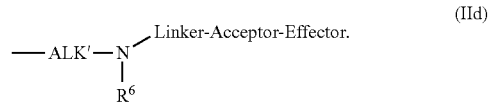
(IId)

Preferably, the function of the linker is such that the binding characteristics of the compound of the invention to a target molecule is not affected by the Acceptor, regardless whether or not an Effector is covalently bound to or complexed by the Acceptor.

In an embodiment the covalent linkage between the linker and the N atom of the group of formula (II) is selected from the group comprising amide, urea, thiourea and alkylamine.

In a further embodiment, the covalent linkage between the linker and the acceptor is selected from the group comprising amide (also referred to as amide linkage), alkylamine (also referred to as alkylamine linkage), urea (also referred to as urea linkage), ether (also referred to as ether linkage), thioether (also referred to as thioether linkage), thiourea (also referred to as thiourea linkage) and carbamate (also referred to as carbamate linkage).

In a still further embodiment the Linker is an amino acid or a peptide consisting of 2 to 10 amino acids, whereby the amino acids are independently selected from the group of natural and non-natural amino acids. Amino acids as used in this embodiment of the Linker include, but are not limited, to α-amino acids and amino acids where the amino and the carboxylic group are spaced further apart such as β-amino acids, γ-amino acids, δ-amino acids, ε-amino acids and ω-amino acids. In any case the amino acids may be cyclic or linear. In the case of amino acids with stereogenic centers all stereoisomeric forms may be used. This kind of Linker is covalently attached to the $R^6$ substituted nitrogen of the group of formula (II) by any carboxy group of the Linker forming an amide linkage. The Acceptor can be attached to any remaining appropriate functionality of the peptide or amino acid forming the Linker-Acceptor linkage, whereby such functionality is preferably selected from the group comprising amine, thiol, hydroxy and carboxylic acid.

In another embodiment, the Linker is a moiety according to formula (VI) or formula (VII):

(VI)

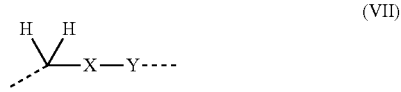
(VII)

wherein X is each individually and independently selected from the group comprising (C$_2$-C$_{10}$)alkylidene, oligoether or polyether wherein said oligoether or polyether consist of 2 to 500 ether oxygen atoms, preferably 2 to 100 ether oxygen atoms; and Y is each individually and independently selected from the group comprising N—R$^8$, O, S and succinimide, wherein R$^8$ is selected from the group comprising H or (C$_1$-C$_4$)alkyl.

It will be acknowledged that the Linker being or comprising a moiety according to formula (VI) or formula (VII) are implemented in a moiety according to formula (II) as is evident from formulae (VIII), (VIIIa), (IX) and (IXa).

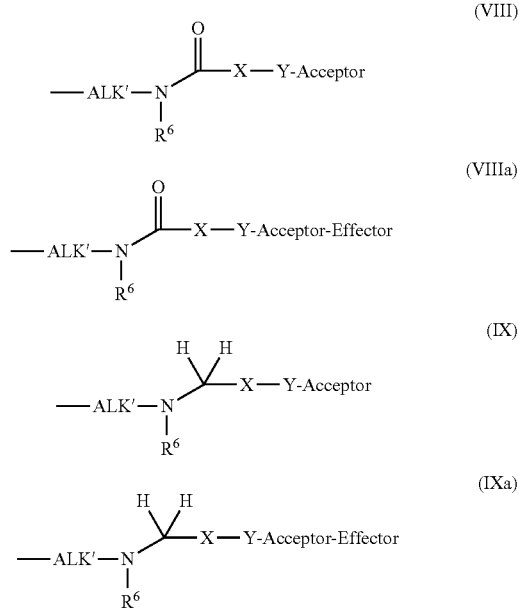

In an embodiment, the Linker is not cleavable. Not cleavable as preferably used herein means that the Linker cannot, at least not under physiological conditions or in vivo conditions as existing in the body of a mammal, be separated, either in its entirety or partially, from the compound of the invention.

Acceptor as preferably used herein is a moiety which is used or present in the compound of the invention and which mediates the linking of an Effector to the N atom of the group of formula (II). In one embodiment the Acceptor is covalently linked to or is capable of covalently binding the N atom of the group of formula (II) forming the structure of formula (IIa). Acceptor is either bound to or complexed with Effector or Acceptor allows the site-specific introduction of the Effector in a compound of formula (IIa).

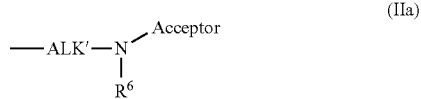

In an alternative embodiment, the Acceptor mediates the linking of an Effector to the Linker, whereby the Linker is linked to the N atom of the group of formula (II) forming the structure of (IIc):

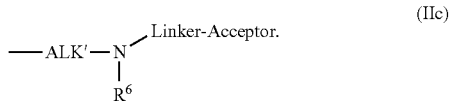

It will be acknowledged by the person skilled in the art that in both embodiments the Acceptor is either bound to or complexed with the Effector or allows the site-specific introduction of the Effector into the compound of the invention.

In an embodiment where there is a direct linkage, preferably a direct covalent linkage, of the Acceptor to the N atom of the group of formula (II) such linkage is selected from the group comprising amide, alkylamine, urea, thiourea and carbamate. In a further embodiment, the covalent linkage between the Linker and the Acceptor is selected from the group comprising amide, amine, urea, ether, thioether, thiourea and carbamate.

In a further embodiment the Acceptor comprises a functional group which is capable of forming a covalent linkage to either the Linker or the N atom of the group of formula (II) without destroying the Acceptor's function, i.e. the binding or complexing of the Effector. Such functional group is preferably selected from the group comprising COOH, HN—R$^8$, OH, SH, acid halogenide, alkyl halogenide, aldehyde, isocyanate, isothiocyanate and maleimide, wherein R$^8$ is selected from the group comprising H or (C$_1$-C$_4$)alkyl.

It is within the present invention that the Effector is attached to the N atom of the moiety of formula (II) (which is also referred to as group of formula (II)) by means of the Acceptor, whereby the Acceptor can be either directly or indirectly bound to the N atom of the moiety of formula (II). Such Acceptor is, among others, a chelator. In one embodiment thereof, the compound of the invention is bearing a metal, preferably a radioactive transition metal which is chelated by the chelator. In another embodiment, the compound of the invention is bearing the chelator with no metal chelated by the chelator.

Possible forms of chelating interaction which allow the practicing of the present invention between a chelator and an Effector, which is preferably a transition metal, are known to the person skilled in the art and respective examples, structures and applications are, for example, described in Wadas et al. (Wadas et al., *Chem. Rev.*, 2010, 110, 2858-2902) and literature cited therein.

In another embodiment Acceptor is or comprises an aromate, preferably an electron rich aromate such as indoles or benzenes optionally substituted by oxygen, nitrogen sulfur atoms. In one embodiment thereof, the compound of the invention is bearing a halogen, preferably a radioactive halogen which is substituting said aromatic moiety. In another embodiment, the compound of the invention is bearing the aromatic moiety with no halogen bound to this aromatic moiety.

It will be acknowledged by a person skilled in the art that the specific effector which is or which is to be attached to the compound of the invention, is selected taking into consideration the disease to be treated and the disease to be diagnosed, respectively, and the particularities of the patient and patient group, respectively, to be treated and to be diagnosed, respectively.

In an embodiment the Effector is a radioactive nuclide which is also referred to as radionuclide. Radioactive decay is the process by which an atomic nucleus of an unstable atom loses energy by emitting ionizing particles (ionizing radiation). There are different types of radioactive decay. A decay, or loss of energy, results when an atom with one type of nucleus, called the parent radionuclide, transforms to an atom with a nucleus in a different state, or to a different nucleus containing different numbers of protons and neutrons. Either of these products is named the daughter nuclide. In some decays the parent and daughter are different chemical elements, and thus the decay process results in nuclear transmutation (creation of an atom of a new element). For example the radioactive decay can be alpha decay, beta decay, and gamma decay. Alpha decay occurs when the nucleus ejects an alpha particle (helium nucleus). This is the most common process of emitting nucleons, but in rarer types of decays, nuclei can eject protons, or specific nuclei of other elements (in the process called cluster decay). Beta decay occurs when the nucleus emits an electron ($\beta^-$-decay) or positron ($\alpha^+$-decay) and a type of neutrino, in a process that changes a proton to a neutron or the other way around. By contrast, there exist radioactive decay processes that do not result in transmutation. The energy of an excited nucleus may be emitted as a gamma ray in gamma decay, or used to eject an orbital electron by interaction with the excited nucleus in a process called internal conversion.

In a preferred embodiment of the present invention, the radionuclide can be used for stable labeling of the compound of the invention.

In a preferred embodiment of the present invention, the radionuclide has a half-life that allows for diagnostic or therapeutic medical use. Specifically, the half-life is between 30 min and 7 days. More specifically, the half-life is between 2 h and 3 days.

In a preferred embodiment of the present invention, the radionuclide has a decay energy and radiation range that allows for diagnostic or therapeutic medical use.

In a preferred embodiment of the present invention, the radionuclide is industrially produced for medical use. Specifically, the radionuclide is available in GMP quality.

In a preferred embodiment of the present invention, the daughter nuclide(s) after radioactive decay of the radionuclide are compatible with the diagnostic or therapeutic medical use. Specifically, the daughter nuclide(s) remain chemically bound or complexed to the compound of the invention and are not toxic. Furthermore, the daughter nuclides are either stable or further decay in a way that does not interfere with or even support the diagnostic or therapeutic medical use.

In an embodiment of the present invention, the radionuclide which is preferably a metal and more preferably a transition metal, is suitable for being complexed with a metal chelator and leading to radioactive metal chelator for imaging. It will, however, be acknowledged by a person skilled in the art that the radionuclide may also be directly bound to the compound of the invention. Preferably, the radioactive isotope is selected from the group comprising $^{18}F$, $^{110}In$, $^{113m}In$, $^{114m}In$, $^{99m}Tc$, $^{67}Ga$, $^{52}Fe$, $^{59}Fe$, $^{68}Ga$, $^{111}In$, $^{97}Ru$, $^{203}Pb$, $^{62}Cu$, $^{64}Cu$, $^{67}Cu$, $^{51}Cr$, $^{51}Mn$, $^{52m}Mn$, $^{55}Co$, $^{57}Co$, $^{58}Co$, $^{72}As$, $^{75}Se$, $^{157}Gd$, $^{120}I$, $^{123}I$, $^{124}I$, $^{125}I$, $^{131}I$, $^{75}Br$, $^{76}Br$, $^{77}Br$, $^{89}Zr$, $^{82m}Rb$, $^{83}Sr$, $^{86}Y$, $^{94m}Tc$, $^{169}Yb$, $^{197}Hg$, $^{201}Tl$, and $^{82}Br$. More preferably, the radioactive metal is selected from the group comprising $^{99m}Tc$, $^{67}Ga$, $^{68}Ga$, $^{111}In$, $^{89}Zr$ and $^{123}I$. Even more preferably the radioactive metal is $^{111}In$ and $^{89}Zr$. It will however, also be acknowledged by a person skilled in the art that the use of said radioactive metals is not limited to imaging purposes, but encompasses their use in diagnosis, therapy and theragnostics.

In an embodiment of the present invention, the radionuclide which is preferably a metal and more preferably a transition metal is suitable for complexing with a metal chelator and leading to radioactive metal chelator for radiotherapy. It will, however, be acknowledged by a person skilled in the art that the radionuclide may also be directly bound to the compound of the invention. Preferably, the radioactive isotope is selected from the group comprising $^{32}P$, $^{33}P$, $^{47}Sc$, $^{58}Co$, $^{59}Fe$, $^{64}Cu$, $^{67}Cu$, $^{67}Ga$, $^{68}Ga$, $^{75}Se$, $^{77}As$, $^{80m}Br$, $^{89}Sr$, $^{89}Zr$, $^{90}Y$, $^{99}Mo$, $^{103m}Rh$, $^{105}Rh$, $^{109}Pd$, $^{109}Pt$, $^{111}Ag$, $^{111}In$, $^{119}Sb$, $^{121}Sn$, $^{127}Te$, $^{125}I$, $^{123}I$, $^{129}I$, $^{131}I$, $^{142}Pr$, $^{143}Pr$, $^{149}Pm$, $^{151}Pm$, $^{152}Dy$, $^{153}Sm$, $^{159}Gd$, $^{161}Tb$, $^{161}Ho$, $^{166}Ho$, $^{166}Dy$, $^{169}Er$, $^{169}Yb$, $^{175}Yb$, $^{172}Tm$, $^{177}Lu$, $^{177m}Sn$, $^{186}Re$, $^{188}Re$, $^{189}Re$, $^{188}Rd$, $^{189m}Os$, $^{192}Ir$, $^{194}Ir$, $^{198}Au$, $^{199}Au$, $^{211}At$, $^{211}Pb$, $^{212}Pb$, $^{211}Bi$, $^{212}Bi$, $^{213}Bi$, $^{215}Po$, $^{217}At$, $^{219}Rn$, $^{221}Fr$, $^{223}Ra$, $^{225}Ac$, $^{227}Th$, $^{255}Fm$. More preferably, the radioactive isotope is selected from the group comprising $^{111}In$, $^{77}Lu$, $^{89}Zr$, $^{67}Ga$, $^{68}Ga$, $^{67}Cu$, $^{64}Cu$ and $^{90}Y$. More preferably, the radioactive metal is selected from the group comprising $^{111}In$, $^{90}Y$ and $^{177}Lu$. It will however, also be acknowledged by a person skilled in the art that the use of said radioactive metals is not limited to imaging purposes, but encompasses their use in diagnosis, therapy and theragnostics.

In a further embodiment, the effector is a radioactive halogen such as iodine and bromine isotopes which can be used, when attached to the compound of the invention, for therapy, diagnosis and/or theragnostics. In a preferred embodiment the radioactive halogen is bonded directly to the compound of the invention.

Preferred radionuclides used for diagnosis such as $^{68}Ga$, $^{111}In$ and $^{89}Zr$, and preferred radionuclides used for therapy such as $^{90}Y$, $^{153}Sm$ and $^{177}Lu$, are trivalent cations from the class of elements known as the lanthanides. Typical radioactive metals in this class include the isotopes $^{90}Yttrium$, $^{111}Indium$, $^{149}Promethium$, $^{153}Samarium$, $^{166}Dysprosium$, $^{166}Holmium$, $^{175}Ytterbium$, and $^{177}Lutetium$. All of these metals and others in the lanthanide series have very similar chemistries, in that they remain in the +3 oxidation state and prefer to chelate to ligands that bear hard donor atoms such as oxygen/nitrogen donor atoms.

As is evident from the above, a radionuclide is, in principle, useful in the treatment and/or diagnosis of a disease when conjugated to the compound of the invention.

In an embodiment of the compound of the invention the compound of the invention comprises a chelator. Preferably, the chelator is part of the Acceptor of the compound of the invention, whereby the chelator is either directly or indirectly such as by a linker attached to the compound of the invention. A preferred chelator is a metal chelator, whereby the metal chelator preferably comprises at least one radioactive metal. The at least one radioactive metal is preferably useful in or suitable for diagnostic and/or therapeutic use and is more preferably useful in or suitable for imaging and/or radiotherapy.

Chelators in principle useful in and/or suitable for the practicing of the instant invention including diagnosis and/or therapy of a disease, are known to the person skilled in the art. A wide variety of respective chelators is available and has been reviewed, e.g. by Banerjee et al. (Banerjee et al., *Nucl. Med. Biol.*, 2005, 32, 1-20, and references therein, Wadas et al., *Chem. Rev.*, 2010, 110, 2858-2902 and references therein) included herein by reference. Such chelators include, but are not limited to linear, macrocyclic, tetrapyridine and $N_3S$, $N_2S_2$ and $N_4$ chelators as disclosed in U.S. Pat. Nos. 5,367,080 A, 5,364,613 A, 5,021,556 A, 5,075,099 A, 5,886,142 A; HYNIC, DTPA, EDTA, DOTA, TETA, bisamino bisthiol (BAT) based chelators as disclosed in U.S. Pat. No. 5,720,934; Desferrioxamin (DFO) as disclosed (Doulias et al., *Free Radic. Biol. Med.*, 2003, 35, 719-728), whereby all of the references are included herein by reference in their entirety.

The diagnostic and/or therapeutic use of some of the above chelators is described in the prior art. For example, 2-hydrazino nicotinamide (HYNIC) has been widely used in the presence of a coligand for incorporation of $^{99m}Tc$ and $^{186,188}Re$ (Schwartz et al., *Bioconj. Chem.*, 1991, 2, 333-336; Babich et al., *J. Nucl. Med.*, 1993, 34, 1964-1970; Babich et al., *Nucl. Med. Biol.*, 1995, 22, 25-30); DTPA is used in Octreoscan® which is marketed by Covidien, for complexing $^{111}In$ and several modifications are described in the literature (Brechbiel et al., *Bioconj. Chem.*, 1991, 2, 187-194; Li et al., *Nucl Med. Biol.*, 2001, 28, 145-154); DOTA type chelators for radiotherapy applications are described by Tweedle et al. (U.S. Pat. No. 4,885,363); other polyaza macrocycles for chelating trivalent isotopes metals are described by Maecke et al., *Bioconj. Chem.*, 2002, 13, 530-541; and $N_4$-chelators such as a $^{99m}Tc$—$N_4$-chelator have been used for peptide labeling in the case of minigastrin for targeting CCK-2 receptors (Nock et al., *J. Nucl Med.*, 2005, 46, 1727-1736).

In a preferred embodiment of the present invention, the metal chelator is a metal chelator for trivalent metals or for pentavalent metals and their close analogs. Many metal chelators of this type are disclosed by WO2009/109332 A1.

In an embodiment the metal chelator for trivalent metals is selected from the group comprising DOTA, NOTA, DTPA, TETA, EDTA, NODAGA, NODASA, TRITA, CDTA, BAT, DFO and HYNIC based chelators and their close analogs, wherein DOTA stands for 1,4,7,10-tetrazacyclododecane-1,4,7,10-tetraacetic acid,
NOTA stands for 1,4,7-triazacyclononanetriacetic acid,
DTPA stands for diethylenetriaminepentaacetic acid,
TETA stands for 1,4,8,11-tetraazacyclododecane-1,4,8,11-tetraacetic acid,
EDTA stands for ethylenediamine-N,N'-tetraacetic acid,
NODAGA stands for 1,4,7-triazacyclononane-N-glutaric acid-N',N''-diacetic acid,
NODASA stands for 1,4,7-triazacyclononane-1-succinic acid-4,7-diacetic acid,
TRITA stands for 1,4,7,10 tetraazacyclotridecane-1,4,7,10-tetraacetic acid,
CDTA stands for trans-1,2-diaminocyclohexane-N,N,N',N'-tetraacetic acid,
DFO stands for the Desferal or Desferrioxamine type group of chelators, the chemical name of the non-limiting example is N-[5-({3-[5-(Acetyl-hydroxy-amino)-pentylcarbamoyl]-propionyl}-hydroxy-amino)-pentyl]-N'-(5-amino-pentyl)-N'-hydroxy-succinamide,
BAT stands for the Bisamino-bisthiol group of chelators, the chemical name of the non limiting example is 1-[2-(2-mercapto-2-methyl-propylamino)-ethylamino]-2-methyl-propane-2-thiol,
HYNIC stands for 6-Hydrazino-nicotinic acid,
and with the chemical structures thereof being as follows:

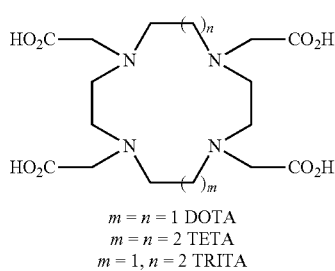
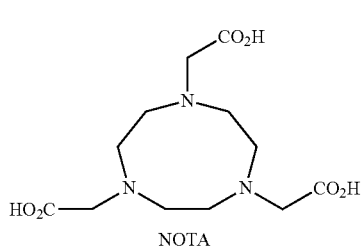
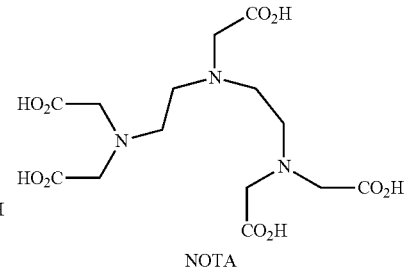
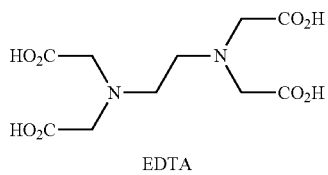
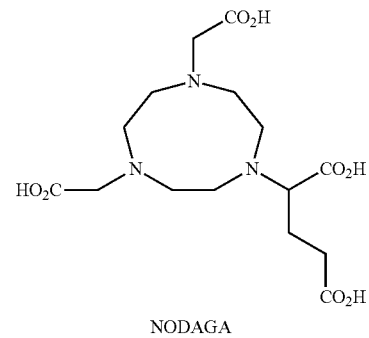
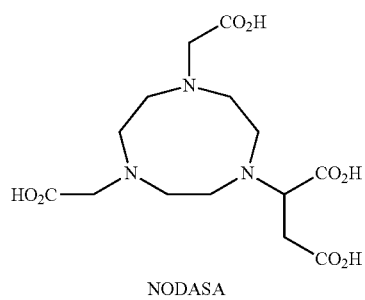

-continued

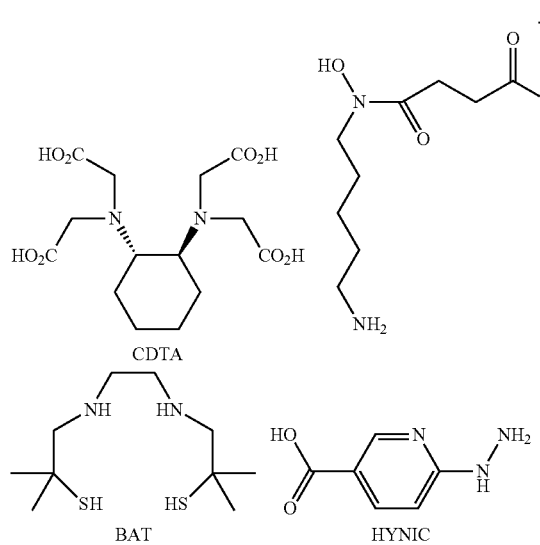

CDTA

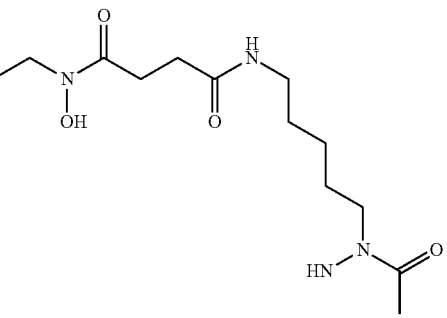

DFO

BAT  HYNIC

In a preferred embodiment the metal chelator is selected from the group comprising DOTA-, NOTA-, DTPA-, TETA-DFO and HYNIC based chelators and their close analogs.

Compounds of the invention which are complexes of a metal with a chelator a clearly and precisely termed by the following short notation:

In "$^{xxx}$Metal-(YY)" the optional atomic mass number of specific isotopes (xxx) in superscript is followed directly by the atomic symbol of metal (Metal), separated by an hyphen from number of the formula of the parent uncomplexed compound (YY) in parentheses; Lu-(IIIa), for instance, means Lutethium complexed to a chelator of the compound of formula (IIIa) and $^{111}$In-(IIIc), for instance, means $^{111}$Indium complexed to a chelator of the compound of formula (IIIc).

In a more preferred embodiment the metal chelator for trivalent metals is selected from the group comprising DTPA (diethylenetriaminepentaacetic acid) and polyaza-polycarboxylate macrocycles such as DOTA (1,4,7,10-tetrazacyclododecane-1,4,7,10-tetraacetic acid) and the close analogs thereof.

In one preferred embodiment the metal chelator for $^{89}$Zr is DFO, DTPA, DOTA or EDTA.

It will be acknowledged by the persons skilled in the art that the chelator, in principle, may be used regardless whether the compound of the invention is used in or suitable for diagnosis or therapy. Such principle are, among others, outlined in international patent application WO 2009/109332 A1.

In an embodiment the compound of the invention is present as a pharmaceutically acceptable salt.

A "pharmaceutically acceptable salt" of the compound of the present invention is preferably an acid salt or a base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Compounds of the invention are capable of forming internal salts which are also pharmaceutically acceptable salts.

Suitable pharmaceutically acceptable salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 4, i.e., 0, 1, 2, 3, or 4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

A "pharmaceutically acceptable solvate" of the compound of the invention is preferably a solvate of the compound of the invention formed by association of one or more solvent molecules to one or more molecules of a compound of the invention. Preferably, the solvent is one which is generally considered in the art to be suitable for use in contact with the tissues of human beings or animals without excessive toxicity or carcinogenicity, and preferably without irritation, allergic response, or other problem or complication. Such solvent includes an organic solvent such as alcohols, ethers, esters and amines.

A "hydrate" of the compound of the invention is formed by association of one or more water molecules to one or more molecules of a compound of the invention. Such hydrate includes but is not limited to a hemi-hydrate, monohydrate, dihydrate, trihydrate and tetrahydrate. Independent of the hydrate composition all hydrates are generally considered as pharmaceutically acceptable.

The compound of the invention has a high binding affinity to neurotensin receptors and NTR1 in particular. Because of this high binding affinity, the compound of the invention is effective as, useful as and/or suitable as a targeting agent and, if conjugated to another moiety, as a targeting moiety. As preferably used herein a targeting agent is an agent which interacts with the target molecule which are in the instant case said neurotensin receptors. In terms of cells and tissues thus targeted by the compound of the invention any cell and tissue, respectively, expressing said neurotensin receptors and NTR1 in particular is targeted. As is known from the prior art, apart from the central nervous system and intestine, NTR1 is highly expressed in a mammalian body and a human body in particular on several neoplastic cells in several tumor indications whereas the expression of NTR1 in other tissues of the mammalian and the human body is low. These NTR1-expressing tumor indications include but are not limited to ductal pancreatic adenocarcinoma (Reubi et al., *Gut,* 1998, 42, 546-550; Ehlers et al., *Ann. Surg.,* 2000, 231, 838-848), small cell lung cancer (Reubi et al., *Int. J. Cancer,* 1999, 82, 213-218), prostate cancer (Taylor et al., *Prostate,* 2012, 72, 523-532), colorectal carcinoma (Chao et al., *J. Surg. Res.,* 2005, 129, 313-321; Gui et al., *Peptides,* 2008, 29, 1609-1615), breast cancer (Souaze et al., *Cancer Res.,* 2006, 66, 6243-6249), meningioma (Reubi et al., *Int. J. Cancer,* 1999, 82, 213-218), Ewing's sarcoma (Reubi et al., *Int. J. Cancer,* 1999, 82, 213-218), pleural mesothelioma (Alifano et al., *Biochimie,* 2010, 92, 164-170), head and neck cancer (Shimizu et al., *Int. J. Cancer,* 2008, 123, 1816-1823), non-small lung cancer (Alifano et al., *Clin. Cancer Res.,* 2010, 16, 4401-4410; Moody et al., *Panminerva Med.,* 2006, 48, 19-26; Ocejo-Garcia et al., *Lung Cancer,* 2001, 33, 1-9), gastrointestinal stromal tumors (Gromova et al., *PLoS One,* 2011, 6, e14710), uterine leiomyoma (Rodriguez et al., *Biol. Reprod.,* 2010, 83, 641-647; Rodriguez et al., *Int. J. Gynecol. Pathol.,* 2011, 30, 354-363) and cutaneous T-cell lymphoma (Ramez et al., *J. Invest. Dermatol.,* 2001, 117, 687-693). Accordingly, the compound of the invention is thus particularly suitable for and useful in the diagnosis and treatment, respectively, of these diseases. Insofar, the above indications are indications which can be treated by the compound of the invention. It will be understood by the person skilled in the art that also metastases and metastases of the above indications in particular can be treated and diagnosed by the compound of the invention and the methods of diagnosis and methods of treatment making use of the compound of the invention.

A further indication in connection with which the compound of the invention may be used, either for therapeutic purposes or for diagnostic purposes, is hematological malignancies which is plausible in view of the expression of NTR1 in blood cells and T-cell lymphoma cells in particular as reported by Ramez et al. In an embodiment the disease is T-cell lymphoma.

It is within the present invention that the compound of the invention is used in a method for the treatment of a disease as disclosed herein. Such method, preferably, comprises the step of administering to a subject in need thereof a therapeutically effective amount of the compound of the invention. Such method includes, but is not limited to, curative or adjuvant cancer treatment. It is used as palliative treatment where cure is not possible and the aim is for local disease control or symptomatic relief or as therapeutic treatment where the therapy has survival benefit and it can be curative.

The method for the treatment of a disease as disclosed herein includes the treatment of malignant tumors cancer, and may be used either as the primary therapy or as second, third, fourth or last line therapy. It is also within the instant invention to combine radiotherapy in accordance with instant invention with other treatments including surgery, chemotherapy, radiation therapy, targeted therapy, antiangiogenic therapy and hormone therapy which are well known in the art. It is well known to the person skilled in the art that the precise treatment intent including curative, adjuvant, neoadjuvant, therapeutic, or palliative treatment intent will depend on the tumor type, location, and stage, as well as the general health of the patient.

The method for the treatment of a disease as disclosed herein may also target the draining lymph nodes if they are clinically involved with tumor.

Preferably, radionuclide therapy makes use of or is based on different forms of radiation emitted by a radionuclide. Such radiation can, for example, be any one of radiation of photons, radiation of electrons including but not limited to $\beta^-$-particles and Auger-electrons, radiation of protons, radiation of neutrons, radiation of positrons, radiation of $\alpha$-particles or an ion beam. Depending on the kind of particle or radiation emitted by said radionuclide, radionuclide therapy can, for example, be distinguished as photon radionuclide therapy, electron radionuclide therapy, proton radionuclide therapy, neutron radionuclide therapy, positron radionuclide therapy, $\alpha$-particle radionuclide therapy or ion beam radionuclide therapy. All of these forms of radionuclide therapy are encompassed by the present invention, and all of these forms of radionuclide therapy can be realized by the compound of the invention, preferably under the proviso that the radionuclide attached to the compound of the invention, more preferably as an Effector, is providing for this kind of radiation.

Radionuclide therapy preferably works by damaging the DNA of cells. The damage is caused by a photon, electron, proton, neutron, positron, $\alpha$-particle or ion beam directly or indirectly ionizing the atoms which make up the DNA chain. Indirect ionization happens as a result of the ionization of water, forming free radicals, notably hydroxyl radicals, which then damage the DNA.

In the most common forms of radionuclide therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. The DNA damage is inherited through cell division, accumulating damage to the cancer cells, causing them to die or reproduce more slowly.

Oxygen is a potent radiosensitizer, increasing the effectiveness of a given dose of radiation by forming DNA-damaging free radicals. Therefore, use of high pressure oxygen tanks, blood substitutes that carry increased oxygen, hypoxic cell radiosensitizers such as misonidazole and metronidazole, and hypoxic cytotoxins, such as tirapazamine may be applied.

Other factors that are considered when selecting a radioactive dose include whether the patient is receiving chemotherapy, whether radiation therapy is being administered before or after surgery, and the degree of success of surgery.

The total radioactive dose may be fractionated, i.e. spread out over time in one or more treatments for several important reasons. Fractionation allows normal cells time to recover, while tumor cells are generally less efficient in repair between fractions. Fractionation also allows tumor cells that were in a relatively radio-resistant phase of the cell cycle during one treatment to cycle into a sensitive phase of the cycle before the next fraction is given. Similarly, tumor cells that were chronically or acutely hypoxic and, therefore, more radioresistant, may reoxygenate between fractions, improving the tumor cell kill.

It is generally known that different cancers respond differently to radiation therapy. The response of a cancer to radiation is described by its radiosensitivity. Highly radiosensitive cancer cells are rapidly killed by modest doses of radiation. These include leukemias, most lymphomas and germ cell tumors.

It is important to distinguish radiosensitivity of a particular tumor, which to some extent is a laboratory measure, from "curability" of a cancer by an internally delivered radioactive dose in actual clinical practice. For example, leukemias are not generally curable with radiotherapy, because they are disseminated through the body. Lymphoma may be radically curable if it is localized to one area of the body. Similarly, many of the common, moderately radioresponsive tumors can be treated with curative doses of radioactivity if they are at an early stage. This applies, for example, to non-melanoma skin cancer, head and neck cancer, non-small cell lung cancer, cervical cancer, anal cancer, prostate cancer.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radionuclide therapy. A third technique is to enhance the radiosensitivity of the cancer by giving certain drugs during a course of radiotherapy. Examples of radiosensiting drugs include, but are not limited to Cisplatin, Nimorazole, and Cetuximab.

Introperative radiotherapy is a special type of radiotherapy that is delivered immediately after surgical removal of the cancer. This method has been employed in breast cancer (TARGeted Introperative radioTherapy), brain tumors and rectal cancers.

Radionuclide therapy is in itself painless. Many low-dose palliative treatments cause minimal or no side effects. Treatment to higher doses may cause varying side effects during treatment (acute side effects), in the months or years following treatment (long-term side effects), or after re-treatment (cumulative side effects). The nature, severity, and longevity of side effects depends on the organs that receive the radiation, the treatment itself (type of radionuclide, dose, fractionation, concurrent chemotherapy), and the patient.

It is within the present inventions that the method for the treatment of a disease of the invention may realize each and any of the above strategies which are as such known in the art, and which insofar constitute further embodiments of the invention.

It is also within the present invention that the compound of the invention is used in a method for the diagnosis of a disease as disclosed herein. Such method, preferably, comprises the step of administering to a subject in need thereof a diagnostically effective amount of the compound of the invention.

In accordance with the present invention, an imaging method is selected from the group consisting of scintigraphy, Single Photon Emission Computed Tomography (SPECT) and Positron Emission Tomography (PET).

Scintigraphy is a form of diagnostic test or method used in nuclear medicine, wherein radiopharmaceuticals are internalized by cells, tissues and/or organs, preferably internalized in vivo, and radiation emitted by said internalized radiopharmaceuticals is captured by external detectors (gamma cameras) to form and display two-dimensional images. In contrast thereto, SPECT and PET forms and displays three-dimensional images. Because of this, SPECT and PET are classified as separate techniques to scintigraphy, although they also use gamma cameras to detect internal radiation. Scintigraphy is unlike a diagnostic X-ray where external radiation is passed through the body to form an image.

Single Photon Emission Tomography (SPECT) scans are a type of nuclear imaging technique using gamma rays. They are very similar to conventional nuclear medicine planar imaging using a gamma camera. Before the SPECT scan, the patient is injected with a radiolabeled chemical emitting gamma rays that can be detected by the scanner. A computer collects the information from the gamma camera and translates this into two-dimensional cross-sections. These cross-sections can be added back together to form a three-dimensional image of an organ or a tissue. SPECT involves detection of gamma rays emitted singly, and sequentially, by the radionuclide provided by the radiolabeled chemical. To acquire SPECT images, the gamma camera is rotated around the patient. Projections are acquired at defined points during the rotation, typically every 3-6 degrees. In most cases, a full 360 degree rotation is used to obtain an optimal reconstruction. The time taken to obtain each projection is also variable, but 15-20 seconds is typical. This gives a total scan time of 15-20 minutes. Multi-headed gamma cameras are faster. Since SPECT acquisition is very similar to planar gamma camera imaging, the same radiopharmaceuticals may be used.

Positron Emitting Tomography (PET) is a non-invasive, diagnostic imaging technique for measuring the biochemical status or metabolic activity of cells within the human body. PET is unique since it produces images of the body's basic biochemistry or functions. Traditional diagnostic techniques, such as X-rays, CT scans or MRI, produce images of the body's anatomy or structure. The premise with these techniques is that any changes in structure or anatomy associated with a disease can be seen. Biochemical processes are also altered by a disease, and may occur before any gross changes in anatomy. PET is an imaging technique that can visualize some of these early biochemical changes. PET scanners rely on radiation emitted from the patient to create the images. Each patient is given a minute amount of a radioactive pharmaceutical that either closely resembles a natural substance used by the body or binds specifically to a receptor or molecular structure. As the radioisotope undergoes positron emission decay (also known as positive beta decay), it emits a positron, the antiparticle counterpart of an electron. After traveling up to a few millimeters, the positron encounters an electron and annihilates, producing a pair of annihilation (gamma) photons moving in opposite directions. These are detected when they reach a scintillation material in the scanning device, creating a burst of light, which is detected by photomultiplier tubes or silicon avalanche photodiodes. The technique depends on simultaneous or coincident detection of the pair of photons. Photons that do not arrive in pairs, i.e., within a few nanoseconds, are ignored. All coincidences are forwarded to the image processing unit where the final image data is produced using image reconstruction procedures.

SPECT/CT and PET/CT is the combination of SPECT and PET with computed tomography (CT). The key benefits of combining these modalities are improving the reader's confidence and accuracy. With traditional PET and SPECT, the limited number of photons emitted from the area of abnormality produces a very low-level background that makes it difficult to anatomically localize the area. Adding CT helps determine the location of the abnormal area from an anatomic perspective and categorize the likelihood that this represents a disease.

It is within the present inventions that the method for the diagnosis of a disease of the invention may realize each and any of the above strategies which are as such known in the art, and which insofar constitute further embodiments of the invention.

Compounds of the present invention are useful to stratify patients, i.e. to create subsets within a patient population that provide more detailed information about how the patient will respond to a given drug. Stratification can be a critical component to transforming a clinical trial from a negative or neutral outcome to one with a positive outcome by identifying the subset of the population most likely to respond to a novel therapy.

Stratification includes the identification of a group of patients with shared "biological" characteristics to select the optimal management for the patients and achieve the best possible outcome in terms of risk assessment, risk prevention and achievement of the optimal treatment outcome A compound of the present invention may be used to assess or detect, a specific disease as early as possible (which is a diagnostic use), the risk of developing a disease (which is a susceptibility/risk use), the evolution of a disease including indolent vs. aggressive (which is a prognostic use) and it may be used to predict the response and the toxicity to a given treatment (which is a predictive use).

It is also within the present invention that the compound of the invention is used in a theranostic method. The concept of theranostics is to combine a therapeutic agent with a corresponding diagnostic test that can increase the clinical use of the therapeutic drug. The concept of theranostics is becoming increasingly attractive and is widely considered the key to improving the efficiency of drug treatment by helping doctors identify patients who might profit from a given therapy and hence avoid unnecessary treatments.

The concept of theranostics is to combine a therapeutic agent with a diagnostic test that allows doctors to identify those patients who will benefit most from a given therapy. In an embodiment and as preferably used herein, a compound of the present invention is used for the diagnosis of a patient, i.e. identification and localization of the primary tumor mass as well as potential local and distant metastases. Furthermore, the tumor volume can be determined, especially utilizing three-dimensional diagnostic modalities such as SPECT or PET. Only those patients having neurotensin receptor positive tumor masses and who, therefore, might profit from a given therapy are selected for a particular therapy and hence unnecessary treatments are avoided. Preferably, such therapy is a neurotensin receptor targeted therapy using a compound of the present invention. In one particular embodiment, chemically identical tumor-targeted diagnostics, preferably imaging diagnostics for scintigraphy, PET or SPECT and radiotherapeutics are applied. Such compounds only differ in the radionuclide and therefore usually have a very similar if not identical pharmacokinetic profile. This can be realized using a chelator and a diagnostic or therapeutic radiometal. Alternatively, this can be realized using a precursor for radiolabeling and radiolabeling with either a diagnostic or a therapeutic radionuclide. In one embodiment diagnostic imaging is used preferably by means of quantification of the radiation of the diagnostic radionuclide and subsequent dosimetry which is known to those skilled in the art and the prediction of drug concentrations in the tumor compared to vulnerable side effect organs. Thus, a truly individualized drug dosing therapy for the patient is achieved.

In an embodiment and as preferably used herein, the theragnostic method is realized with only one theragnostically active compound such as a compound of the present invention labeled with a radionuclide emitting diagnostically detectable radiation (e.g. positrons or gamma rays) as well as therapeutically effective radiation (e.g. electrons).

The invention also contemplates a method of intraoperatively identifying/disclosing diseased tissues expressing neurotensin receptors in a subject. Such method uses a compound of the invention, whereby such compound of the invention preferably comprises as Effector a diagnostically active agent.

According to a further embodiment of the invention, the compound of the invention, particularly if complexed with a radionuclide, may be employed as adjunct or adjuvant to any other tumor treatment including, surgery as the primary method of treatment of most isolated solid cancers, radiation therapy involving the use of ionizing radiation in an attempt to either cure or improve the symptoms of cancer using either sealed internal sources in the form of brachytherapy or external sources, chemotherapy such as alkylating agents, antimetabolites, anthracyclines, plant alkaloids, topoisomerase inhibitors, and other antitumor agents, hormone treatments that modulate tumor cell behavior without directly attacking those cells, targeted agents which directly target a molecular abnormality in certain types of cancer including monoclonal antibodies and tyrosine kinase inhibitors, angiogenesis inhibitors, immunotherapy, cancer vaccination, palliative care including actions to reduce the physical, emotional, spiritual, and psycho-social distress to improve the patient's quality of life and alternative treatments including a diverse group of health care systems, practices, and products that are not part of conventional medicine.

In an embodiment of the methods of the invention, the subject is a patient. In an embodiment, a patient is a subject which has been diagnosed as suffering from or which is suspected of suffering from or which is at risk of suffering from or developing a disease, whereby the disease is a disease as described herein and preferably a disease involving neurotensin receptor and more preferably neurotensin receptor 1.

Dosages employed in practicing the methods for treatment and diagnosis, respectively, where a radionuclide is used and more specifically attached to or part of the compound of the invention will vary depending e.g. on the particular condition to be treated, for example the known radiosensitivity of the tumor type, the volume of the tumor and the therapy desired. In general, the dose is calculated on the basis of radioactivity distribution to each organ and on observed target uptake. A γ-emitting complex may be administered once or at several times for diagnostic imaging. In animals, an indicated dose range may be from 0.1 µg/kg to 5 mg/kg of the compound of the invention complexed e.g. with 1 to 200 MBq of $^{111}$In or $^{89}$Zr. A β-emitting complex of the compound of the invention may be administered at several time points e.g. over a period of 1 to 3 weeks or longer. In animals, an indicated dosage range may be of from 0.1 µg/kg to 5 mg/kg of the compound of the invention complexed e.g. with 1 to 200 MBq $^{90}$Y or $^{177}$Lu. In larger mammals, for example humans, an indicated dosage range is from 0.1 to 100 g/kg of the compound of the invention complexed with e.g. 10 to 400 MBq $^{111}$In or $^{89}$Zr.

In larger mammals, for example humans, an indicated dosage range is of from 0.1 to 100 µg/kg of the compound of the invention complexed with e.g. 10 to 5000 MBq $^{90}$Y or $^{177}$Lu.

In a further aspect, the instant invention is related to a composition and a pharmaceutical composition in particular, comprising the compound of the invention.

The pharmaceutical composition of the present invention comprises at least one compound of the invention and, optionally, one or more carrier substances, excipients and/or adjuvants. The pharmaceutical composition may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included in the pharmaceutical composition of the invention.

The pharmaceutical composition of the invention may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, intrathecal and intraperitoneal injection, as well as any similar injection or infusion technique. A preferred route of administration is intravenous administration.

In an embodiment of the invention the compound of the invention comprising a radionuclide is administered by any conventional route, in particular intravenously, e.g. in the form of injectable solutions or suspensions. The compound of the invention may also be administered advantageously by infusion, e.g., by an infusion of 30 to 60 min.

Depending on the site of the tumor, the compound of the invention may be administered as close as possible to the tumor site, e.g. by means of a catheter. Such administration may be carried out directly into the tumor tissue or into the surrounding tissue or into the afferent blood vessels. The compound of the invention may also be administered repeatedly in doses, preferably in divided doses.

According to a preferred embodiment of the invention, a pharmaceutical composition of the invention comprises a stabilizer, e.g. a free radical scavenger, which inhibits autoradiolysis of the compound of the invention. Suitable stabilizers include, e.g., serum albumin, ascorbic acid, retinol, gentisic acid or a derivative thereof, or an amino acid infusion solution such, e.g., used for parenteral protein feeding, preferably free from electrolyte and glucose, for example a commercially available amino acid infusion such as Proteinsteril® KE Nephro. Ascorbic acid and gentisic acid are preferred.

A pharmaceutical composition of the invention may comprise further additives, e.g. an agent to adjust the pH between 7.2 and 7.4, e.g. sodium or ammonium acetate or $Na_2HPO_4$. Preferably, the stabilizer is added to the non-radioactive compound of the invention and introduction of the radionuclide, for instance the complexation with the radionuclide, is performed in the presence of the stabilizer, either at room temperature or, preferably, at a temperature of from 40 to 120° C. The complexation may conveniently be performed under air free conditions, e.g. under $N_2$ or Ar. Further stabilizer may be added to the composition after complexation.

Excretion of the compound of the invention, particularly if the Effector is a radionuclide, essentially takes place through the kidneys. Further protection of the kidneys from radioactivity accumulation may be achieved by administration of lysine or arginine or an amino acid solution having a high content of lysine and/or arginine, e.g. a commercially available amino acid solution such as Synthamin®-14 or -10, prior to the injection of or together with the compound of the invention, particularly if the Effector is a radionuclide. Protection of the kidneys may also be achieved by administration of plasma expanders such as e.g. gelofusine, either instead of or in addition to amino acid infusion. Protection of the kidneys may also be achieved by administration of diuretics providing a means of forced diuresis which elevates the rate of urination. Such diuretics include high ceiling loop diuretics, thiazides, carbonic anhydrase inhibitors, potassium-sparing diuretics, calcium-sparing diuretics, osmotic diuretics and low ceiling diuretics. A pharmaceutical composition of the invention may contain, apart from a compound of the invention, at least one of these further compounds intended for or suitable for kidney protection, preferably kidney protection of the subject to which the compound of the invention is administered.

It will be understood by a person skilled in the art that the compound of the invention is disclosed herein for use in various methods. It will be further understood by a person skilled in the art that the composition of the invention and the pharmaceutical composition of the invention can be equally used in said various methods. It will also be understood by a person skilled in the art that the composition of the invention and the pharmaceutical composition are disclosed herein for use in various methods. It will be equally understood by a person skilled in the art that the compound of the invention can be equally used in said various methods.

It will be acknowledged by a person skilled in the art that the composition of the invention and the pharmaceutical composition of the invention contain one or more further compounds in addition to the compound of the invention. To the extent that such one or more further compounds are disclosed herein as being part of the composition of the invention and/or of the pharmaceutical composition of the invention, it will be understood that such one or more further compounds can be administered separately from the compound of the invention to the subject which is exposed to or the subject of a method of the invention. Such administration of the one or more further compounds can be performed prior, concurrently with or after the administration of the compound of the invention. It will also be acknowledged by a person skilled in the art that in a method of the invention, apart from a compound of the invention, one or more further compound may be administered to a subject. Such administration of the one or more further compounds can be performed prior, concurrently with or after the administration of the compound of the invention. To the extent that such one or more further compounds are disclosed herein as being administered as part of a method of the invention, it will be understood that such one or more further compounds are part of a composition of the invention and/or of a pharmaceutical composition of the invention. It is within the present invention that the compound of the invention and the one or more further compounds may be contained in the same or a different formulation. It is also within the present invention that the compound of the invention and the one or more further compounds are not contained in the same formulation, but are contained in the same package containing a first formulation comprising a compound of the invention, and a second formulation comprising the one or more further compounds, whereby the type of formulation may be the same or may be different.

It is within the present invention that more than one type of a compound of the invention is contained in the composition of the invention and/or the pharmaceutical composition of the invention. It is also within the present invention that more than one type of a compound of the invention is used, preferably administered, in a method of the invention.

It will be acknowledged that a composition of the invention and a pharmaceutical composition of the invention may be manufactured in conventional manner.

Radiopharmaceuticals have decreasing content of radioactivity with time, as a consequence of the radioactive decay. The physical half-life of the radionuclide is often short for radiopharmaceutical diagnostics. In these cases, the final preparation has to be done shortly before administration to the patient. This is in particular the case for positron emitting radiopharmaceuticals for Tomography (PET radiopharmaceuticals). It often leads to the use of semi-manufactured products such as radionuclide generators, radioactive precursors and kits.

Preferably, a kit of the invention comprises apart from one or more than one compounds of the invention typically at least one of the followings: instructions for use, final preparation and/or quality control, one or more optional excipient(s), one or more optional reagents for the labeling procedure, optionally one or more radionuclide(s) with or without shielded containers, and optionally one or more device(s), whereby the device(s) is/are selected from the group comprising a labeling device, a purification device, an analytical device, a handling device, a radioprotection device or an administration device.

Shielded containers known as "pigs" for general handling and transport of radiopharmaceutical containers come in various configurations for holding radiopharmaceutical containers such as bottles, vials, syringes, etc. One form often includes a removable cover that allows access to the held radiopharmaceutical container. When the pig cover is in place, the radiation exposure is acceptable.

A labeling device is selected from the group of open reactors, closed reactors, microfluidic systems, nanoreactors, cartridges, pressure vessels, vials, temperature controllable reactors, mixing or shaking reactors and combinations thereof.

A purification device is preferably selected from the group of ion exchange chromatography columns or devices, size-exclusion chromatography columns or devices, affinity chromatography columns or devices, gas or liquid chromatography columns or devices, solid phase extraction columns or devices, filtering devices, centrifugations vials columns or devices.

An analytical device is preferably selected from the group of tests or test devices to determine the identity, radiochemical purity, radionuclidic purity, content of radioactivity and specific radioactivity of the radiolabelled compound.

A handling device is preferably selected from the group consisting of devices for mixing, diluting, dispensing, labeling, injecting and administering radiopharmaceuticals to a subject.

A radioprotection device is used in order to protect doctors and other personnel from radiation when using therapeutic or diagnostic radionuclides. The radioprotection device is preferably selected from the group consisting of devices with protective barriers of radiation-absorbing material selected from the group consisting of aluminum, plastics, wood, lead, iron, lead glass, water, rubber, plastic, cloth, devices ensuring adequate distances from the radiation sources, devices reducing exposure time to the radionuclide, devices restricting inhalation, ingestion, or other modes of entry of radioactive material into the body and devices providing combinations of these measures.

An administration device is preferably selected from the group of syringes, shielded syringes, needles, pumps and infusion devices. Syringe shields are commonly hollow cylindrical structures that accommodate the cylindrical body of the syringe and are constructed of lead or tungsten with a lead glass window that allows the handler to view the syringe plunger and liquid volume within the syringe.

The present invention is now further illustrated by reference to the following figures and examples from which further advantages, features, and embodiments may be taken, wherein FIG. 1 shows the vector map of an exemplary pExoIN2-NTR1 plasmid used to generate the stable HEK293-NTR1 cell lines;

EXAMPLES

Figure 1:
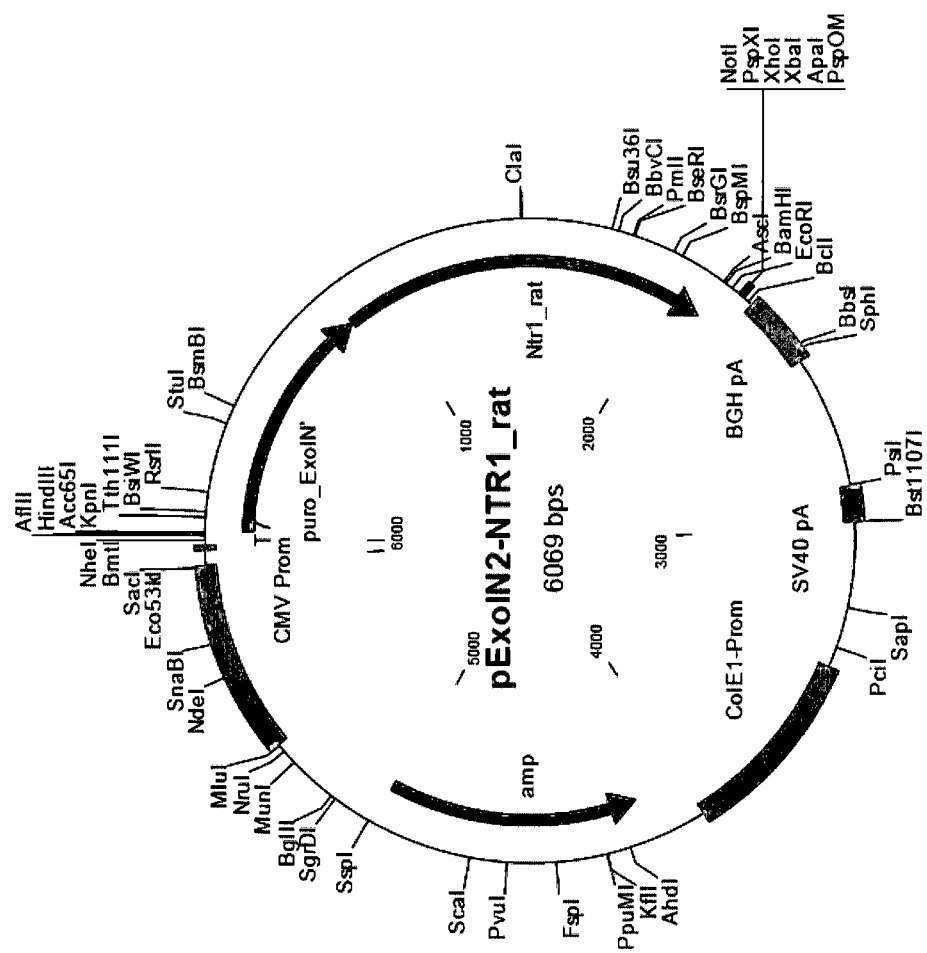
Figure 2:
FIG. 2 shows SPECT-imaging results of $^{111}$In-(IIIa) (A), $^{111}$In-(Va) (B), and $^{111}$In-(IVa) (C) 12 hours post injection.
Figure 2:
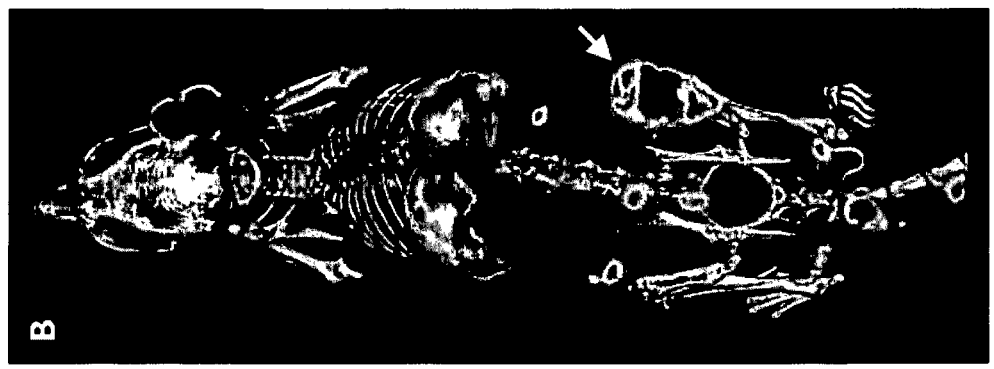
Figure 2:
Figure 3:
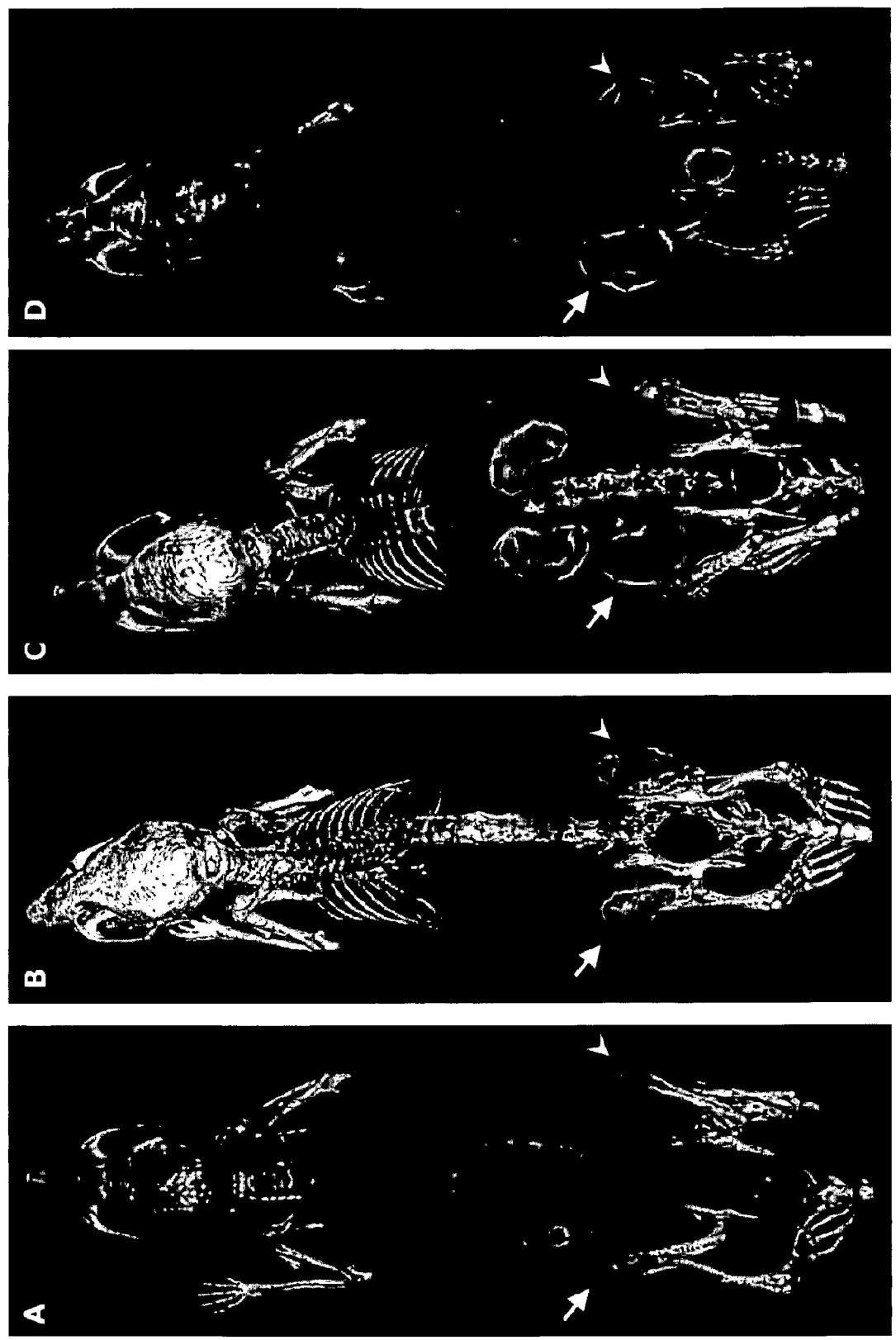
FIG. 3 shows SPECT-imaging results of $^{111}$In-(IIIa) 3 h (A), 6 h (B), 12 h (C), and 24 h (D) post injection. Arrow denotes HT29 tumor, arrowhead denotes Capan-1 tumor.
Figure 4:
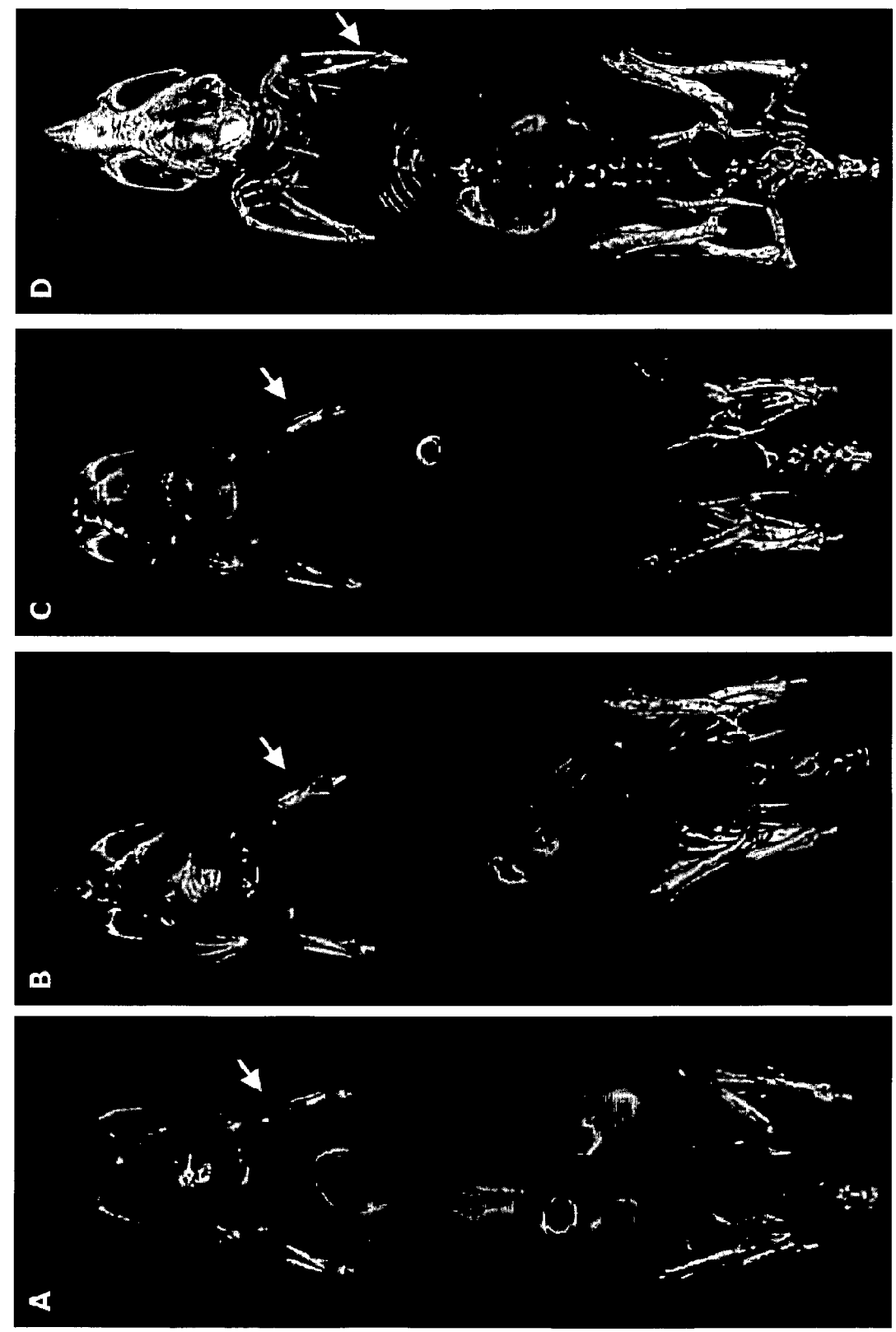
FIG. 4 shows SPECT-imaging results of $^{111}$In-(IIIa) 3 h (A), 6 h (B), 12 h (C), and 24 h (D) post injection. Arrow denotes HEK293 tumor.
Figure 5:
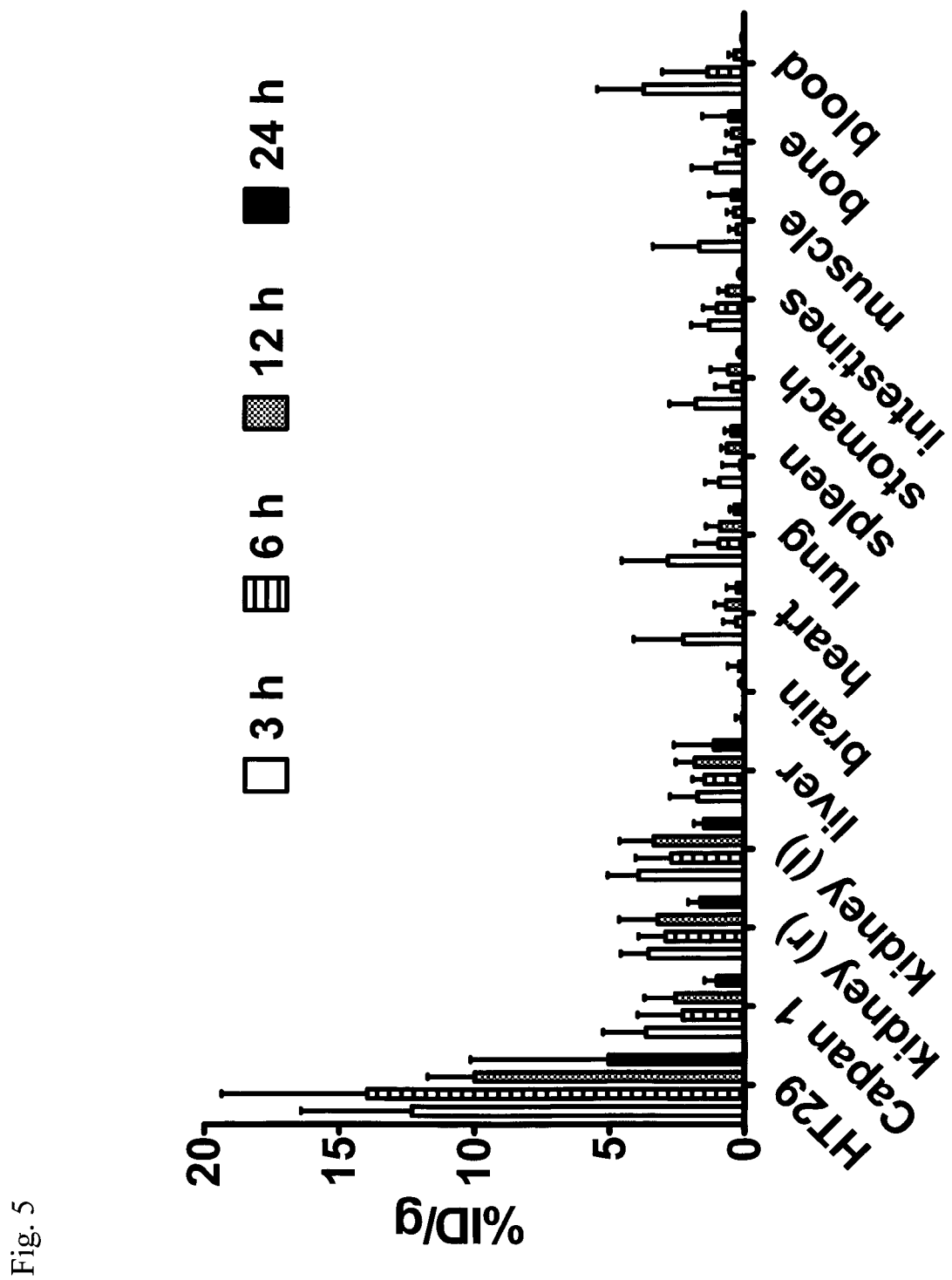
FIG. 5 shows the ex vivo biodistribution results of $^{111}$In-(IIIa) 3 h, 6 h, 12 h, and 24 h post injection in HT29 and Capan-1 tumors and various other organs.
Figure 6:
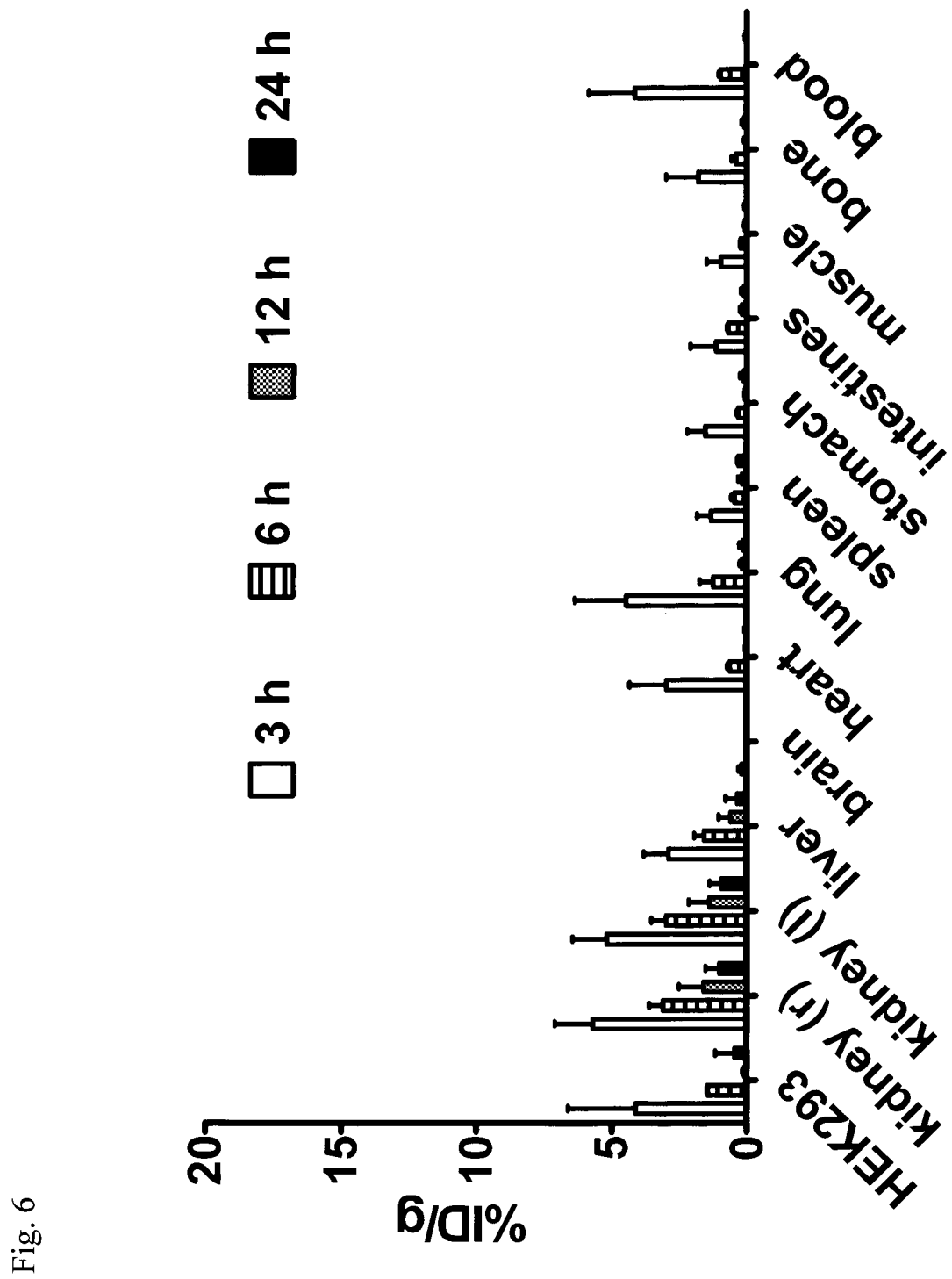
FIG. 6 shows the ex vivo biodistribution results of $^{111}$In-(IIIa) 3 h, 6 h, 12 h, and 24 h post injection in HEK293 tumors and various other organs.

Abbreviations used in the instant application and the following examples in particular are as follows:
5-HT means 5-hydroxytryptamine
5-HT1A means 5-hydroxytryptamine receptor 1A
5-HT1B means 5-hydroxytryptamine receptor 1B
5-HT2A means 5-hydroxytryptamine receptor 2A
5-HT2B means 5-hydroxytryptamine receptor 2B
5-HT-3 means 5-hydroxytryptamine channel 3
5-HT5a means 5-hydroxytryptamine receptor 5a
5-HT6 means 5-hydroxytryptamine receptor 6
5-HT7 means 5-hydroxytryptamine receptor 7
% ID/g means percent injected dose per gram
A1 mean adenosine receptor 1
A2A means adenosine receptor 2A
A3 means adenosine receptor 3
alpha1 means alpha1 adrenergic receptor
alpha2 means alpha2 adrenergic receptor
ACN means acetonitrile
Ahx means 6-Aminohexanoic acid
amu means atomic mass unit
aq. means aqueous
AT1 means angiotensin receptor 1
B2 means bradykinin receptor 2
beta1 means beta1 adrenergic receptor beta2 means beta2 adrenergic receptor
BSA means bovine serum albumin
BZD means benzodiazepine
CB1 means cannabinoid receptor 1
CCK1 means cholecystokinin receptor 1
CCR1 means C—C chemokine receptor type 1
CHO means Chinese hamster ovary
CT means computed tomography
CXCR2 means C—X—C chemokine receptor type 2
D1 means dopamine receptor 1
D2S means dopamine receptor 2S
DCM means dichloromethane
delta2 means delta2 opioid receptor
DFO means N'-{5-[Acetyl(hydroxy)amino]pentyl}-N-[5-({4-[(5-aminopentyl) (hydroxy)amino]-4-oxobutanoyl}amino)pentyl]-N-hydroxysuccinamide
DIC means N,N'-Diisopropylcarbodiimide
DIPEA means diisopropylethylamine
DOTA means 1,4,7,10-tetraazacyclododecane-1,4,7,10-tetraacetic acid
DOTA(tBu)$_3$-OH means Tri-tert-butyl-1,4,7,10-tetraazacyclo-dodecane-1,4,7,10-tetraacetate
DMF means N,N-dimethylformamide
EC50 means half-maximal excitatory concentration
EP4 means prostaglandin e receptor type 4
ETA means endothelin receptor A
Et$_2$O means Diethylether
EtOAc means ethylacetate
Fmoc means 9-Fluorenylmethoxycarbonyl
GABA mean gamma-amino butyric acid
GAL2 means galanin receptor 2
GPCR means G-protein coupled receptor
h means hour(s)
H1 means histamine receptor 1
H2 means histamine receptor 2
HATU means O-(7-azabenzotriazol-1-yl)-N,N,N',N'-tetramethyluronium hexafluorophosphate
HOAc means acetic acid
HOAt means 1-Hydroxy-7-azabenzotriazole
HPLC means high performance liquid chromatography
IC50 means half-maximal inhibitory concentration
kappa means kappa opioid receptor
LC-MS means high performance liquid chromatography coupled with mass spectrometry
LiOH means lithium hydroxide
M1 means muscarinic receptor 1
M2 means muscarinic receptor 2
M3 means muscarinic receptor 3
max. means maximum
MC4 means melanocortin receptor 4
MeOH means Methanol
min means minute(s)
MT1 means melatonin receptor 1
MTBE means Methyl-tert-butylether
mu means mu opioid receptor
NaHCO$_3$ means sodium hydrogencarbonate
NaCl means sodium chloride
Na$_2$SO$_4$ means sodium sulfate
n.d. means not determined
NK2 means neurokinin receptor 2
NK3 means neurokinin receptor 3
NMP means 1-methyl-2-pyrrolidone
NODAGA means 1,4,7-triazacyclononane, 1-glutaric acid-4,7-acetic acid
NOP means nociception receptor
NT means neurotensin
NTR1 means neurotensin receptor 1
PET mean positron emission tomography
prep. means preparative
PyBOP means benzotriazole-1-yl-oxy-tris-pyrrolidino-phosphonium hexafluorophosphate
RLB means radioligand binding assay
RP means reversed phase
RT means room temperature
R$_t$ means retention time
sat. means saturated
SPECT means single photon emission computed tomography
sst means somatostatin receptor
tBu means tert. butyl
TFA means trifluoroacetate or trifluoroacetic acid
TIPS means triisopropylsilane
TLC means thin layer chromatography
Ttds means N-(3-{2-[2-(3-Amino-propoxy)-ethoxy]-ethoxy}-propyl)-succinamic acid
VPAC 1 means vasoactive intestinal polypeptide receptor 1
Y1 means neuropeptide Y receptor 1
Y2 means neuropeptide Y receptor 2

● as used in structural formulas or figures represents a functionalized solid material (solid phase synthesis resin)

Example 1

Material and Methods

The materials and methods as well as general methods are further illustrated by the following examples.
Solvents:
Solvents were used in the specified quality without further purification. Acetonitrile (Gradient grade, Sigma-Aldrich); dichloromethane (AnalaR Normapur, VWR); ethylacetate (laboratory reagent grade, Fisher Scientific); N,N-dimethylformamide (peptide synthesis grade, Biosolve); 1-methyl-2-pyrolidone (biotech. grade, Sigma-Aldrich) 1,4-dioxane (Emplura, Merck); methanol (p. a., Merck).
Water:
Milli-Q Plus, Millipore, demineralized.
Chemicals:
Chemicals were synthesized according to or in analogy to literature procedures or purchased from Sigma-Aldrich-Fluka (Deisenhofen, Germany), Bachem (Bubendorf, Switzerland), VWR (Darmstadt, Germany), Polypeptide (Strasbourg, France), Novabiochem (Merck Group, Darmstadt, Germany), Acros Organics (distribution company Fisher Scientific GmbH, Schwerte, Germany), Iris Biotech (Marktredwitz, Germany), Amatek Chemical (Jiangsu, China), Roth (Karlsruhe, Deutschland), Molecular Devices (Chicago, USA), Biochrom (Berlin, Germany), Peptech (Cambridge, Mass., USA), Synthetech (Albany, Oreg., USA), Pharmacore (High Point, N.C., USA) and Anaspec (San Jose, Calif., USA) or other companies and used in the assigned quality without further purification. $^{177}$Lu-[NT(8-13)-Tle$^{12}$] is DOTA-D-Lys-Ttds-Arg$^8$-Arg$^9$-Pro$^{10}$-Tyr$^{11}$-Tle$^{12}$-Leu$^{13}$-OH and was synthesized according to standard Fmoc-solid-phase-peptide synthesis as described in detail in this reference ("Fmoc Solid Phase Peptide Synthesis" Editors W. Chan, P. White, Oxford University Press, USA, 2000), Fmoc-Ttds-OH is commercially available at Polypeptide (Strasbourg, France).
SR-142948 is (2-[(5-(2,6-Dimethoxy-phenyl)-1-{4-[(3-dimethylamino-propyl)-methyl-carbamoyl]-2-isopropylphenyl}-1H-pyrazole-3-carbonyl)-amino]-adamantane-2-carboxylic acid, >97%) and was purchased from Tocris Bioscience (Bristol, UK).

1-(4-Carboxy-2-isopropyl-phenyl)-5-(2,6-dimethoxy-phenyl)-1H-pyrazole-3-carboxylic acid methyl ester (X) was prepared according to literature procedures as disclosed in U.S. Pat. No. 5,723,483.

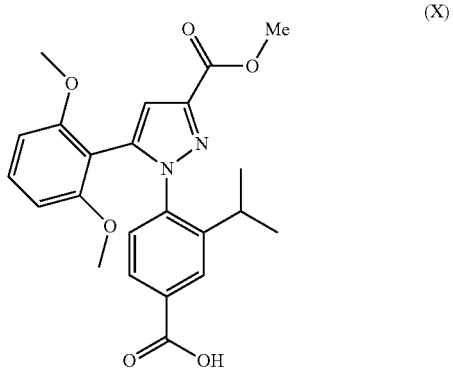 [SMILES: COC(=O)c1cc(-c2c(OC)cccc2OC)n(-c2ccc(C(=O)O)cc2C(C)C)n1]

(X)

Cells:

HT29 (Cat. No. 91072201) were purchased from ECACC and Capan-1 from ATCC (Cat No. HTB-79) cells. HEK293 cells expressing human, murine, and rat NTR1 were produced by Trenzyme (Konstanz, Germany). The cells were stably transfected using an expression system encoded by the pExoIN2 plasmid vector (see FIG. 1) and consisting of hemagglutinin epitope (HA)-tagged puromycin N-acetyl-transferase fused to the N-terminus of ubiquitin, which in turn is fused to the N-terminus of NTR1. This system ensures efficient expression of the transfected protein. The generation of stable cell lines and the pExoIN vector are described in Matentzoglu et al., *BioTechniques*, 2009, 46, 21-28.

Plasticware for biochemical and cell-based assays was purchased from VWR (Darmstadt, Germany).

Concentrations are given as percent by volume unless otherwise stated.

HPLC/MS analyses were performed by injection of 5 μl of a solution of the sample, using a 2 step gradient for all chromatograms (5-50% B in 5 min, followed by 50-100% B in 2 min, A: 0.05% TFA in water and B: 0.05% TFA in ACN). RP columns were from Phenomenex (Type Luna C-18, 3 μm, 50×2.00 mm, flow 0.5 ml, HPLC at room temperature); Mass spectrometer: Thermo Finnigan Advantage and/or LCQ Classic (both ion trap), ESI ionization, helium served as impact gas in the ion trap. Excalibur version 1.4 was used as software. UV detection was done at λ=230 nm. Retention times ($R_t$) are indicated in the decimal system (e.g. 1.9 min=1 min 54 s) and are referring to detection in the mass spectrometer. The dead time between injection and UV detection (HPLC) was 0.45 min, and for the delay between UV detection and mass detection was corrected in the chromatogram. The accuracy of the mass spectrometer was approx. ±0.5 amu.

Preparative HPLC:

Preparative HPLC separations were done with the columns and gradients described in the individual examples. For the gradient the following solvents were used:

A: 0.05% TFA in $H_2O$

B: 0.05% TFA in ACN

A linear binary gradient was used in all separations. For instance: If the gradient is described as: "20 to 60% B in 30 min", this means a linear gradient from 20% B (and 80% A) up to 60% B (and 40% A) within 30 min. The flow-rate depends on the column size: For 25 mm diameter of the column it is 30 ml/min and for 50 mm diameter of the column it is 60 ml/min, respectively.

Compounds were named using AutoNom version 2.2 (Beilstein Informationssysteme Copyright© 1988-1998, Beilstein Institut für Literatur der Organischen Chemie licensed to Beilstein Chemiedaten and Software GmbH). Preferably, in case of chelator-containing compounds the chelator was referred to by its commonly accepted abbreviation rather than the full systematic name in order to avoid unnecessarily complex names. In case of compounds containing a protected form of the chelator the corresponding chelator abbreviation together with the name and number of the protecting group in parentheses is preferably used. For instance, if the chelator is DOTA, the abbreviation DOTA- or DOTA(tBu)$_3$- in the molecule name means that the DOTA-moiety or its three time tert. butyl protected form is covalently attached to a designated position of the molecule by one of its carboxylic acid groups. In most of the cases the carboxylic acid group of a chelator is utilized for the attachment to the molecule. But, if the chelator is DFO the abbreviation DFO- in the name means that the amino group of DFO is covalently attached to a designated position of the molecule. However, someone skilled in the art will easily understand which functional groups or atoms of a chelator are capable of forming the respective covalent attachment to the molecule. These conventions apply not only to the compounds as recited in the example part of the instant description but to each and any part thereof, including the claims.

Preparation of Compounds:

The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are incorporated herein by reference.

Specific embodiments for the preparation of compounds of the invention are provided in the following examples. Unless otherwise specified all starting materials and reagents are of standard commercial grade, and are used without further purification, or are readily prepared from such materials by routine methods. Those skilled in the art of organic synthesis will recognize in light of the instant disclosure that starting materials and reaction conditions may be varied including additional steps employed to produce compounds encompassed by the present invention.

Example 2

Synthesis of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester Bound to Trityl Resin (XVIII)

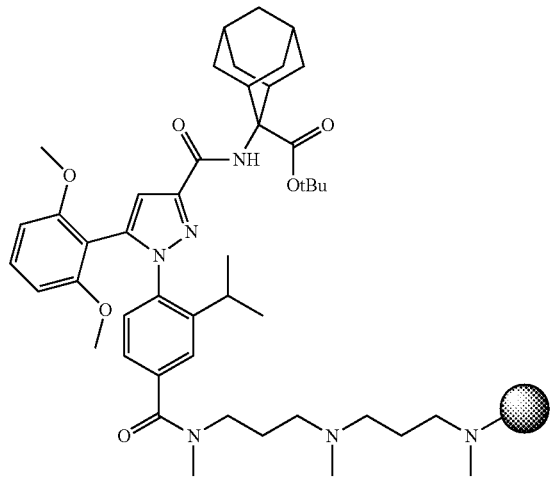

(XVIII)

Figure 7:
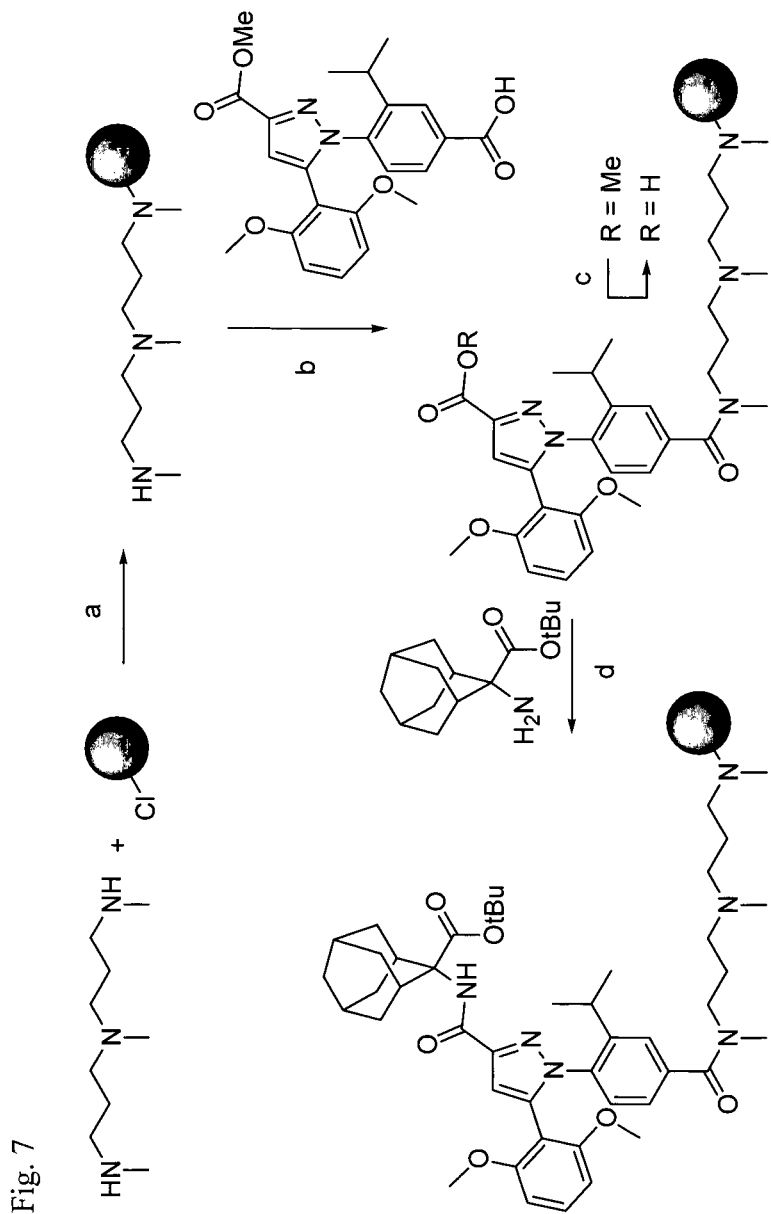
FIG. 7 shows the solid phase synthesis of derivatized resin of formula (XVIII)

A. Loading of chlorotrityl polystyrene resin with N,N-Bis[3-(methylamino)-propyl]methylamine (FIG. 7 step a)

Tritylchloride polystyrene resin (initial loading 1.8 mmol/g, 1.11 g, 2 mmol, 1.0 eq.) was swollen in DCM for 30 min. Then N,N-Bis[3-(methylamino)-propyl]methylamine (1.6 ml, 8 mmol, 4 eq.) in DCM (6.5 ml) was added to the resin and the mixture was shaken overnight. Afterwards the resin was washed successively with DMF, DCM and diethyl ether (5/3/1) and dried in the vacuum.

B. Coupling of 1-(4-Carboxy-2-isopropyl-phenyl)-5-(2,6-dimethoxy-phenyl)-1H-pyrazole-3-carboxylic acid methyl ester (FIG. 7 step b)

N,N-Bis[3-(methylamino)-propyl]methylamine charged trityl resin (1 g, 1.8 mmol, 1.0 eq.) was swollen in DMF for 30 min. The resin was washed with DMF/DIPEA (9/1) (to remove residual N,N-Bis[3-(methylamino)-propyl]methylamine hydrochloride) and DMF (3/3). 1-(4-Carboxy-2-isopropyl-phenyl)-5-(2,6-dimethoxy-phenyl)-1H-pyrazole-3-carboxylic acid methyl ester (X) (1.15 g, 2.7 mmol, 1.5 eq.) [prepared as disclosed in U.S. Pat. No. 5,723,483], HATU (1.03 g, 2.7 mmol, 1.5 eq.) and DIPEA (937 µl, 5.4 mmol, 3 eq.) were dissolved in DMF (18 ml) and mixed thoroughly for 1 min. After addition of the activated building block the resin was shaken overnight. The resin was washed (DMF five times, DCM three times and diethyl ether) and dried in the vacuum. The completeness of the reaction was assured as follows: A resin sample was treated with a solution of benzoic acid, HATU and DIPEA (1/1/2) in DMF for 30 min. After washing with DMF and DCM, TFA was added to the resin. Absence of the benzoic acid N,N-Bis[3-(methyl-amino)-propyl]methyl amide in LC-MS indicated absence of free amino functions on the resin thus providing evidence of the completed coupling of 1-(4-Carboxy-2-isopropyl-phenyl)-5-(2,6-dimethoxy-phenyl)-1H-pyrazole-3-carboxylic acid methyl ester.

C. Hydrolysis of the Methylester (FIG. 7 Step c)

The resin (1.64 g, 1.75 mmol, 1.0 eq.) described before was treated overnight with dioxane (35 ml) and LiOH hydrate (689 mg, 16 mmol, 10 eq.) in water (12 ml). The procedure was repeated once, the resin was subsequently washed with water, DMF and DCM (3/3/3) and dried in the vacuum.

D. Coupling of 2-Amino-adamantane-2-carboxylic acid tert-butyl ester (FIG. 7 Step d)

The resin (0.7 g, 0.75 mmol, 1.0 eq.) described before was swollen in DMF for 30 min. Then HOAt (153 mg, 1.13 mmol, 1.5 eq.), DIC (232 µl, 1.5 mmol, 2.0 eq.) and 2-amino-adamantane-2-carboxylic acid tert-butyl ester (942 mg, 3.75 mmol, 5.0 eq.) were dissolved in a mixture of DMF and DCM (2:1) (6 ml) and subsequently added to the resin. After 2.5 hours additional DIC (232 µl, 1.5 mmol, 2.0 eq.) was added. The resin was left to shake for 60 hours after which the reaction was complete. Afterwards the resin was washed with DMF and DCM (3/3) and dried in the vacuum.

Example 3

Synthesis of 2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX)

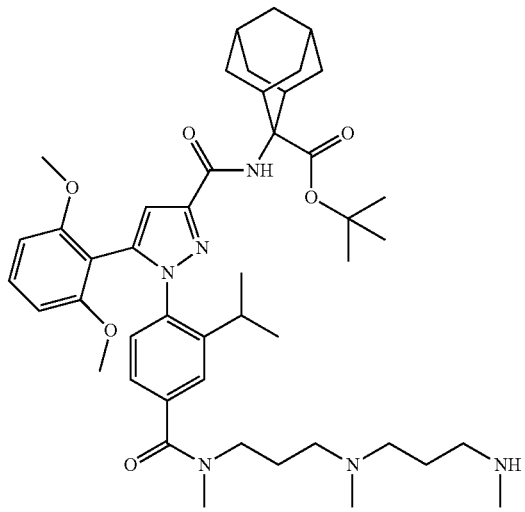

(XIX)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester resin (XIX) (0.7 g, 0.75 mmol, 1.0 eq.) was treated four times with a mixture of TFA, TIPS and DCM (2/5/93). To prevent premature loss of the DOTA protecting groups the resulting solutions were immediately poured into aqueous buffer solution (10 ml, pH=8, 100 mM NH$_4$(CO$_3$)$_2$). All DCM-buffer mixtures were combined and the organic layer reduced to a minimum by evaporation. To the remaining aqueous solution ACN (5 ml)

was added and the mixture was freeze-dried to yield 800 mg of crude product. The residue was subjected to HPLC purification (15 to 45% B in 30 min, Agilent PLRP-S 25×150 mm) to give the title compound (210 mg, 26.3 μmol, 35.0%). HPLC: $R_t$=5.5 min. MS: m/z=799.4 ([M+H]$^+$, calculated 799.5). $C_{46}H_{66}N_6O_6$ (MW=799.05).

Example 4

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (III)

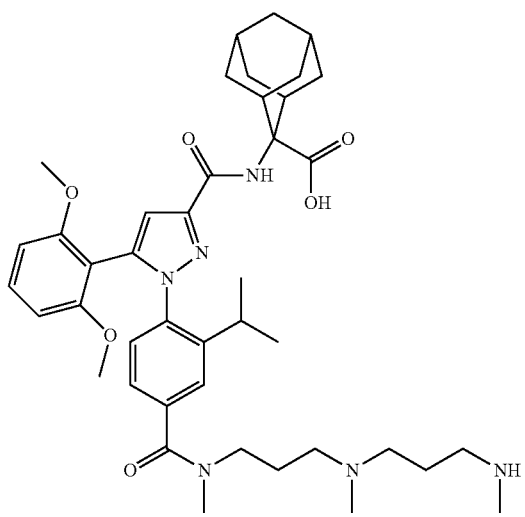

(III)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester resin (XIX) (0.7 g, 0.75 mmol, 1.0 eq.) was treated with a mixture of TFA and DCM (1/4) for 2 h. The cleavage solution was evaporated to dryness to yield 709 mg of crude product.

The residue was purified by HPLC (20 to 50% B in 30 min, Agilent PLRP-S 25×150 mm) to give the title compound (155.5 mg, 0.21 mmol, 28%). HPLC: $R_t$=4.7 min. MS: m/z=743.4 ([M+H]$^+$, calculated 742.4). $C_{42}H_{57}N_6O_6$ (MW=741.94).

Example 5

Synthesis of 2-{[1-{4-[(3-{[3-(DOTA-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-adamantane-2-carboxylic acid (IIIa)

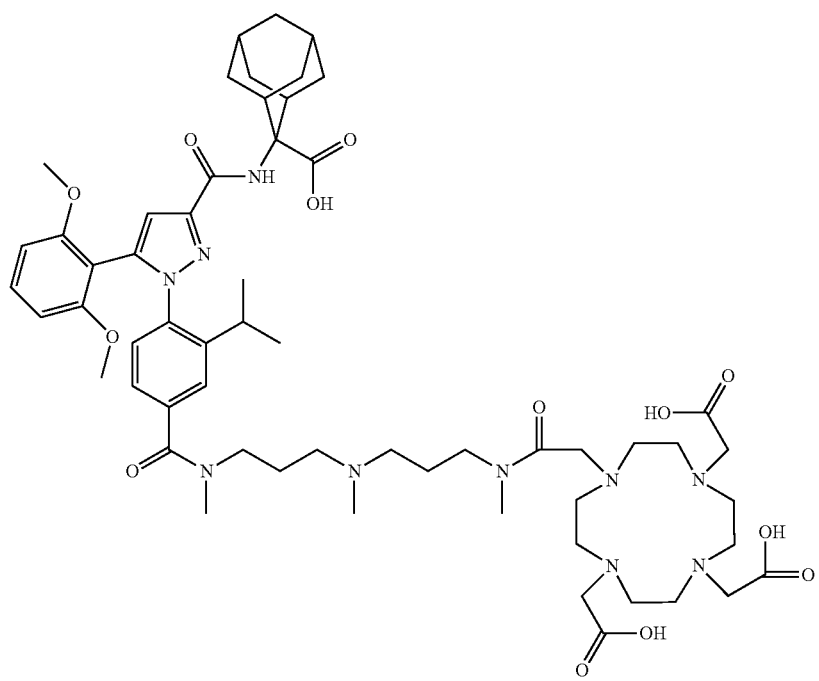

(IIIa)

A. 1-{4-[(3-{[3-(DOTA(tBu)₃-methyl-amino)-propyl]-methyl-amino}-propyl)-methyl-carbamoyl]-2-isopropyl-phenyl}-5-(2,6-dimethoxy-phenyl)-1H-pyrazole-3-carboxylic acid methyl ester (XI)

DOTA(tBu)₃-OH (500 mg, 0.873 mmol, 1.0 eq.) was dissolved in dry DMF (5 ml). After adding N,N'-Dimethyl-N-(3-methylamino-propyl)-propane-1,3-diamine (3.5 ml, 17.5 mmol, 20 eq.) and DIPEA (0.389 ml, 2.27 mmol, 2.6 eq.) the mixture was cooled to 0° C. PyBOP (590 mg, 1.13 mmol, 1.3 eq.) was dissolved in dry DMF (5 ml). 0.5 ml of this PyBOP solution was added every 5 to 10 min to the reaction mixture until all the solution was added. After 1 h DMF was removed under vacuum. The remaining residue was dissolved in EtOAc (100 ml) and extracted with water (5×5 ml). The organic layer was dried over Na₂SO₄ and evaporated to yield 1.01 g crude material.

This crude material (1.01 g, max. 0.873 mmol) was dissolved in dry DMF (4 ml). In a separate flask 1-(4-Carboxy-2-isopropyl-phenyl)-5-(2,6-dimethoxy-phenyl)-1H-pyrazole-3-carboxylic acid methyl ester (X) (445 mg, 1.05 mmol, 1.2 eq.) [prepared as disclosed in U.S. Pat. No. 5,723,483] was dissolved in dry DMF (2.5 ml). HATU (398 mg, 1.05 mmol, 1.2 eq.) and DIPEA (0.359 ml, 2.10 mmol, 2.4 eq.) were added sequentially and the reaction was stirred for ten minutes. The dissolved crude material from the first step (DOTA modified diamine), was added dropwise to this HATU-activated carboxylic acid solution. After 1 h additional HATU-activated carboxylic acid solution was added [carboxylic acid of formula (X) (102 mg, 0.24 mmol, 0.27 eq.) in dry DMF (0.5 ml), HATU (91 mg, 0.24 mmol, 0.27 eq.) DIPEA (0.082 ml, 0.48 mmol, 0.55 eq.), 10 min preactivation]. After 15 h additional preactivated carboxylic acid of formula (X) was added [carboxylic acid of formula (X) (148 mg, 0.35 mmol, 0.40 eq.) in dry DMF (0.75 ml), HATU (133 mg, 0.35 mmol, 0.40 eq.), DIPEA (0.120 ml, 0.698 mmol, 0.80 eq.) 10 min pre-activation]. 2 h after the last addition DMF was evaporated and the residual solvents were removed under high-vacuum.

The residual oil was dissolved in ACN/water 1/1 (ca. 10 ml) and separated by prep. HPLC (20 to 60% B in 30 min, Agilent PLRP-S 50×150 mm) to give the title compound (585 mg, 0.516 mmol, 59%). HPLC: $R_t$=5.4 min. MS: m/z=1134.7 ([M+H]⁺, calculated 1134.7). $C_{60}H_{95}N_9O_{12}$ (MW=1134.45).

B. 1-{4-[(3-{[3-(DOTA(tBu)₃-methyl-amino)-propyl]-methyl-amino}-propyl)-methyl-carbamoyl]-2-isopropyl-phenyl}-5-(2,6-dimethoxy-phenyl)-1H-pyrazole-3-carboxylic acid (XII)

Methylester of formula (XI) (294 mg, 0.259 mmol) was dissolved in 1,4-dioxane (1.35 ml). A 1 M aqueous solution of LiOH (1.04 ml, 1.04 mmol, 4 eq.) was added dropwise. After stirring for 5 h the pH was adjusted to 5-6 with HOAc (0.373 ml). After addition of ACN (18 ml) and water (225 ml) the cloudy solution was subjected to a solid phase extraction column (3.0 g Varian Bondesil-ENV in a 60 ml polystyrene syringe, prewashed with methanol (3×20 ml) and water (3×20 ml). The column was eluted with 60 ml of 10% ACN in water as first fraction and each of the next fractions were eluted with 60 ml of 50% ACN in water containing 0.1% TFA. After lyophylization of the fractions 3 to 8 the title compound (248 mg, 86%) was obtained. HPLC: $R_t$=4.9 min. MS: m/z=1120.7 ([M+H], calculated 1120.7). $C_{59}H_{93}N_9O_{12}$ (MW=1120.42).

C. 2-{[1-{4-[(3-{[3-(DOTA(tBu)₃-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-adamantane-2-carboxylic acid (XIII)

Carboxylic acid of formula (XII) (248 mg, 0.222 mmol) was dissolved in dry NMP (3 ml). HATU (84.3 mg, 0.222 mmol, 1.0 eq.) was added as solid. To this mixture DIPEA (76 µl, 0.443 mmol, 2.0 eq.) was added. After stirring for 5 min this solution was transferred within 5 min to a suspension of 2-amino-adamantane-2-carboxylic acid (43.3 mg, 0.222 mmol, 1.0 eq.) in dry NMP (6.5 ml). After 1 h at room temperature the flask was heated with an oil bath at 65° C. bath temperature. After 6 h DIPEA (38 µl, 0.222 mol, 1.0 eq.) was added and heating was continued for additional 18 h. After cooling down ACN/water 1:1 was added and the solution was lyophylized. 100 µl DMSO/200 µl HOAc and 1 ml ACN were added to the remaining solid and the suspension was filtered. The filtrate was separated by prep. HPLC (20 to 60% B in 30 min, Agilent PLRP-S 25×150 mm) and the title compound (74 mg, 0.057 mmol, 26% yield) was obtained. HPLC: $R_t$=5.1 min. MS: m/z=1297.7 ([M+H]⁺, calculated 1197.8). $C_{70}H_{108}N_{10}O_{13}$ (MW=1297.67).

D. 2-{[1-{4-[(3-{[3-(DOTA-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-adamantane-2-carboxylic acid (IIIa)

TFA (9 ml) was added to a solution of Tris-tBu-ester of formula (XIII) (74 mg, 0.057 mmol) and triisobutylsilane (600 µl) in dry DCM (2.4 ml). After 5 h at room temperature the mixture was evaporated under reduced pressure and purified by prep. HPLC (15 to 50% B in 30 min, Agilent PLRP-S 25×150 mm). This yielded the title compound (43 mg, 0.038 mmol, 66% yield) as TFA-salt. HPLC: $R_t$=5.3 min. MS: m/z=1129.7 ([M+H]⁺, calculated 1129.6). $C_{58}H_{84}N_{10}O_{13}$ (MW=1129.35).

Example 6

Synthesis of DOTA-Transition Metal Complexes

A. General Procedure for the Synthesis of DOTA-Transition Metal-Complexes

A 1 mM solution of the corresponding metal salt (3.0 eq. to 5.0 eq.) was diluted with the 5-fold volume of acetate buffer (pH 5.0, 0.4 M). This solution was added to the DOTA-containing compound (3 to 10 mg, 1.0 eq.). The reaction was positioned in an oil bath (90° C. bath temperature). After 20 min the reaction mixture was cooled to RT and applied to a solid phase extraction column (250 mg Varian Bondesil-ENV in a 15 ml polystyrene syringe, pre-washed with methanol (1×5 ml) and water (2×5 ml). The column was eluted with water (2×5 ml), 5 ml of 50% ACN in water as first fraction and each of the next fractions were eluted with 5 ml of 50% ACN in water containing 0.1% TFA. The fractions containing the pure product were pooled and freeze dried.

B. Indium-Complex of a Compound of Formula (IIIa): In-(IIIa)

Complex formation was done according to the general procedure (Example 6 A) using the following reagents: Compound of formula (IIIa) (5.0 mg), InCl$_3$×4 H$_2$O (3.9 mg) yielding the title compound (4.26 mg, 3.4 μmol, 78%). HPLC: R$_t$=4.4 min. MS: m/z=1241.6 ([M+H]$^+$, calculated 1241.5). C$_{58}$H$_{81}$InN$_{10}$O$_{13}$ (MW=1241.14).

C. Gallium-Complex of a Compound of Formula (IIIa): Ga-(IIIa)

Complex formation was done according to the general procedure (Example 6 A) using the following reagents: Compound of formula (IIIa) (3.0 mg) and Ga(NO$_3$)$_3$ hydrate (3.9 mg), yielding the title compound (2.61 mg, 2.2 μmol, 82%). HPLC: R$_t$=4.4 min. MS: m/z=1195.6 ([M+H]$^+$, calculated 1195.5). C$_{58}$H$_{81}$GaN$_{10}$O$_{13}$ (MW=1196.05).

D. Yttrium-Complex of a Compound of Formula (IIIa): Y-(IIIa)

Complex formation was done according to the general procedure (Example 6 A) using the following reagents: Compound of formula (IIIa) (3.0 mg) and Y(NO$_3$)$_3$×6H$_2$O (3.1 mg), yielding the title compound (2.54 mg, 2.1 μmol, 79%). HPLC: R$_t$=4.5 min. MS: m/z=1215.6 ([M+H]$^+$, calculated 1215.5). C$_{58}$H$_{81}$N$_{10}$O$_{13}$Y (MW=1216.24).

E. Lutetium-Complex of a Compound of Formula (IIIa): Lu-(IIIa)

Complex formation was done according to the general procedure (Example 6 A) using the following reagents: Compound of formula (IIIa) (3.0 mg) and LuCl$_3$ (2.2 mg), yielding the title compound (2.88 mg, 2.2 mol, 83%). HPLC: R$_t$=4.4 min. MS: m/z=1301.5 ([M+H]$^+$, calculated 1301.5). C$_{58}$H$_{81}$LuN$_{10}$O$_{13}$ (MW=1301.30).

Example 7

2-{[1-(4-{[3-({3-[(DOTA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIb)

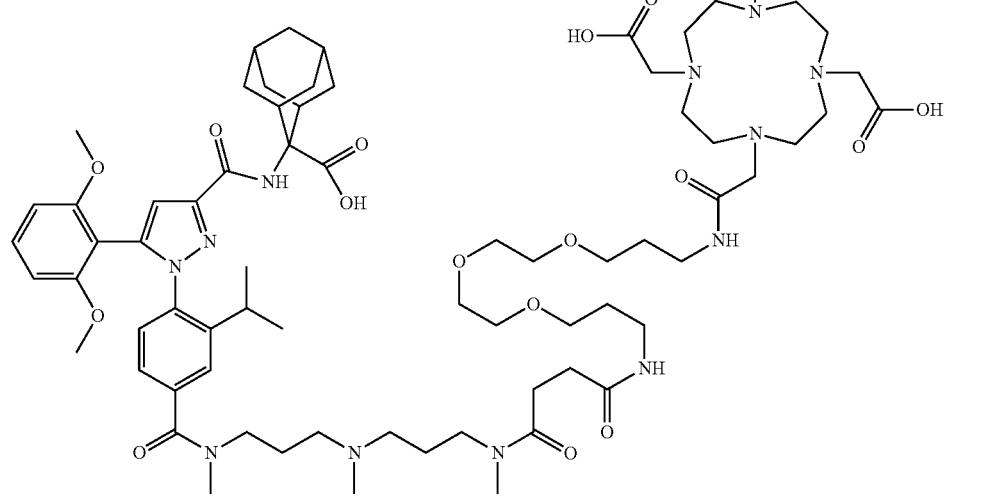

(IIIb)

A. Synthesis of N-{3-[2-(2-{3-[2-(4,7,10-Tris-tert-butoxycarbonylmethyl-1,4,7,10-tetraaza-cyclododec-1-yl)-acetylamino]-propoxy}-ethoxy)-ethoxy]-propyl}-succinamic acid (DOTA(tBu)$_3$-Ttds-OH) (XX)

After chlorotrityl resin (167 mg, 0.3 mmol, 1.0 eq.) had been swollen in DCM for 1 h, a solution of Fmoc-Ttds-OH (326 mg, 0.6 mmol, 2.0 eq.) and DIPEA (155 µl, 0.9 mmol, 3.0 eq.) in DCM (4 ml) was added. After 2.5 h the solution was filtered off and the resin successively washed with DCM, MeOH, DCM and DMF (1/1/1/3). The resin was treated twice with 20% piperidine in DMF (2 min and 20 min) and washed five times with DMF afterwards. Next a mixture of Tri-tert-butyl-1,4,7,10-tetraazacyclo-dodecane-1,4,7,10-tetraacetate (DOTA(tBu)$_3$-OH) (322 mg, 0.56 mmol, 1.9 eq.), HATU (214 mg, 0.56 mmol, 1.9 eq.) and DIPEA (195 µl, 1.13 mmol, 3.8 eq.) was shaken for 5 min and subsequently added to the resin. After agitation for 2 h the resin was washed with DMF and DCM (5/2) and subsequently dried in the vacuum. The resin was treated four times with a mixture of TFA, TIPS and DCM (5/5/90) for 5 min. To prevent premature loss of the DOTA protecting groups the resulting solutions were immediately poured into aqueous buffer solution (10 ml, pH=8, 100 mM NH$_4$(CO$_3$)$_2$). The pH value of the mixture was kept above pH=7 by addition of 4N NaOH solution. DCM-buffer mixtures containing the target compound were combined, the phases were separated, the aqueous phase was extracted twice with DCM and the organic phase was evaporated to dryness. The residue was redissolved in ACN/water (1/1) and lyophilized.

The residue was purified by HPLC (15 to 45% B in 30 min, Agilent PLRP-S 25×150 mm) to give the title compound (118.6 mg, 0.136 mmol, 45%). HPLC: R$_t$=4.3 min. MS: m/z=875.5 ([M+H]$^+$, calculated 875.6). C$_{42}$H$_{78}$N$_6$O$_{13}$ (MW=875.10).

B. Synthesis of 2-{[1-(4-{[3-({3-[(DOTA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIb)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX) (24.9 mg, 31.1 µmol, 1 eq.) was dissolved in DMF (0.5 ml). DIPEA (32.4 µl, 187 µmol, 6 eq.) was added to the solution to adjust the pH-value to pH=7. N-{3-[2-(2-{3-[2-(4,7,10-Tris-tert-butoxycarbonylmethyl-1,4,7,10-tetraaza-cyclododec-1-yl)-acetylamino]-propoxy}-ethoxy)-ethoxy]-propyl}-succinamic acid (DOTA(tBu)$_3$-Ttds-OH) (XX) (30.0 mg, 34.3 µmol, 1.1 q eq.) was added to the solution, followed by HOAt (16.9 mg, 124.4 µmol, 4 eq.) and DIC (14.5 µl, 93.3 µmol, 3 eq.). After stirring the mixture for 24 h the solvent was removed by evaporation. To the remaining residue water (1 ml) and EtOAc (2 ml) were added. The organic phase was separated, dried and evaporated. The remainder was treated with TFA, phenol, water and TIPS (18/1/1/2) (330 µl) for 8 h. All volatiles were removed on the vacuum.

The residue was purified by HPLC (15 to 45% B in 30 min, Agilent PLRP-S 25×150 mm) to give the title compound (7.0 mg, 4.9 µmol, 15.8%). HPLC: R$_t$=4.7 min. MS: m/z=1431.9 ([M+H]$^+$, calculated 1431.8). C$_{72}$H$_{110}$N$_{12}$O$_{18}$ (MW=1431.71).

Example 8

Lutetium-Complex of IIIb: Lu-(IIIb)

Complex formation was done according to the general procedure (Example 6 A) using the following reagents: Compound of formula (IIIb) (4.0 mg) and LuCl$_3$ (2.35 mg), yielding the title compound (2.61 mg, 1.6 µmol, 57%). HPLC: R$_t$=4.7 min. MS: m/z=1603.8 ([M+H]$^+$, calculated 1603.7). C$_{72}$H$_{107}$LuN$_{12}$O$_{18}$ (MW=1603.66).

Example 9

2-{[1-(4-{[3-({3-[(DOTA-Ahx)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIc)

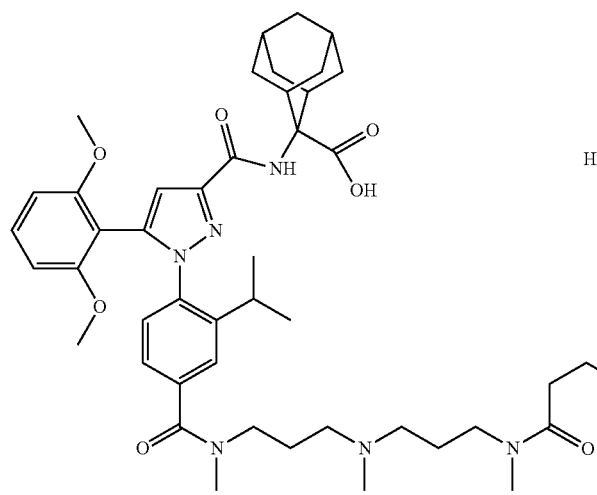
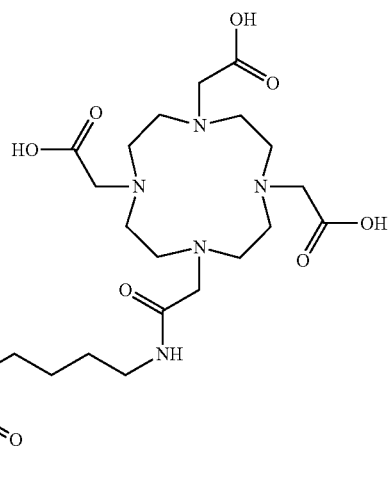

(IIIc)

A. Synthesis of 6-[2-(4,7,10-Tris-tert-butoxycarbonylmethyl-1,4,7,10-tetraaza-cyclododec-1-yl)-acetylamino]-hexanoic acid (DOTA(tBu)₃-Ahx-OH) (XXI)

After chlorotrityl resin (167 mg, 0.3 mmol, 1.0 eq.) had been swollen in DCM for 1 h, a solution of Fmoc-Ahx-OH (212 mg, 0.6 mmol, 2.0 eq.) and DIPEA (155 µl, 0.9 mmol, 3.0 eq.) in DCM (4 ml) was added. After 1 h the solution was filtered off and the resin successively washed with DCM, MeOH, DCM and DMF (1/1/1/3). The resin was treated twice with 20% piperidine in DMF (2 min and 20 min) and washed five times with DMF afterwards. Next a mixture of Tri-tert-butyl 1,4,7,10-tetraazacyclo-dodecane-1,4,7,10-tetraacetate (DOTA(tBu)₃-OH, 322 mg, 0.56 mmol, 1.9 eq.), HATU (214 mg, 0.56 mmol, 1.9 eq.) and DIPEA (195 µl, 1.13 mmol, 3.8 eq.) was shaken for 5 min and subsequently added to the resin. After agitation for 4 h the resin was washed with DMF and DCM (5/2) and subsequently dried in the vacuum. The resin was treated four times with a mixture of TFA, TIPS and DCM (5/5/90) for 5 min. To prevent premature loss of the DOTA protecting groups the resulting solutions were immediately poured into aqueous buffer solution (10 ml, pH=8, 100 mM NH₄(CO₃)₂). The pH value of the mixture was kept above pH=7 by addition of 4N NaOH solution. All DCM-buffer mixtures were combined, the phases were separated, the aqueous phase was extracted twice with DCM and the organic phase was evaporated to dryness. The residue was re-dissolve in ACN/water (1/1) and lyophilized to yield 185 mg of crude product.

The residue was dissolved in water and a minimal amount of ACN and subjected to HPLC purification (20 to 45% B in 30 min, Agilent PLRP-S 25×150 mm) to give the title compound (86.2 mg, 0.125 mmol, 42%). HPLC: $R_t$=4.5 min. MS: m/z=686.3 ([M+H]⁺, calculated 686.5). $C_{34}H_{63}N_5O_9$ (MW=685.89).

B. Synthesis of 2-{[1-(4-{[3-({3-[(DOTA-Ahx)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIc)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX) (12.7 mg, 15.9 µmol, 1 eq.) was dissolved in DMF (0.3 ml). DIPEA (16.6 µl, 95.4 µmol, 6 eq.) was added to the solution to adjust the pH-value to pH=7. 6-[2-(4,7,10-Tris-tert-butoxycarbonylmethyl-1,4,7,10-tetraaza-cyclododec-1-yl)-acetylamino]-hexanoic acid (DOTA(tBu)₃-Ahx-OH) (XXI) (16.4 mg, 23.85 µmol, 1.5 eq.) was added to the solution, followed by HOAt (8.7 mg, 63.6 µmol, 4 eq.) and DIC (7.4 µl, 47.7 µmol, 3 eq.). After stirring the mixture for 72 h the solvent was removed by evaporation. To the remaining residue water (1 ml) and EtOAc (2 ml) were added. The organic phase was separated, dried and evaporated. The remainder was treated with TFA, phenol, water and TIPS (18/1/1/2) (330 µl) for 8 h. All volatiles were removed in the vacuum.

The residue was purified by HPLC (20 to 50% B in 30 min, Agilent PLRP-S 25×150 mm) to give the title compound (7.78 mg, 6.3 µmol, 39.4%). HPLC: $R_t$=4.6 min. MS: m/z=1242.8 ([M+H]⁺, calculated 1242.7). $C_{64}H_{95}N_{11}O_{14}$ (MW=1242.50).

Example 10

2-{[1-(4-{[3-({3-[(NODAGA)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid

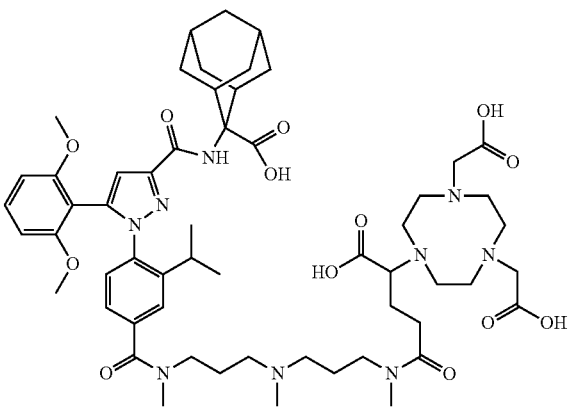

(IIId)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid tert-butyl ester (XIX) (13.4 mg, 16.7 µmol, 1 eq.) was dissolved in DMF (0.3 ml). DIPEA (17.4 µl, 100 µmol, 6 eq.) was added to the solution to adjust the pH-value to pH=7. 2-(4,7-Bis-tert-butoxycarbonylmethyl-[1,4,7]triazonan-1-yl)-pentanedioic acid 1-tert-butyl ester (NODAGA(tBu)₃-OH) (10.0 mg, 18.4 µmol, 1.1 eq.) was added to the solution, followed by HOAt (9.1 mg, 66.8 µmol, 4 eq.) and DIC (7.8 µl, 50.1 µmol, 3 eq.). After stirring the mixture for 24 h the solvent was removed by evaporation. To the remaining residue water (1 ml) and EtOAc (2 ml) were added. The organic phase was separated, dried and evaporated. The remainder was treated with TFA, phenol, water and TIPS (90/5/5/3) (1030 µl) for 5.5 h. Subsequently all volatiles were removed in the vacuum.

The residue was purified by HPLC (20 to 50% B in 30 min, Agilent PLRP-S 25×150 mm) to give the title compound (7.64 mg, 6.9 µmol, 41.6%). HPLC: $R_t$=4.9 min. MS: m/z=1100.7 ([M+H]⁺, calculated 1100.6). $C_{57}H_{81}N_9O_{13}$ (MW=1100.31).

Example 11

Gallium-Complex of a Compound of Formula (IIId): Ga-(IIId)

Complex formation was done according to the general procedure (Example 6 A) using the following reagents: Compound of formula (IIId) (10.0 mg) and Ga(NO₃)₃ hydrate (7.47 mg), yielding the title compound (7.46 mg, 6.4 µmol, 70%). HPLC: $R_t$=4.8 min. MS: m/z=1166.6 ([M+H]⁺, calculated 1166.5). $C_{57}H_{78}GaN_9O_{13}$ (MW=1167.0).

Example 12

2-{[1-(4-{[3-({3-[(NODAGA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIe)

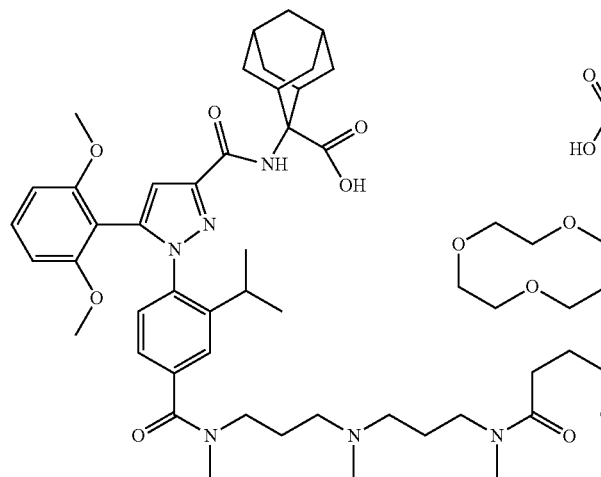
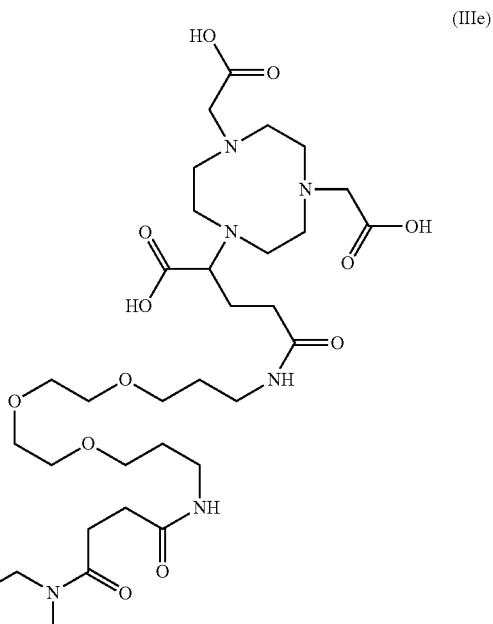

(IIIe)

A. Synthesis of 2-(4,7-Bis-tert-butoxycarbonylmethyl-[1,4,7]triazonan-1-yl)-4-[3-(2-{2-[3-(3-carboxy-propionylamino)-propoxy]-ethoxy}-ethoxy)-propylcarbamoyl]-butyric acid tert-butyl ester (NODAGA(tBu)$_3$-Ttds-OH) (XXII)

After chlorotrityl resin (556 mg, 1.0 mmol, 1.0 eq.) had been swollen in DCM for 1 h, a solution of Fmoc-Ttds-OH (1085 mg, 2.0 mmol, 2.0 eq.) and DIPEA (516 µl, 3.0 mmol, 3.0 eq.) in DCM (10 ml) was added. After 2.5 h the solution was filtered off and the resin successively washed with DCM, MeOH, DCM and DMF (1/1/1/3). The resin was treated twice with 20% piperidine in DMF (2 min and 20 min), washed with DMF and DCM (5/2) and dried in the vacuum to yield 760 mg of H-Ttds-trityl resin (loading based on mass increase: approximately 0.8 mmol/g). H-Ttds-trityl-resin (375 mg, 0.3 mmol, 1.0 eq.) was swollen in DMF for 30 min. Next a mixture of 2-(4,7-Bis-tert-butoxycarbonylmethyl-[1,4,7]triazonan-1-yl)-pentanedioic acid 1-tert-butyl ester (NODAGA(tBu)$_3$-OH) (245 mg, 0.45 mmol, 1.5 eq.), HATU (171 mg, 0.45 mmol, 1.5 eq.) and DIPEA (150 µl, 0.9 mmol, 3.0 eq.) was shaken for 5 min and subsequently added to the resin. After agitation for 24 h the resin was washed with DMF and DCM (5/2) and subsequently dried in the vacuum. The resin was initially treated once with a mixture of TFA, TIPS and DCM (2/5/93) and subsequently four times with a mixture of TFA, TIPS and DCM (5/5/90) for 5 min. To prevent premature loss of the NODAGA protecting groups the resulting solutions were immediately poured into aqueous buffer solution (10 ml, pH=8, 100 mM NH$_4$(CO$_3$)$_2$). The pH value of the mixture was kept above pH=7 by addition of 4N NaOH solution. DCM-buffer mixtures containing the target compound were combined (solutions resulting from 1$^{st}$ and 2$^{nd}$ treatment), the phases were separated, the aqueous phase was extracted twice with DCM and the organic phase was evaporated to dryness. The residue was redissolved in ACN/water (1/1) and lyophilized.

The residue was purified by HPLC (25 to 50% B in 30 min, Agilent PLRP-S 25×150 mm) to give the title compound as colourless oil (105 mg, 0.120 mmol, 40%). HPLC: R$_t$=5.2 min. MS: m/z=845.5 ([M+H]$^+$, calculated 846.5). C$_{41}$H$_{75}$N$_5$O$_{13}$ (MW=846.06).

B. 2-{[1-(4-{[3-({3-[(NODAGA-Ttds)-methyl-amino]-propyl}-methyl-amino)-propyl]-methyl-carbamoyl}-2-isopropyl-phenyl)-5-(2,6-dimethoxy-phenyl)-1H-pyrazole-3-carbonyl]-amino}-adamantane-2-carboxylic acid (IIIe)

2-(4,7-Bis-tert-butoxycarbonylmethyl-[1,4,7]triazonan-1-yl)-4-[3-(2-{2-[3-(3-carboxy-propionylamino)-propoxy]-ethoxy}-ethoxy)-propylcarbamoyl]-butyric acid tert-butyl ester (NODAGA(tBu)$_3$-Ttds-OH) (XXII) (65 mg, 76 mol) was dissolved in DMF (0.5 ml). 0.3 ml of that solution (containing 39 mg NODAGA(tBu)$_3$-Ttds-OH (XXII), 46 µmol, 1.3 eq.) were used to dissolve 2-({5-(2,6-Dimethoxy-phenyl)-1-[2-isopropyl-4-(methyl-{3-[methyl-(3-methyl-amino-propyl)-amino]-propyl}-carbamoyl)-phenyl]-1H-pyrazole-3-carbonyl}-amino)-adamantane-2-carboxylic acid tert-butyl ester (XIX) (32.0 mg, 35 µmol, 1 eq.). DIPEA (42 µl, 250 µmol, 7 eq.) was added to the solution to adjust the pH-value to pH=7. Then HOAt (22 mg, 162 µmol, 4.5 eq.) and DIC (19 µl, 122 µmol, 3.5 eq.) were added to the mixture which was subsequently stirred for 6 h. Then an additional amount of the initially prepared solution (50 µl containing 6.5 mg NODAGA(tBu)$_3$-Ttds-OH (XXII), 7.7 µmol, 0.2 eq.) and DIC (10 µl, 64 µmol, 1.8 eq.) was added and the mixture stirred overnight. All volatiles were removed in the vacuum, the residue dissolved with DCM and aqueous citric acid solution (10%). The organic layer was separated, dried and evaporated to dryness. The residue was treated with TFA, TIPS and water (95/2.5/2.5).

The cleavage solution was directed to HPLC purification (20 to 45% B in 30 min, Agilent PLRP-S 25×150 mm) to give the title compound (23.96 mg, 17.1 µmol, 48.8%). HPLC: $R_t$=4.8 min. MS: m/z=1402.8 ([M+H], calculated 1402.8). $C_{71}H_{107}N_{11}O_{18}$ (MW=1402.67).

Example 13

2-({5-(2,6-Dimethoxy-phenyl)-1-[2-isopropyl-4-(methyl-{3-[methyl-(3-{1-methyl-3-[4-(3-DFO-thioureido)-phenyl]-thioureido}-propyl)-amino]-propyl}-carbamoyl)-phenyl]-1H-pyrazole-3-carbonyl}-amino)-adamantane-2-carboxylic (IIIf)

was detected. (MS (m/z): 1549.4 [M−3H++Fe+H]$^+$, $C_{75}H_{107}N_{14}O_{14}S_2Fe$, $R_t$=5.3 min). This finding indicated that (IIIf) formed the Zirconium complex under LC-MS measurement conditions although being actually present in the uncomplexed state.

Example 14

Zirconium-Complex of a Compound of Formula (IIIf): Zr-(IIIf)

2-({5-(2,6-Dimethoxy-phenyl)-1-[2-isopropyl-4-(methyl-{3-[methyl-(3-{1-methyl-3-[4-(3-DFO-thioureido)-phenyl]-thioureido}-propyl)-amino]-propyl}-carbamoyl)-phenyl]-1H-pyrazole-3-carbonyl}-amino)-adamantane-2-carboxylic (IIIf) (9.85 mg, 6.58 µmol, 1.0 eq.) and (IIIf)

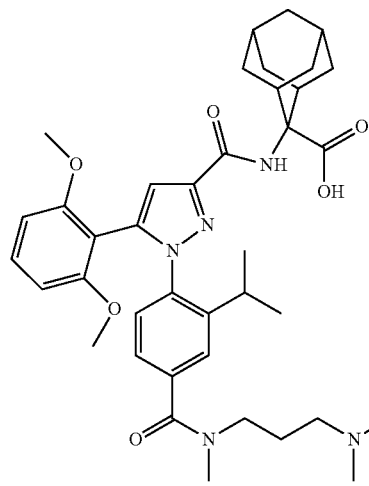
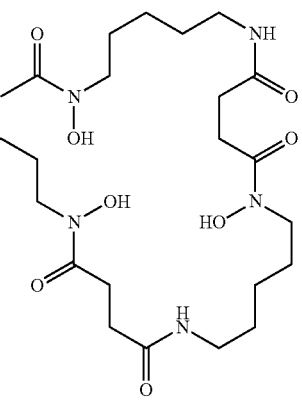

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (III) (30 mg, 40.4 µmol, 1.5 eq.) and N-[5-({3-[5-(Acetyl-hydroxy-amino)-pentylcarbamoyl]-propionyl}-hydroxy-amino)-pentyl]-N'-hydroxy-N'-{5-[3-(4-isothiocyanato-phenyl)-thioureido]-pentyl}-succinamide (20.3 mg, 26.9 µmol, 1.0 eq.) were dissolved in DMF (1.0 ml). After addition of DIPEA (9.3 µl, 53.8 µmol, 2.0 eq.) the mixture was stirred for 1 h at 50° C. Subsequently the solvent was evaporated.

The residue was purified by HPLC (15 to 45% B in 30 min, Agilent PLRP-S 25×150 mm) to give the title compound (15.6 mg, 10.4 µmol, 38.8%). HPLC: $R_t$=5.1 min. $C_{75}H_{110}N_{14}O_{14}S_2$ (MW=1495.89).

The LC-MS analytic of the compound proved to be complicated by the formation of the zirconium complex of the compound under LC-MS conditions (MS (m/z): 1581.5 [M−3H+Zr$^{4+}$]$^+$, $C_{75}H_{107}N_{14}O_{14}S_2Zr^+$, $R_t$=5.1 min). When the compound was treated with a 25 mM FeCl$_3$ solution directly before injection predominately the iron complex Zirconium(IV)acetylacetonat (12.95 mg, 26.3 µmol, 4.0 eq.) were dissolved in MeOH. After stirring for 1 h the solvent was evaporated.

The residue was directed to HPLC purification (25 to 50% B in 30 min, Agilent PLRP-S 25×150 mm) to give the title compound (2.5 mg, 1.6 µmol, 24.2%). HPLC: $R_t$=5.1 min. MS: m/z=1581.6 ([M]$^+$, calculated 1581.7). $C_{75}H_{107}N_{14}O_{14}S_2Zr^+$ (MW=1584.09).

The LC-MS analytic of the compound proved to be complicated by the formation of the zirconium complex of the not complexed compound under LC-MS conditions. When the compound was treated with a 25 mM FeCl$_3$ solution directly before injection the iron complex was detected as minor component. (MS (m/z): 1549.4 [M−3H$^+$+Fe+H]$^+$, $C_{75}H_{107}N_{14}O_{14}S_2Fe$, $R_t$=5.3 min). In contrast when the not complexed compound (IIIf) was subjected to analytical LC-MS compound with prior FeCl$_3$ treatment the iron complex appeared to be the major compound. These findings indicate that the complexation of Zirconium by (IIIf) was successful.

Example 15

2-{[5-(2,6-Dimethoxy-phenyl)-1-(4-{[3-({3-[(4-fluoro-benzoyl)-methyl-amino]-propyl}-methyl-amino)-propyl]-methyl-carbamoyl}-2-isopropyl-phenyl)-1H-pyrazole-3-carbonyl]-amino}-adamantane-2-carboxylic acid

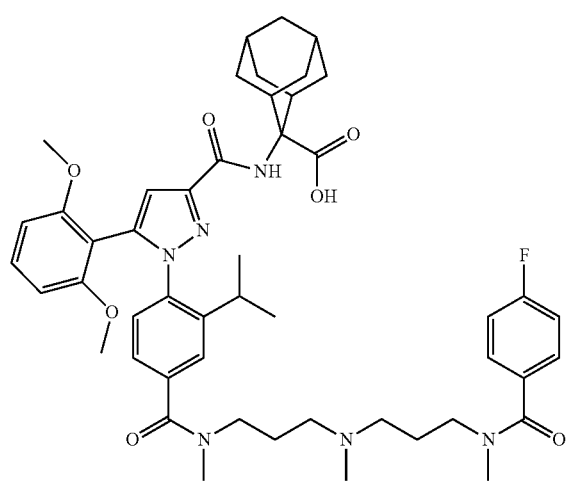

(IIIg)

2-({5-(2,6-Dimethoxy-phenyl)-1-[2-isopropyl-4-(methyl-{3-[methyl-(3-methylamino-propyl)-amino]-propyl}-carbamoyl)-phenyl]-1H-pyrazole-3-carbonyl}-amino)-adamantane-2-carboxylic acid (III) (10 mg, 13.4 µmol, 1.0 eq) were dissolved in DCM (0.4 ml). The pH-value of the solution was adjusted to pH=7 by gradual addition of DIPEA. After dropwise addition of a solution of 4-Fluorobenzoyl chloride (2.13 mg, 13.4 µmol, 1.0 eq.) in DCM (0.1 ml) the reaction mixture was stirred overnight. Then water (0.1 ml) was added, the mixture was stirred for 10 min and all volatiles were removed in the vacuum.

The oily residue was subjected to HPLC purification (25 to 55% B in 30 min, Agilent PLRP-S 25×150 mm) to give the title compound (3.24 mg, 3.75 µmol, 28.0%). HPLC: $R_f$=5.7 min. MS: m/z=865.5 ([M+H]$^+$, calculated 865.58) $C_{49}H_{61}FN_6O_7$, (MW=865.03).

Example 16

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester bound to trityl resin (XXIII)

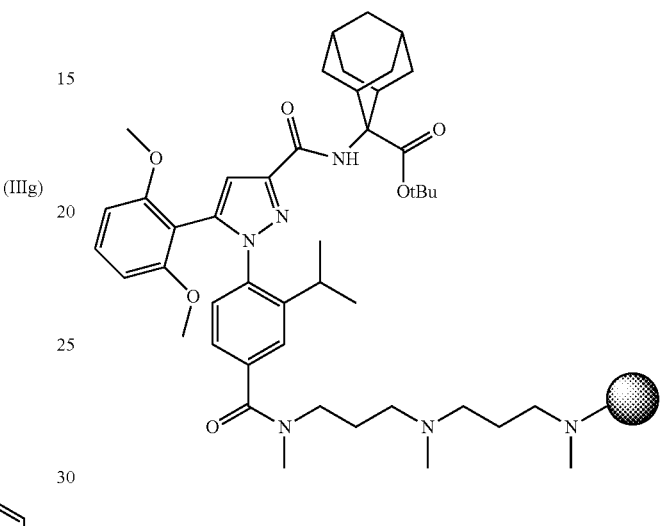

(XXIII)

Figure 8:
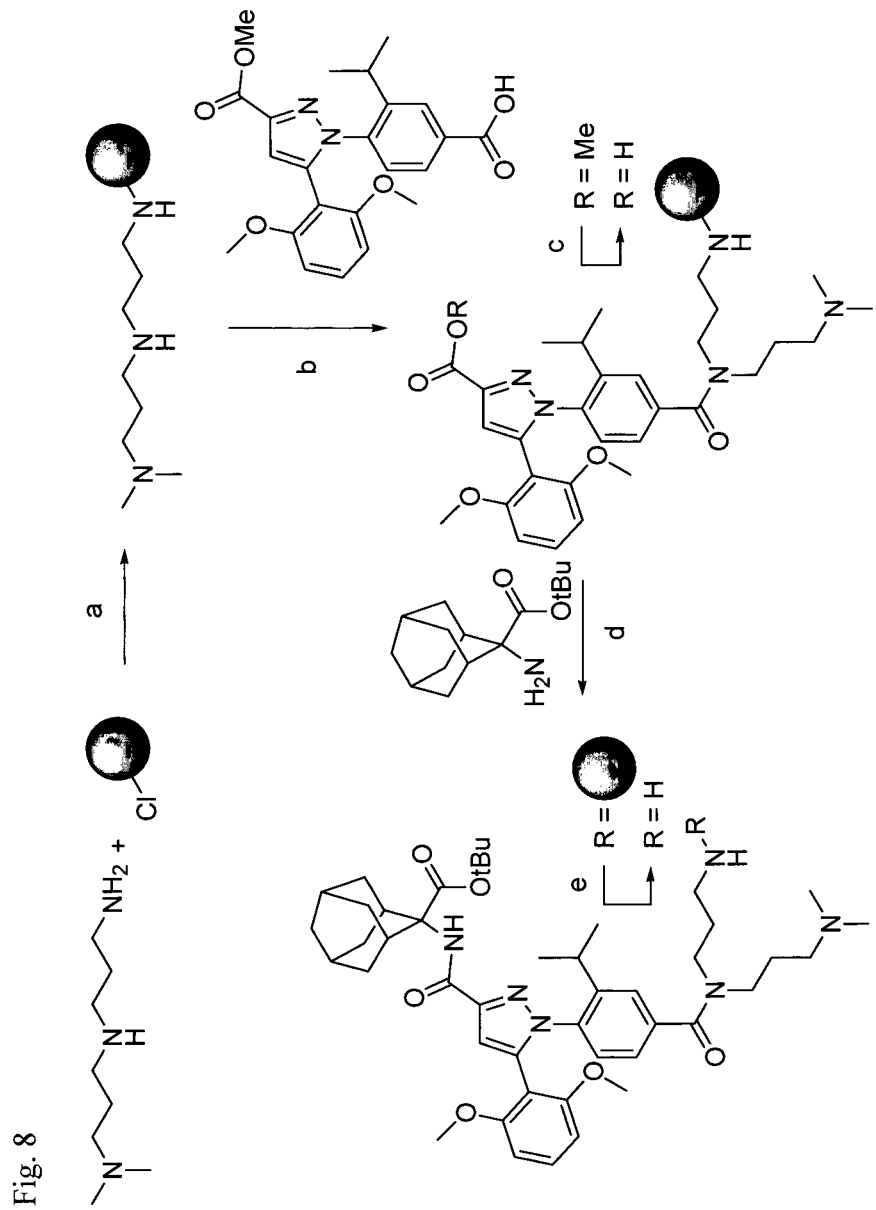
FIG. 8 shows the solid phase synthesis of derivatized resin of formula (XXIII) and tert-butyl ester of formula (XXIV)
Figure 9:
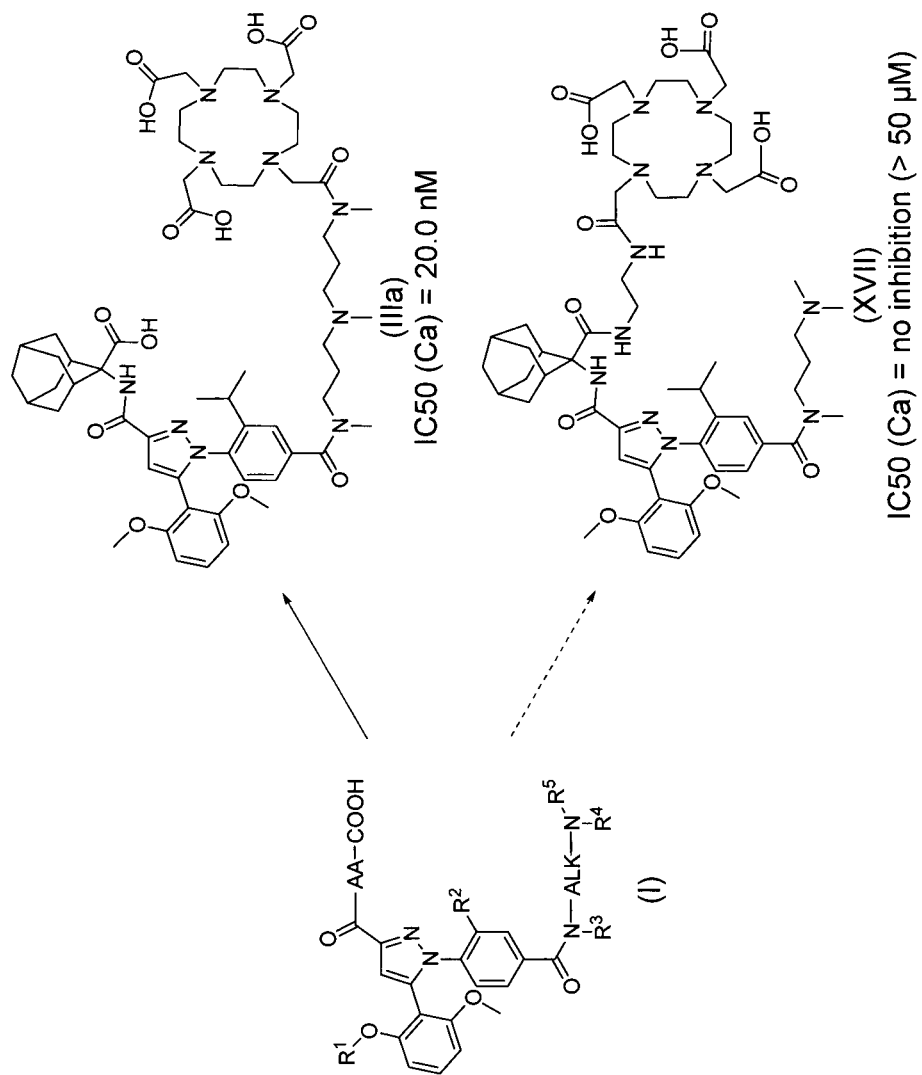
FIG. 9 is a diagram illustrating the effect of chelator positioning in a compound of formula (I) on the IC50 value in a Ca-mobilisation assay (IC50 (Ca)).

A. Loading of chlorotrityl resin with N,N-Dimethyldipropylentriamine (FIG. 8 step a)

Tritylchloride resin (initial loading 1.8 mmol/g, 334 mg g, 0.6 mmol, 1.0 eq.) was swollen in DCM for 30 min. Then N,N-Dimethyldipropylentriamine (0.54 ml, 3 mmol, 5 eq.) and DIPEA (0.2 ml, 1.2 mmol, 2.0 eq.) in DCM (4 ml) were added to the resin and the mixture shaken overnight. Afterwards the resin was washed with DMF, DCM, MeOH and diethyl ether (5/3/1) and dried in the vacuum.

B. Coupling of 1-(4-Carboxy-2-isopropyl-phenyl)-5-(2,6-dimethoxy-phenyl)-1H-pyrazole-3-carboxylic acid methyl ester (FIG. 8 step b)

N,N-Dimethyldipropylentriamine charged trityl resin (0.6 mmol, 1.0 eq.) was swollen in DMF for 30 min. 1-(4-Carboxy-2-isopropyl-phenyl)-5-(2,6-dimethoxy-phenyl)-1H-pyrazole-3-carboxylic acid methyl ester (382 mg, 0.9 mmol, 1.5 eq.), HATU (342 mg, 0.9 mmol, 1.5 eq.) and DIPEA (312 µl, 2.7 mmol, 3 eq.) were dissolved in DMF (6 ml) and mixed thoroughly for 1 min. After addition of the activated building block the resin was shaken for 3 h. The resin was washed (DMF/DCM/diethyl ether 5/3/1) and dried in the vacuum.

C. Hydrolysis of the Methylester (FIG. 8 Step c)

The resin (0.6 mmol, 1.0 eq.) described before was swollen in dioxane for 30 min and afterwards treated with dioxane (30 ml) and LiOH hydrate (504 mg, 12 mmol, 20 eq.) in water (4 ml) at 50° C. The procedure was continued at RT overnight, the resin subsequently washed with water, DCM and Et$_2$O (3/3/3) and dried in the vacuum.

D. Coupling of 2-Amino-Adamantane-2-Carboxylic Acid Tert-Butyl Ester (FIG. 8 Step d)

The resin (0.6 mmol, 1.0 eq.) described before was swollen in DMF for 1 h. Then HOAt (327 mg, 2.4 mmol, 4.0 eq.), DIC (279 µl, 1.8 mmol, 3.0 eq.) and 2-amino-adamantane-2-carboxylic acid tert-butyl ester (453 mg, 1.8 mmol, 3.0 eq.) were dissolved in a mixture of DMF and DCM (2:1) (6 ml) and added to the resin. The resin was left to shake for 60 hours after which the reaction was complete. The resin was washed with DMF and DCM (3/3) and dried in the vacuum.

Example 17

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester (XXIV), (FIG. 8 Step e)

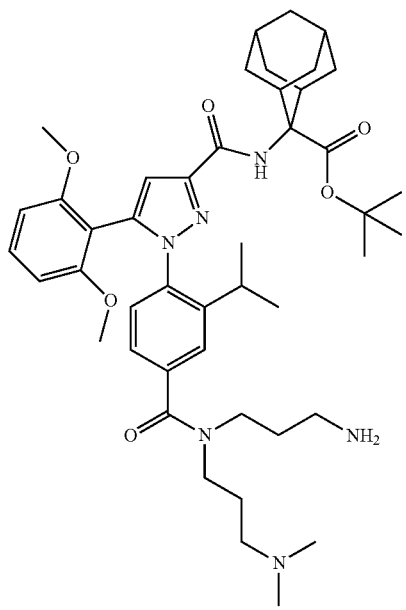

(XXIV)

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester resin (XXIII) (570 µmol, 1.0 eq.) was treated five times with a mixture of TFA, TIPS and DCM (2/5/93). To prevent premature loss of the DOTA protecting groups the resulting solutions were immediately poured into aqueous buffer solution (10 ml, pH=8, 100 mM $NH_4(CO_3)_2$). All DCM-buffer mixtures containing the target molecule were combined and the organic layer reduced to a minimum by evaporation. To the remaining aqueous solution ACN (5 ml) was added and the mixture was freeze-dried.

The residue containing the title compound (410 mg, 520 µmol, 91%) was used without further purification as crude product. HPLC: $R_t$=5.8 min. MS: m/z=785.4 ([M+H]$^+$, calculated 785.5) $C_{45}H_{64}N_6O_6$, (MW=785.03).

Example 18

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid (V)

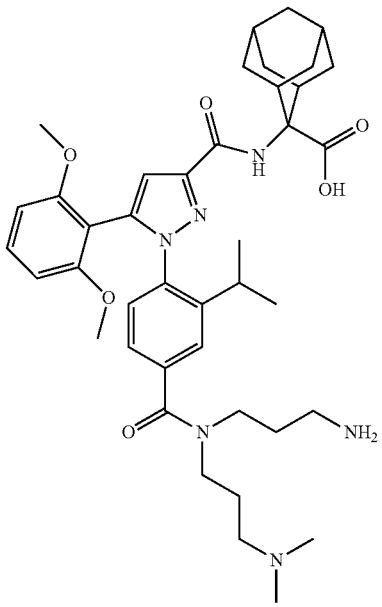

(V)

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester resin (XXIV) (41 mg, 30 µmol, 1.0 eq.) was treated with TFA, phenol, water and TIPS (36/2/2/1) (2 ml) for 2 h. The cleavage solution was poured into cyclohexan/MTBE (1/1) (20 ml).

The precipitate was subjected to HPLC purification (15 to 45% B in 30 min, Agilent PLRP-S 25×150 mm) to give the title compound (9.52 mg, 13.1 µmol, 43.5%). HPLC: $R_t$=4.8 min. MS: m/z=729.4 ([M+H]$^+$, calculated 729.4) $C_{41}H_{56}N_6O_6$, (MW=728.92).

Example 19

Synthesis of 2-{[1-{4-[(3-DOTA-amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid (Va)

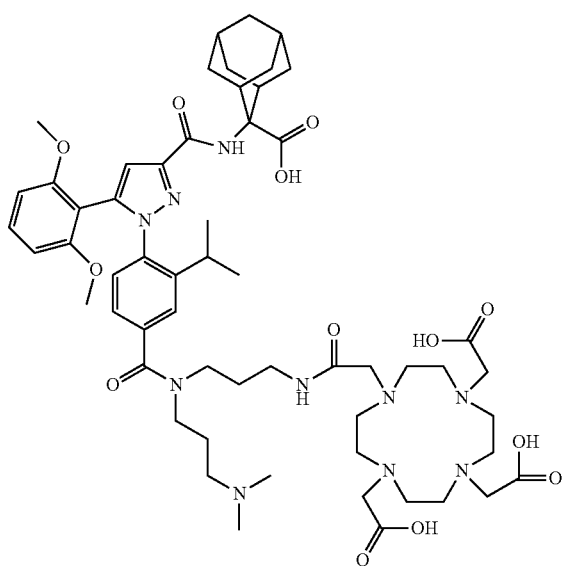

(Va)

Method A

A. 1-{4-[(3-DOTA(tBu)₃-amino-propyl)-(3-dimethylamino-propyl)-carbamoyl]-2-isopropyl-phenyl}-5-(2,6-dimethoxy-phenyl)-1H-pyrazole-3-carboxylic acid methyl ester (XIV)

DOTA(tBu)₃-OH (200 mg, 0.349 mmol, 1.0 eq.) and PyBOP (236 mg, 0.454 mmol, 1.3 eq.) were dissolved in dry DMF (5 ml). After one minute N'-(3-Dimethylamino-propyl)-propane-1,3-diamine (0.315 ml, 1.75 mmol, 5 eq.) and DIPEA (0.155 ml, 0.98 mmol, 2.6 eq.) in dry DMF (2 ml) were added. After 90 min DMF was removed under vacuum. The remaining residue was dissolved in EtOAc (30 ml) and extracted with water twice. The organic layer was dried over Na₂SO₄ and evaporated to yield 0.41 g crude material.

This crude material (0.41 g, max. 0.349 mmol) was dissolved in dry DMF (25 ml). In a separate flask 1-(4-Carboxy-2-isopropyl-phenyl)-5-(2,6-dimethoxy-phenyl)-1H-pyrazole-3-carboxylic acid methyl ester (X) (178 mg, 0.419 mmol, 1.2 eq.) [prepared as disclosed in U.S. Pat. No. 5,723,483] was dissolved in dry DMF (1.0 ml), HATU (159 mg, 0.419 mmol, 1.2 eq.) and DIPEA (0.143 ml, 0.838 mmol, 2.4 eq.) were added sequentially. The dissolved crude material from the first step, the DOTA modified diamine, was added dropwise to this HATU activated solution. After stirring for 45 min DMF was evaporated and the residual solvents were removed under high-vacuum.

The residual oil was dissolved in ACN/water/AcOH (100 μl/100 μl/1 ml) and separated in 2 batches by prep. HPLC (15 to 45% B in 30 min, Agilent PLRP-S 25×150 mm) to give the title compound (229 mg, 0.205 mmol, 59%). HPLC: $R_t$=4.7 min. MS: m/z=1120.5 ([M+H]⁺, calculated 1120.7) $C_{41}H_{56}N_6O_6$, (MW=1120.42).

B. 1-{4-[(3-DOTA(tBu)₃-amino-propyl)-(3-dimethylamino-propyl)-carbamoyl]-2-isopropyl-phenyl}-5-(2,6-dimethoxy-phenyl)-1H-pyrazole-3-carboxylic acid (XV)

Methylester of formula (XIV) (370 mg, 0.330 mmol) was dissolved in 1,4-dioxane (1.72 ml). A 1 M aqueous solution of LiOH (1.32 ml, 1.32 mmol, 4 eq.) was added dropwise. After stirring for 5 h the pH was adjusted to 4 with HOAc (0.475 ml). After addition of ACN (18 ml) and water (100 ml) the cloudy solution was freeze dried. This material was dissolved in ACN (24 ml) and water (300 ml) and applied to a solid phase extraction column (4.0 g Varian Bondesil-ENV in a 60 ml polystyrene syringe, prewashed with methanol (3×25 ml) and water (3×25 ml). The column was eluted with 80 ml of 10% ACN in water as first fraction and each of the next fractions were eluted with 80 ml of 50% ACN in water containing 0.1% TFA. After lyophilization of the fractions 4 to 6 the title compound (313 mg, 86%) was obtained. HPLC: $R_t$=4.4 min. MS: m/z=1106.5 ([M+H], calculated 1106.7) $C_{58}H_{91}N_9O_{12}$, (MW=1106.40).

C. 2-{[1-{4-[(3-(DOTA(tBu)₃-amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid (XVI)

Carboxylic acid of formula (XV) (287 mg, 0.260 mmol) was dissolved in dry NMP (3.7 ml). HATU (98.7 mg, 0.260 mmol, 1.0 eq.) was added as solid and to this mixture DIPEA (89 μl, 0.52 mmol, 2.0 eq.) was added. After stirring for 5 min this solution was transferred within 5 min to a suspension of 2-amino-adamantane-2-carboxylic acid (50.7 mg, 0.260 mmol, 1.0 eq.) and DIPEA (44 μl, 0.26 mmol, 1.0 eq.) in dry NMP (7.6 ml). After 1 h at room temperature the flask was heated with an oil bath at 65° C. bath temperature. After 6 h additional 2-amino-adamantane-2-carboxylic acid (50.7 mg, 0.260 mmol, 1.0 eq.) and DIPEA (44 μl, 0.26 mmol, 1.0 eq.) were added and heating was continued for additional 18 h. After cooling down ACN/water 1:1 was added and the solution was lyophylized. The remaining solid was separated by prep. HPLC (20 to 60% B in 30 min, Agilent PLRP-S 25×150 mm) and the title compound (40 mg, 0.031 mmol, 12% yield) was obtained. HPLC: $R_t$=5.0 min. MS: m/z=1283.7 ([M+H]⁺, calculated 1283.8) $C_{69}H_{106}N_{10}O_{13}$, (MW=1283.64).

D. 2-{[1-{4-[(3-DOTA-amino-propyl)-(3-dimethyl-amino-propyl)-carbamoyl]-2-isopropyl-phenyl}-5-(2,6-dimethoxy-phenyl)-1H-pyrazole-3-carbonyl]-amino}-adamantane-2-carboxylic acid (Va)

TFA (4.8 ml) was added to a solution of Tris-tBu-ester of formula (XVI) (40 mg, 36 µmol) and triisobutylsilane (320 µl) in dry DCM (1.3 ml). After 3.5 h at room temperature the mixture was evaporated under reduced pressure and purified by prep. HPLC (15 to 55% B in 30 min, Agilent PLRP-S 25×150 mm). This yielded the title compound (24 mg, 19 µmol, 52%) as TFA-salt. HPLC: $R_t$=4.0 min. MS: m/z=1115.6 ([M+H], calculated 1115.6) $C_{57}H_{82}N_{10}O_{13}$, (MW=1115.32).

Method B:
2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester (XXIV) (24.4 mg, 31.1 µmol, 1.0 eq.) was dissolved in DMF (0.5 ml) and DIPEA (33 µl, 187 µmol, 6 eq.) was added to the solution to adjust the pH-value to pH=7. Tri-tert-butyl-1,4,7,10-tetraazacyclodo-decane-1,4,7,10-tetraacetate (DOTA(tBu)$_3$-OH, 16.9 mg, 34.3 µmol, 1.1 eq.) was added. Then HOAt (16.9 mg, 125 µmol, 4.0 eq.) and DIC (14.5 µl, 95 µmol, 3.0 eq.) were added to the mixture which was subsequently stirred for 24 h. All volatiles were removed in the vacuum and the residue dissolved in EtOAc and water. The organic layer was dried and evaporated. The residue was stirred with TFA, phenol, water and TIPS (18/1/1/2) (0.3 ml) for 12 h.

The cleavage solution was directed to HPLC purification (20 to 45% B in 30 min, Agilent PLRP-S 25×150 mm) to give the title compound (3.7 mg, 3.3 µmol, 10.6%). HPLC: $R_t$=4.4 min. MS: m/z=1115.6 ([M+H]$^+$, calculated 1115.6) $C_{57}H_{82}N_{10}O_{13}$, (MW=1115.32).

Example 20

Indium-Complex of a Compound of Formula (Va):
In-(Va)

Complex formation was done according to the general procedure (Example 6 A) using the following reagents: Compound of formula (Va) (3.0 mg) and InCl$_3$×4 H$_2$O (2.4 mg), yielding the title compound (2.48 mg, 2.0 µmol, 75%). HPLC: $R_t$=4.3 min. MS: m/z=1227.6 ([M+H], calculated 1227.5) $C_{57}H_{79}InN_{10}O_{13}$, (MW=1227.11).

Example 21

2-{[5-(2,6-Dimethoxy-phenyl)-1-(4-{(3-dimethyl-amino-propyl)-[3-(DOTA-Ttds-amino)-propyl]-car-bamoyl}-2-isopropyl-phenyl)-1H-pyrazole-3-carbo-nyl]-amino}-adamantane-2-carboxylic (Vb)

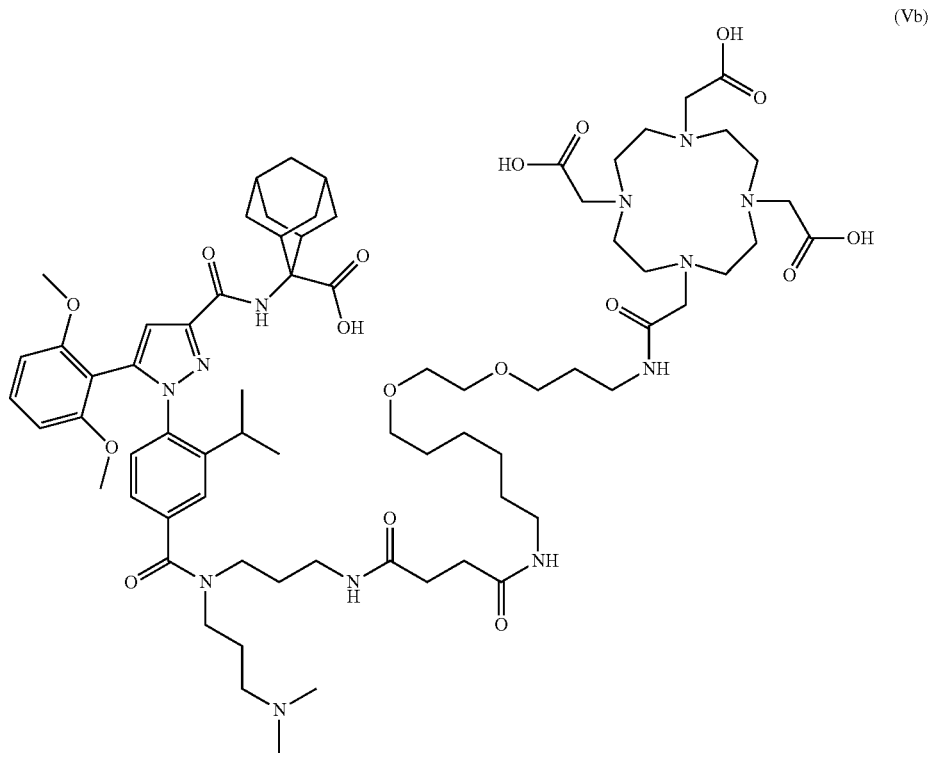 [SMILES: COc1cccc(OC)c1-c1cc(C(=O)NC2(C(=O)O)C3CC4CC(C3)CC2C4)nn1-c1ccc(C(=O)N(CCCNC(=O)CCC(=O)NCCCCCCOCCOCCCNC(=O)CN2CCN(CC(=O)O)CCN(CC(=O)O)CCN(CC(=O)O)CC2)CCCN(C)C)cc1C(C)C]

(Vb)

2-{[1-{4-[(3-Amino-propyl)-(3-dimethylamino-propyl)-carbamoyl]-2-isopropyl-phenyl}-5-(2,6-dimethoxy-phenyl)-1H-pyrazole-3-carbonyl]-amino}-adamantane-2-carboxylic acid tert-butyl ester (XXIV) (24.4 mg, 31.1 µmol, 1.0 eq.) was dissolved in DMF (0.5 ml) and DIPEA (33 µl, 187 µmol, 6 eq.) was added to the solution to adjust the pH-value to pH=7. N-{3-[2-(2-{3-[2-(4,7,10-Tris-tert-butoxycarbonylmethyl-1,4,7,10-tetraaza-cyclododec-1-yl)-acetylamino]-propoxy}-ethoxy)-ethoxy]-propyl}-succinamic acid (DOTA(tBu)$_3$-Ttds-OH) (XX) (30 mg, 34.3 µmol, 1.1 eq.) was added. Then HOAt (16.9 mg, 125 µmol, 4.0 eq.) and DIC (14.5 µl, 95 µmol, 3.0 eq.) were added to the mixture which was subsequently stirred for 24 h. All volatiles were removed in the vacuum and the residue dissolved in EtOAc and water. The organic layer was dried and evaporated. The residue was stirred with TFA, phenol, water and TIPS (18/1/1/2) (0.3 ml) for 12 h.

The cleavage solution was directed to HPLC purification (20 to 45% B in 30 min, Agilent PLRP-S 25×150 mm) to give the title compound (4.0 mg, 2.8 µmol, 9%). HPLC: R$_t$=4.4 min. MS: m/z=1417.9 ([M+H]$^+$, calculated 1417.8) C$_{71}$H$_{108}$N$_{12}$O$_{18}$, (MW=1417.69).

Example 22

Synthesis of (S)-2-{[1-{4-[(3-{[3-(DOTA-methyl-amino)-propyl]-methyl-amino}-propyl)-methyl-carbamoyl]-2-isopropyl-phenyl}-5-(2,6-dimethoxy-phenyl)-1H-pyrazole-3-carbonyl]-amino}-cyclohexyl-acetic acid (IVa)

This solid phase synthesis was performed in a standard 2 ml plastic syringe equipped with a filter in the bottom of the syringe. In this solid phase synthesis reactor L-Cyclohexylglycin loaded 2-Cl-Trt-resin (75 mg resin, 50 µmol) [Pre-pared according to a standard procedure: "Fmoc Solid Phase Peptide Synthesis" Editors W. Chan, P. White, Oxford University Press, USA, 2000] was swollen in DMF (2 ml) for 20 min. In a flask the carboxylic acid of formula (XII) (70.0 mg, 0.0625 mmol, 1.25 eq.) was dissolved in dry NMP (0.5 ml), and HATU (18.3 mg, 0.0625 mmol, 1.25 eq.) and DIPEA (16.2 µl, 0.125 mmol, 2.5 eq.) were added. After 5 min of preactivation this solution was transferred into the syringe with the resin. The syringe was closed and shaken overnight. After 15 h the reaction mixture was removed by vacuum and the resin washed with DMF (3×1.5 ml) and DCM (2×1.5 ml). After drying of the resin under reduced pressure (1 mbar) the resin was treated with a mixture of triisobutylsilane (0.1 ml) in TFA (1.9 ml) for 2 h. The cleavage solution was evaporated under reduced pressure and purified by prep. HPLC (25 to 45% B in 30 min, Agilent PLRP-S 25×150 mm). This yielded the title compound (31 mg, 28 µmol, 57%) as TFA-salt. MS (m/z): HPLC: R$_t$=4.4 min. MS: m/z=1091.6 ([M+H]$^+$, calculated 1091.6) C$_{55}$H$_{82}$N$_{10}$O$_{13}$, (MW=1091.30).

This method is generally applicable. Several other compounds were prepared in an analogous manner starting from differently preloaded trityl resins (with other amino acids or small peptides). Compound of formula (IIIa) was also prepared according to this method.

Example 23

Indium-Complex of a Compound of Formula (IVa): In-(IVa)

Complex formation was done according to the general procedure (Example 6 A) using the following reagents:

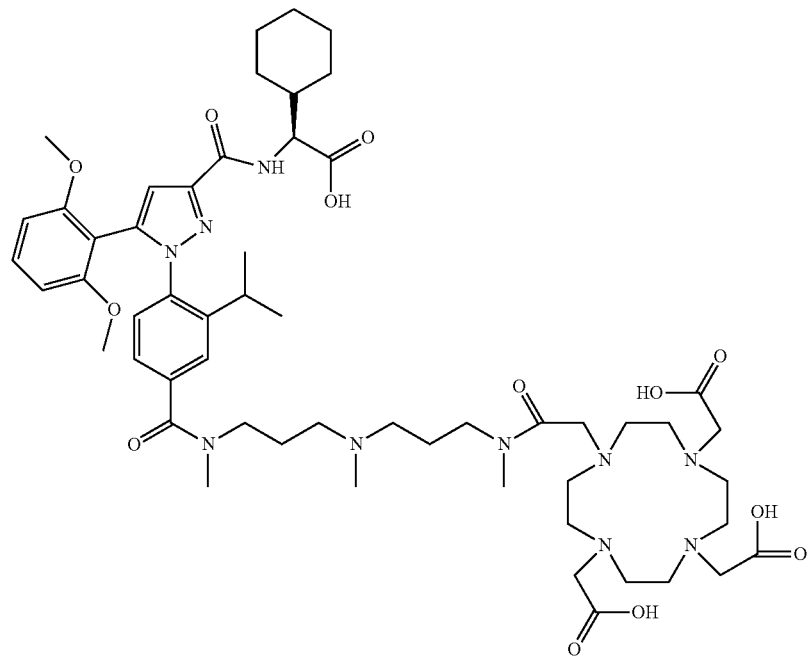

(IVa)

Compound (IVa) (3.0 mg) and InCl$_3$×4 H$_2$O (2.42 mg), yielding the title compound (2.8 mg). HPLC: R$_t$=4.4 min. MS: m/z=1203.5 ([M+H]$^+$, calculated 1203.5) C$_{55}$H$_{79}$InN$_{10}$O$_{13}$, (MW=1203.09).

Example 24

Synthesis of 5-(2,6-Dimethoxy-phenyl)-1-{4-[(3-dimethylamino-propyl)-methyl-carbamoyl]-2-isopropyl-phenyl}-1H-pyrazole-3-carboxylic acid [2-(2-DOTA-amino-ethylcarbamoyl)-adamantan-2-yl]-amide (XVII)

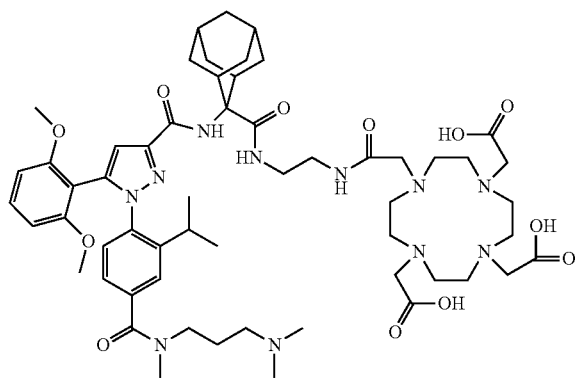

(XVII)

A. 5-(2,6-Dimethoxy-phenyl)-1-{4-[(3-dimethyl-amino-propyl)-methyl-carbamoyl]-2-isopropyl-phenyl}-1H-pyrazole-3-carboxylic acid [2-(2-DOTA (tBu$_3$)-amino-ethylcarbamoyl)-adamantan-2-yl]-amide (XVIII)

DOTA(tBu)$_3$-OH (100 mg, 0.175 mmol, 1.0 eq.) was dissolved in dry DMF (0.5 ml), HATU (66.4 mg, 0.175 mmol, 1.0 eq.) dissolved in dry DMF (0.5 ml) and Collidine (46.1 µl, 0.350 mmol, 2.0 eq.) were added. After 5 min this mixture was slowly added to a 0° C. cold solution of ethylendiamine (0.873 mmol. 5.0 eq.) in dry DMF (1.5 ml). After stirring for 19 h DMF was evaporated, the residual oil was dissolved in EtOAc (5 ml) and extracted with water (0.5 ml), sat. aq. NaHCO$_3$ (0.5 ml) and sat. aq. NaCl (0.5 ml). The organic layer was dried over Na$_2$SO$_4$, evaporated and the residue was purified by flash chromatography with DCM, DCM/methanol 20/1 and DCM/methanol 10/1 as eluents. This yielded 45 mg of monoacylated ethylendiamine. A solution of this material (18 mg, 29 mol) in dry DMF (0.2 ml) was added to a 10 min preactivated solution of SR-142948 (20 mg, 29 mol) [HATU (11.1 mg, 29 µmol) and DIPEA (10 µl, 58 µmol, 2 eq.) in dry DMF (0.4 ml)]. After 15 h monoacylated ethylendiamine (9 mg, 15 µmol, 0.5 eq.) in dry DMF (0.1 ml) was added. 5 h later the reaction mixture was heated to 60° C. for 30 min. Then the solvents were evaporated and the material purified by prep. HPLC (15 to 55% B in 30 min, Agilent PLRP-S 25×150 mm). This yielded the title compound of formula (XVIII) (15 mg, 12 µmol, 40%). HPLC: R$_t$=3.9 min. MS: m/z=1282.7 ([M+H]$^+$, calculated 1282.8) C$_{69}$H$_{107}$N$_{11}$O$_{12}$, (MW=1282.65).

B. 5-(2,6-Dimethoxy-phenyl)-1-{4-[(3-dimethyl-amino-propyl)-methyl-carbamoyl]-2-isopropyl-phenyl}-1H-pyrazole-3-carboxylic acid [2-(2-DOTA-amino-ethylcarbamoyl)-adamantan-2-yl]-amide (XVII)

TFA (1.5 ml) was added to a solution of Tris-tBu-ester of formula (XVIII) (15 mg, 11 µmol) and triisobutylsilane (100 µl) in dry DCM (0.4 ml). After 4 h at room temperature the mixture was evaporated under reduced pressure and purified by prep. HPLC (15 to 45% B in 30 min, Agilent PLRP-S 25×150 mm). This yielded the title compound (6.3 mg, 5.7 µmol, 48%) as TFA-salt. HPLC: R$_t$=3.4 min. MS: m/z=1114.6 ([M+H]$^+$, calculated 1114.6) C$_{57}$H$_{83}$N$_{11}$O$_{12}$, (MW=1114.33).

Example 25

Functional Ca$^{2+}$ Mobilisation Assay

Ca$^{2+}$ ions are usually kept at nanomolar levels in the cytosol of cells, and act in a number of signal transduction pathways as second messengers. Many GPCRs including neurotensin receptor couple to induce calcium ion signaling, and many primary cellular assays employ measurement of intracellular calcium ion concentration as a functional readout of GPCR activation. Changes in calcium ion concentration in standard assay protocols can be readily detected with fluorescent dyes that emit light when changes in intracellular Ca$^{2+}$ ion concentration occur. Given the transient nature of these responses, they are often read with instrumentation that has 'inject and read' capability. This example shows that compounds of the present invention do not have any agonistic activity on NTR1-expressing cells. Furthermore, this example shows that compounds of the present invention bind to NTR1 and inhibit the activity of an additionally present NTR1 agonist.

HT29 or NTR1-expressing HEK293 cells were trypsinized and seeded into black flat clear-bottom 96-well plates (Corning, Amsterdam, The Netherlands) at 6×10$^5$ cells per well. After 24 h incubation at 37° C. and 5% CO$_2$, cells were washed twice with wash buffer (130 mM NaCl, 5 mM KCl, 10 mM Hepes, 2 mM CaCl$_2$, 10 mM Glucose, pH 7.4) and loaded with 100 µl of Ca5 dye (Molecular Devices, Biberach, Germany) for 1 h at 37° C. and 5% CO$_2$. For agonist assays, serial dilutions of agonistic substances were added to the cells loaded with dye and the change of the fluorescent signal was recorded continually for approx. 90 s using a FlexStation II (Molecular Devices, Biberach, Germany). Addition of wash buffer served as a control. Thus, EC50 concentrations for each compound were computed and provided a measure for the potency of the substance. For antagonist assays, cells loaded with 100 µl of Ca5-dye were pre-incubated with serial dilutions of antagonistic substances for 30 min, before the EC80-concentration of agonist was added to the cells and the change of the fluorescent signal was recorded continually for approx. 90 s. Thus, IC50 concentrations were computed for each compound and provided a measure for the inhibitory activity of the compounds at the NTR1.

The results of this assay performed on some of the compounds according to the present invention are given in Table 1 together with the results of the radioligand binding assay (Example 26).

Example 26

Radioligand Binding Assay

In order to determine the binding affinity of compounds comprising a radiolabel for NTR1, a radioligand binding assay was carried out. A radioligand is a radioactive biochemical substance that is used for diagnosis or for research-oriented study of cellular receptor systems of the body. In in vivo systems it is often used to quantify the binding of a test molecule to the binding site of radioligand. The higher the affinity of the molecule, the more radioligand is displaced from the binding site. The amount of bound radioligand can be measured by scintillation counting and thereby quantified. This assay is commonly used to calculate binding constants of molecules to receptors. This example shows that compounds of the present invention bind to NTR1 with high affinity.

The NTR1 radioligand binding assay was performed by Cerep (Celle l'Evescault, France; Catalog reference 0109) according to Vita et al., *FEBS Lett.*, 1993, 317, 139-142. NTR1 was prepared from CHO cells recombinantly expressing the human receptor and incubated with 0.05 nM $^{125}$I-(Tyr$^3$-neurotensin) and serial dilutions of the test compounds. After 60 min incubation at 4° C. and washing to remove unbound neurotensin, bound radioactivity was measured by scintillation counting. The result for each test compound is expressed as IC50 concentration and provides a measure for the affinity of the test compound for NTR1.

The results of this assay performed on some of the compounds according to the present invention are given in the following Table 1.

group of formula (II) is not present at the positions defined in accordance with the present invention. On the other hand, compounds of the present invention as, for instance, the compound of formula (IIIa) where the group of formula (II) is represented by R$^4$ or R$^5$ (and also compounds as for instance the compound of formula (Va) with the group of formula (II) being represented by R$^3$) exhibit very strong NTR-1 affinities with respective Ca IC50=20 nM and RLB IC50=2.9 nM. As shown in more detail in table 1 above, also the corresponding metal complexes of, for instance, the compounds of formulae (IIIa) or (Va) exhibit similarly strong or usually even stronger NTR-1 binding affinities than their uncomplexed counterparts.

Additionally, the results shown in table 1 provide evidence that in compounds according to the present invention the NTR1-binding part thereof acts in terms of NTR1-affinity independently from the nature of the chelator as well as from the presence or absence of linkers of different structures and properties. The unmodified carboxylic acid in structures of formula (I) is an important element for high affinities toward NTR-1, but is not amenable to modifica-

TABLE 1

Results of the Ca-mobilisation assay (Ca) and the radioligand binding assay (RLB)

| Compound | Example | Linker | Acceptor | Effector | IC50 [nM] Ca | IC50 [nM] RLB |
|---|---|---|---|---|---|---|
| (III) | 4 | R$_7$ = H | — | — | 7.54 | 0.87 |
| (IIIa) | 5 | — | DOTA | — | 20.0 | 2.9 |
| In-(IIIa) | 6 B | — | DOTA | In | 5.35 | 0.76 |
| Ga-(IIIa) | 6 C | — | DOTA | Ga | 7.28 | 1.0 |
| Y-(IIIa) | 6 D | — | DOTA | Y | 6.10 | 1.2 |
| Lu-(IIIa) | 6 E | — | DOTA | Lu | 5.95 | 0.59 |
| (IIIb) | 7 | Ttds | DOTA | — | 16.6 | 5.2 |
| Lu-(IIIb) | 8 | Ttds | DOTA | Lu | 10.2 | 1.6 |
| (IIIc) | 9 | Ahx | DOTA | — | 11.8 | 5.7 |
| (IIId) | 10 | — | NODAGA | — | 14.5 | 3.7 |
| Ga-(IIId) | 11 | — | NODAGA | Ga | 7.00 | 0.94 |
| (IIIe) | 12 | Ttds | NODAGA | — | 21.4 | 4.9 |
| (IIIf) | 13 | 1,4-(-CS—NH-)$_2$-Phenyl | DFO | — | 17.5 | 3.0 |
| Zr-(IIIf) | 14 | 1,4-(-CS—NH-)$_2$-Phenyl | DFO | Zr | 21.3 | 2.1 |
| (IIIg) | 15 | — | Benzoic acid | F (para) | 14.5 | 2.3 |
| (V) | 18 | R$_7$ = H | — | — | 8.95 | 5.3 |
| (Va) | 19 | — | DOTA | — | 12.6 | 3.4 |
| In-(Va) | 20 | — | DOTA | In | 14.4 | 1.3 |
| (Vb) | 21 | Ttds | DOTA | — | 26.0 | 2.4 |
| (IVa) | 22 | — | DOTA | — | 125 | n.d. |
| In-(IVa) | 23 | — | DOTA | In | 75 | n.d. |
| (XVII) | 24 | Not applicable | Not applicable | Not applicable | No inhibition | n.d. |

All compounds with a reported IC50 are full antagonists and do not induce signals in the agonistic Ca-assay.

The implementation of a structural element like the group of formula (II), which for instance could contain a chelator such as DOTA, into the structure of formula (I), is part of the present invention. A person skilled in the art would have utilized the free carboxylic acid of the structure of formula (I) in order to attach a chelator such as DOTA. A representative example of the result of such approach is the compound of formula (XVII). The inactivity of the compound of formula (XVII) in the functional Ca-assay demonstrated that modifications at this position of the structure of formula (I) destroy NTR-1 affinity. However, this compound of formula (XVII) is not within the scope of the present invention (and is not encompassed by the structure of formula (I)) since the tions such as the attachment of an Effector moiety as evidenced by the inactivity of the compound of formula (XVII).

Example 27

Plasma Stability Assay

The plasma stability assay was performed to measure the degradation of compounds of the present invention in plasma. This is an important characteristic of a compound as compounds, with the exception of pro-drugs, which rapidly degrade in plasma generally show poor in vivo efficacy.

In order to determine the stability of compounds of formulae (IIIa) and (Va) in human and mouse plasma, a plasma stability assay was carried out. The results show that compounds of of formulae (IIIa) and (Va) are highly stable in human and mouse plasma. The stability is sufficient for the diagnostic, therapeutic and theranostic use of these compounds according to the present invention.

The plasma was spiked with a 10 mM analyte solution in dimethyl sulfoxide to a final concentration of 10 M, vortexed, and aliquotted to 50 µl samples. Two aliquots were stored at −20° C. until further treatment. Another two aliquots were incubated using an Eppendorf Thermomixer at 37° C. for 1, 4, and 24 hours. Sample clean-up was performed using a protein precipitation plate (Phenomenex Strata Impact, 64722-1-324-1) and using acetonitrile as precipitation agent. The filtrate was dried in a vacuum centrifuge and dissolved in 50 µl 25% aqueous acetonitrile solution. An aliquot of 10 µl was diluted with 90 µl 0.1% aqueous trifluoroacetic acid solution. The determination of the analyte in the clean sample solutions was performed on a Thermo TSQ Quantum Ultra triple quadrupole mass spectrometer equipped with a thermo Surveyor HPLC. The chromatographic separation was carried out on a Phenomenex Kinetex XB-C18 HPLC column (50×2 mm, 2.5 µm particle size) with gradient elution using a mixture of 0.01% trifluoroacetic acid and 0.05% formic acid in water as eluent A and methanol as eluent B (20% B to 100% in 8 min, 400 l/min, 40° C.). For mass spectrometric detection the selected reaction monitoring (SRM) was used.

Quantitation was performed by external matrix calibration using an internal standard.
LC-MS parameters:
Analyte compound of formula (IIIa)
retention time: 4.3 min
MS/MS transition: 1063.5→296.3 (48 V)
Analyte compound of formula (Va)
retention time: 4.5 min
MS/MS transition: 565.4→542.6 (19 V)

The results of this assay performed on some of the compounds according to the present invention are given in the following Table 2.

TABLE 2

Results of the plasma stability assay

| Compound | % remaining after 24 h incubation | |
|---|---|---|
| | Human plasma | Mouse plasma |
| (IIIa) | >90% | >80% |
| (Va) | >70% | >60% |

Example 28

Plasma Protein Binding Assay

A drug's efficiency may be affected by the degree to which it binds to the proteins within blood plasma. A drug in blood exists in two forms: bound and unbound. Depending on a specific drug's affinity for plasma protein, a proportion of the drug may become bound to plasma proteins, with the remainder being unbound. Notably, it is the unbound fraction which exhibits pharmacologic effects. It is also the fraction that may be metabolized and/or excreted. Protein binding can influence the drug's biological half-life in the body. The bound portion may act as a reservoir or depot from which the drug is slowly released as the unbound form.

In order to determine the binding characteristics of the compounds of the present invention as listed in the following Table to human or mouse plasma protein, respectively, a plasma protein binding assay was carried out. All compounds have a plasma protein binding that is appropriate for diagnostic, therapeutic and theranostic use of these compounds according to the present invention.

The binding of test substances to human and murine plasma proteins was tested by Cerep (Celle l'Evescault, France; Catalog reference 2194 [human] and 2223 [mouse]) according to Banker et al., *J. Pharm. Sci.,* 2003, 92, 967-974. Test compounds were incubated with human or murine plasma proteins for 4 h at 37° C. Subsequently, the fraction of compound bound to plasma proteins was determined by equilibrium dialysis and HPLC-MS/MS detection. The result for each test compound is given as the percentage bound to plasma protein.

The results of this assay performed on some of the compounds according to the present invention are given in the following Table 3.

TABLE 3

Results of the plasma protein binding assay

| Compound | % bound [human] | % bound [mouse] |
|---|---|---|
| (IIIa) | 99 | 89 |
| In-(IIIa) | 92 | 64 |
| Ga-(IIIa) | Not determined | 74 |
| Lu-(IIIa) | 95 | 67 |
| Y-(IIIa) | 96 | 76 |
| In-(Va) | 84 | 46 |
| In-(IVa) | 84 | 41 |

Example 29

Specificity Screening

The specificity screening was carried out in order to test for unspecific binding of compounds of the present invention. The specificity for NTR1 was tested using a standard battery of assays ("ExpresSProfile") comprising 55 assays on GPCRs, ion channels, and transporter proteins. This assay was performed by Cerep (Celle l'Evescault, France; Catalog reference P1).

Unspecific binding according to this specificity screening is observed if Inhibition of Control Specific Binding is above 50%. Apart from NTR1 itself, this is only observed for NK2 (66%) at a concentration that is extremely high ($10^{-5}$ M). The results show that a compound of formula (IIIa) is highly specific and well suited for diagnostic, therapeutic and theranostic use of these compounds according to the present invention.

The results of this assays performed on a compound of the present invention are presented in the following Table 4.

TABLE 4

Results of the specificity screening (ExpresSProfile) for compound of formula (IIIa).

| Assay | Catalog Reference | Test Concentration (M) | % Inhibition of Control Specific Binding | % of Control Specific Binding 1st | 2nd | Mean | SEM % Control | Reference Compound | Ki Ref (M) | nH Ref |
|---|---|---|---|---|---|---|---|---|---|---|
| A1 (h) antagonist radioligand Townsend-Nicholson et al., *J. Biol. Chem.*, 1994, 269: 2373-2376 | 0002 | 1.0E−05 | −24 | 142.9 | 104.5 | 123.7 | 19.2 | DPCPX | 6.2E−10 | 0.8 |
| A2A (h) agonist radioligand Luthin et al., *Mol. Pharmacol.*, 1995, 47, 307-313 | 0004 | 1.0E−05 | 5 | 104.2 | 85.6 | 94.9 | 9.3 | NECA | 3.5E−08 | 1.1 |
| A3 (h) agonist radioligand Salvatore et al., *Proc. Natl. Acad. Sci. U.S.A.*, 1993, 90, 10365-10369 | 0006 | 1.0E−05 | −41 | 129.0 | 153.9 | 141.4 | 12.4 | IB-MECA | 4.8E−10 | 1.0 |
| alpha 1 (non-selective) antagonist radioligand Greengrass et al., *Eur. J. Pharmacol.*, 1979, 55, 323-326 | 0008 | 1.0E−05 | −9 | 106.2 | 111.1 | 108.7 | 2.5 | prazosin | 5.8E−11 | 1.2 |
| alpha 2 (non-selective) antagonist radioligand Uhlen et al., *Pharmacol. Toxicol.*, 1991, 69, 341-350 | 0011 | 1.0E−05 | −10 | 114.4 | 106.1 | 110.3 | 4.2 | yohimbine | 3.8E−08 | 0.7 |
| beta 1 (h) agonist radioligand Levin et al., *J. Biol. Chem.*, 2002, 277, 30429-30435 | 0018 | 1.0E−05 | 2 | 89.9 | 106.1 | 98.0 | 8.1 | atenolol | 2.7E−07 | 0.9 |
| beta 2 (h) agonist radioligand Joseph et al., *Naun.-Sch. Arch. Pharm.*, 2004, 369, 525-532 | 0020 | 1.0E−05 | −2 | 107.2 | 96.5 | 101.8 | 5.4 | ICI 118551 | 1.9E−10 | 0.9 |
| AT1 (h) antagonist radioligand Le et al., *Eur. J. Pharmacol.*, 2005, 513, 35-45 | 0024 | 1.0E−05 | −18 | 118.7 | 116.8 | 117.7 | 1.0 | saralasin | 4.4E−10 | 0.6 |
| BZD (central) agonist radioligand Speth et al., *Life Sci.*, 1979, 24, 351-358 | 0028 | 1.0E−05 | −16 | 109.4 | 122.6 | 116.0 | 6.6 | diazepam | 7.5E−09 | 1.1 |
| B2 (h) agonist radioligand Pruneau et al., *Brit. J. Pharmacol.*, 1998, 125, 365-372 | 0033 | 1.0E−05 | 11 | 98.7 | 79.9 | 89.3 | 9.4 | NPC 567 | 9.9E−09 | 0.9 |
| CB1 (h) agonist radioligand Rinaldi-Carmona et al., *J. Pharmacol. Exp. Ther.*, 1996, 275, 871-878 | 0036 | 1.0E−05 | 11 | 96.0 | 82.5 | 89.3 | 6.8 | CP 55940 | 1.6E−10 | 0.8 |
| CCK1 (CCKA) (h) agonist radioligand Bignon et al., *J. Pharmacol. Exp. Ther.*, 1999, 289, 742-751 | 0039 | 1.0E−05 | −18 | 101.6 | 135.3 | 118.5 | 16.8 | CCK-8s | 6.5E−11 | 0.6 |
| D1 (h) antagonist radioligand Zhou et al., *Nature*, 1990, 347, 76-80 | 0044 | 1.0E−05 | −5 | 114.0 | 96.3 | 105.2 | 8.8 | SCH 23390 | 9.0E−11 | 0.9 |
| D2S (h) antagonist radioligand Grandy et al., *Proc. Natl. Acad. Sci. U.S.A.*, 1989, 86, 9762-9766 | 0046 | 1.0E−05 | −9 | 112.8 | 104.7 | 108.8 | 4.1 | (+)butaclamol | 2.7E−10 | 1.0 |

TABLE 4-continued

Results of the specificity screening (ExpresSProfile) for compound of formula (IIIa).

| Assay | Catalog Reference | Test Concentration (M) | % Inhibition of Control Specific Binding | % of Control Specific Binding | | | SEM % Control | Reference Compound | Ki Ref (M) | nH Ref |
|---|---|---|---|---|---|---|---|---|---|---|
| | | | | 1st | 2nd | Mean | | | | |
| ETA (h) agonist radioligand Buchan et al., *Brit. J. Pharmacol.*, 1994, 112, 1251-1257 | 0054 | 1.0E−05 | −10 | 114.3 | 105.4 | 109.8 | 4.5 | endothelin-1 | 3.6E−11 | 1.1 |
| GABA (non-selective) agonist radioligand Tsuji et al., *Antimicrob. Agents Chemother.*, 1988, 32, 190-194 | 0057 | 1.0E−05 | −6 | 101.9 | 109.9 | 105.9 | 4.0 | GABA | 1.7E−08 | 0.8 |
| GAL2 (h) agonist radioligand Bloomquist et al., *Biochem. Biophys. Res. Commun.*, 1998, 243, 474-479 | 0410 | 1.0E−05 | 1 | 96.5 | 102.1 | 99.3 | 2.8 | galanin | 2.9E−09 | 0.9 |
| CXCR2 (IL-8B) (h) agonist radioligand White et al., *J. Biol. Chem.*, 1998, 273, 10095-10098 | 0419 | 1.0E−05 | −9 | 118.7 | 99.6 | 109.1 | 9.5 | IL-8 | 5.6E−11 | 1.4 |
| CCR1 (h) agonist radioligand Neote et al., *Cell*, 1993, 72, 415-425 | 0361 | 1.0E−05 | −6 | 103.2 | 109.1 | 106.1 | 3.0 | MIP-1alpha | 4.1E−11 | 1.1 |
| H1 (h) antagonist radioligand Smit et al., *Brit. J. Pharmacol.*, 1996, 117, 1071-1080 | 0870 | 1.0E−05 | −12 | 121.2 | 103.3 | 112.3 | 9.0 | pyrilamine | 7.6E−10 | 1.1 |
| H2 (h) antagonist radioligand Leurs et al., *Brit. J. Pharmacol.*, 1994, 112, 847-854 | 1208 | 1.0E−05 | −4 | 105.9 | 101.7 | 103.8 | 2.1 | cimetidine | 4.7E−07 | 1.2 |
| MC4 (h) agonist radioligand Schioth et al., *Neuropeptides*, 1997, 31, 565-571 | 0420 | 1.0E−05 | −8 | 113.2 | 103.7 | 108.5 | 4.7 | NDP-alpha-MSH | 2.8E−10 | 0.9 |
| MT1 (ML1A) (h) agonist radioligand Witt-Enderby et al., *Mol. Pharmacol.*, 1996, 50, 166-174 | 1538 | 1.0E−05 | 1 | 102.6 | 95.9 | 99.3 | 3.3 | melatonin | 1.3E−10 | 0.9 |
| M1 (h) antagonist radioligand Dorje et al., *J. Pharmacol. Exp. Ther.*, 1991, 256, 727-733 | 0091 | 1.0E−05 | −25 | 111.0 | 138.4 | 124.7 | 13.7 | pirenzepine | 1.4E−08 | 1.2 |
| M2 (h) antagonist radioligand Dorje et al., *J. Pharmacol. Exp. Ther.*, 1991, 256, 727-733 | 0093 | 1.0E−05 | −17 | 123.7 | 110.8 | 117.2 | 6.4 | methoctramine | 7.6E−09 | 0.9 |
| M3 (h) antagonist radioligand Peralta et al., *Embo. J.*, 1987, 6, 3923-3929 | 0095 | 1.0E−05 | −23 | 122.5 | 124.5 | 123.5 | 1.0 | 4-DAMP | 2.7E−10 | 1.1 |
| NK2 (h) agonist radioligand Aharony et al., *Mol. Pharmacol.*, 1993, 44, 356-363 | 0102 | 1.0E−05 | 66 | 34.5 | 33.7 | 34.1 | 0.4 | [Nleu10]-NKA (4-10) | 2.5E−09 | 0.8 |
| NK3 (h) antagonist radioligand Sarau et al., *J. Pharmacol. Exp. Ther.*, 1997, 281, 1303-1311 | 0104 | 1.0E−05 | −1 | 102.5 | 98.5 | 100.5 | 2.0 | SB 222200 | 4.3E−09 | 0.9 |

TABLE 4-continued

Results of the specificity screening (ExpresSProfile) for compound of formula (IIIa).

| Assay | Catalog Reference | Test Concentration (M) | % Inhibition of Control Specific Binding | % of Control Specific Binding | | | SEM % Control | Reference Compound | Ki Ref (M) | nH Ref |
|---|---|---|---|---|---|---|---|---|---|---|
| | | | | 1st | 2nd | Mean | | | | |
| Y1 (h) agonist radioligand Wieland et al., *J. Pharmacol. Exp. Ther.,* 1995, 275, 143-149 | 0106 | 1.0E−05 | −34 | 127.5 | 141.4 | 134.4 | 6.9 | NPY | 5.8E−11 | 0.7 |
| Y2 (h) agonist radioligand Fuhlendorff et al., *Proc. Natl. Acad. Sci. U.S.A.,* 1990, 87, 182-186 | 0107 | 1.0E−05 | −23 | 130.5 | 116.0 | 123.2 | 7.2 | NPY | 4.4E−11 | 0.9 |
| NTS1 (NT1) (h) agonist radioligand Vita et al., *FEBS Lett.,* 1993, 317, 139-142 | 0109 | 1.0E−05 | 99 | 2.7 | −0.1 | 1.3 | 1.4 | neurotensin | 2.4E−10 | 0.8 |
| delta 2 (DOP) (h) agonist radioligand Simonin et al., *Mol. Pharmacol.,* 1994, 46, 1015-1021 | 0114 | 1.0E−05 | −6 | 106.9 | 105.2 | 106.1 | 0.8 | DPDPE | 2.0E−09 | 0.9 |
| kappa (KOP) agonist radioligand Meng et al., *Proc. Natl. Acad. Sci. U.S.A.,* 1993, 90, 9954-9958 | 1971 | 1.0E−05 | −2 | 111.0 | 92.3 | 101.6 | 9.4 | U 50488 | 4.4E−10 | 1.2 |
| mu (MOP) (h) agonist radioligand Wang et al., *FEBS Lett.,* 1994, 338, 217-222 | 0118 | 1.0E−05 | 0 | 108.3 | 92.6 | 100.5 | 7.9 | DAMGO | 4.4E−10 | 1.0 |
| NOP (ORL1) (h) agonist radioligand Ardati et al., *Mol. Pharmacol,* 1997, 51, 816-824 | 0358 | 1.0E−05 | −7 | 104.5 | 108.8 | 106.6 | 2.2 | nociceptin | 1.3E−10 | 1.2 |
| EP4 (h) agonist radioligand Abramovitz et al., *Biochem. Biophys. Acta.,* 2000, 1483, 285-293 | 0441 | 1.0E−05 | 8 | 89.2 | 95.5 | 92.3 | 3.2 | PGE2 | 2.4E−10 | 1.1 |
| 5-HT1A (h) agonist radioligand Mulheron et al., *J. Biol. Chem.,* 1994, 269, 12954-12962 | 0131 | 1.0E−05 | −29 | 129.9 | 128.6 | 129.2 | 0.6 | 8-OH-DPAT | 6.7E−10 | 1.1 |
| 5-HT1B antagonist radioligand Hoyer et al., *Eur. J. Pharmacol,* 1985, 118, 1-12 | 0132 | 1.0E−05 | −7 | 107.0 | 106.3 | 106.7 | 0.3 | serotonin | 7.3E−09 | 0.9 |
| 5-HT2A (h) antagonist radioligand Bonhaus et al., *Brit. J. Pharmacol,* 1995, 115, 622-628 | 0135 | 1.0E−05 | −2 | 100.7 | 103.0 | 101.9 | 1.2 | ketanserin | 4.4E−10 | 1.0 |
| 5-HT2B (h) agonist radioligand Choi et al., *FEBS Lett.,* 1994, 352, 393-399. | 1333 | 1.0E−05 | −22 | 118.0 | 125.1 | 121.6 | 3.5 | (±)DOI | 3.1E−09 | 1.0 |
| 5-HT3 (h) antagonist radioligand Hope et al., *Brit. J. Pharmacol.,* 1996, 118, 1237-1245 | 0411 | 1.0E−05 | −8 | 107.6 | 107.5 | 107.5 | 0.0 | MDL 72222 | 4.2E−09 | 0.8 |
| 5-HT5a (h) agonist radioligand Rees et al., *FEBS Lett.,* 1994, 355, 242-246 | 0140 | 1.0E−05 | −2 | 109.4 | 95.2 | 102.3 | 7.1 | serotonin | 1.2E−07 | 0.8 |
| 5-HT6 (h) agonist radioligand Monsma et al., *Mol. Pharmacol.,* 1993, 43, 320-327 | 0142 | 1.0E−05 | −6 | 106.5 | 105.4 | 105.9 | 0.6 | serotonin | 6.6E−08 | 0.8 |

TABLE 4-continued

Results of the specificity screening (ExpresSProfile) for compound of formula (IIIa).

| Assay | Catalog Reference | Test Concentration (M) | % Inhibition of Control Specific Binding | % of Control Specific Binding 1st | 2nd | Mean | SEM % Control | Reference Compound | Ki Ref (M) | nH Ref |
|---|---|---|---|---|---|---|---|---|---|---|
| 5-HT7 (h) agonist radioligand Shen et al., *J. Biol. Chem.*, 1993, 268, 18200-18204 | 0144 | 1.0E−05 | 2 | 96.6 | 99.7 | 98.2 | 1.6 | serotonin | 9.4E−11 | 1.2 |
| sst (non-selective) (agonist radioligand) Brown et al., *J. Biol. Chem.*, 1990, 265, 17995-18004 | 0149 | 1.0E−05 | −11 | 111.6 | 110.0 | 110.8 | 0.8 | somatostatin-14 | 1.1E−10 | 0.8 |
| VPAC1 (VIP1) (h) agonist radioligand Couvineau et al., *Biochem. J.*, 1985, 231, 139-143 | 0157 | 1.0E−05 | −6 | 103.9 | 107.3 | 105.6 | 1.7 | VIP | 1.5E−10 | 2.0 |
| V1a (h) agonist radioligand Tahara et al., *Brit. J. Pharmacol.*, 1998, 125, 1463-1470 | 0159 | 1.0E−05 | 6 | 94.1 | 93.0 | 93.5 | 0.5 | [d(CH2)51, Tyr(Me)2]-AVP | 9.1E−10 | 1.6 |
| Ca2+ channel (L, verapamil site) (phenylalkylamine) antagonist radioligand Reynolds et al., *J. Pharmacol. Exp. Ther.*, 1986, 237, 731-738 | 0163 | 1.0E−05 | 0 | 96.1 | 103.7 | 99.9 | 3.8 | D 600 | 5.9E−09 | 0.5 |
| KV channel antagonist radioligand Sorensen et al., *Mol. Pharmacol.*, 1989, 36, 689-698 | 0166 | 1.0E−05 | −4 | 104.3 | 104.2 | 104.3 | 0.0 | alpha - dendrotoxin | 2.0E−10 | 1.7 |
| SKCa channel antagonist radioligand Hugues et al., *J. Biol. Chem.*, 1982, 257, 2762-2769 | 0167 | 1.0E−05 | 4 | 97.3 | 95.2 | 96.2 | 1.1 | apamin | 8.4E−12 | 1.3 |
| Cl- channel (GABA-gated) antagonist radioligand Lewin et al., *Mol. Pharmacol*, 1989, 35, 189-194 | 0170 | 1.0E−05 | 2 | 106.5 | 89.1 | 97.8 | 8.7 | picrotoxinin | 9.3E−08 | 0.9 |
| norepinephrine transporter (h) antagonist radioligand Pacholczyk et al., *Nature*, 1991, 350, 350-354 | 0355 | 1.0E−05 | −12 | 118.9 | 105.0 | 111.9 | 7.0 | protriptyline | 3.8E−09 | 0.9 |
| dopamine transporter (h) antagonist radioligand Pristupa et al., *Mol. Pharmacol*, 1994, 45, 125-135 | 0052 | 1.0E−05 | −15 | 123.5 | 106.4 | 114.9 | 8.5 | BTCP | 3.7E−09 | 1.0 |
| 5-HT transporter (h) antagonist radioligand Tatsumi et al., *Eur. J. Pharmacol.*, 1999, 368, 277-283 | 0439 | 1.0E−05 | −13 | 102.6 | 122.8 | 112.7 | 10.1 | imipramine | 1.2E−09 | 2.1 |

Example 30

Quantitation of Receptor Binding Sites on Tissue Sections

Autoradiography allows the determination of the binding of a substance to its receptors on tissue sections. Therefore, this method was used to determine the binding of some compounds of the present invention, and the number of receptor binding sites per tissue was quantitated. Surprisingly, when comparing an agonist and antagonist of similar affinity for the receptor, the antagonist recognizes more receptor binding sites than the agonist. This underlines the particular suitability of compounds of the invention as diagnostically or therapeutically active agents.

All tissues were frozen in liquid nitrogen or dry ice immediately after surgical resection and stored at −70° C. Receptor autoradiography was performed on 20-μm-thick cryostat (HM 500, Microm) sections of the tissue samples, mounted on microscopic slides and then stored at −20° C.

for at least 3 days to improve adhesion of the tissue to the slide. Sections were first incubated with 50 mM Tris-HCl buffer pH 7.4, containing 0.02% BSA for 3 times at 5 min. For autoradiography, two compounds with similar receptor affinity were chosen and labeled with $^{177}$Lu according to the method of example 31. They were then incubated with $^{177}$Lu-(IIIa) (antagonist) or $^{177}$Lu-[NT(8-13)-Tle$^{12}$](agonist) using 8000 cpm/100 μL in 50 mM Tris-HCl buffer pH 7.4, containing 0.02% BSA, 1 mM o-Phenantrolin and 1 mM MgCl$_2$ at room temperature for 1 h. After incubation, the sections were washed 5 times in ice-cold Tris-HCl (50 mM; pH 7.4) containing 0.02% BSA and twice in ice-cold Tris-HCl without BSA. The sections were dried for 15 min under a stream of cold air and then exposed to Biomax MR (Kodak) films for 6 h-7 days (depending on the receptor density on the tumor tissue) at 4° C. For nonspecific binding, sections were incubated with 10$^{-6}$ M neurotensin. The autoradiograms were quantified using a computer-assisted image processing system.

As a result, $^{177}$Lu-(IIIa) bound 1.3 (±0.5) fold more receptors per mg of tissue compared to $^{177}$Lu-[NT(8-13)-Tle$^{12}$]. Taking into account the presence of BSA in the incubation buffer and the binding of $^{177}$Lu-(IIIa) to plasma proteins, the result should be weighted according to the free fraction of substance determined in the plasma protein binding assay (example 28). When adjusting the results for BSA-binding of $^{177}$Lu-(IIIa), $^{177}$Lu-(IIIa) bound on average 4.4-fold higher numbers of receptors than the equivalent agonist $^{177}$Lu-[NT(8-13)-Tle$^{12}$].

Example 31

$^{111}$In-Labeling of Selected Compounds

In order to serve as a diagnostically or therapeutically active agent, a compound needs to be labeled with a radioactive isotope. The labeling procedure needs to be appropriate to ensure a high radiochemical yield and purity of the radiolabeled compound of the invention. This example shows that the compounds of the present invention are appropriate for radiolabeling and can be labeled in high radiochemical yield and purity.

35 nmol of compound of formula (IIIa) were dissolved in buffer (0.4 M acetate, 0.325 M gentisic acid, pH 5) and mixed with 150 MBq of $^{111}$In (dissolved in 0.04 μM HCl). The mixture was heated to 95° C. for 30 min. After cooling, the labeling was analyzed by thin layer chromatography (TLC) and HPLC. For TLC analysis, 2 dl of the labeling solution was analysed using an ITLC SA system (Varian, 10×1 cm) in citrate buffer (0.1 M, pH 5) and Raytest Minigita. For HPLC, 10 μl of the labeling solution were analysed with an Aeris PEPTIDE 3.6 m XB-C18; 100×4.6 mm (Phenomenex). Gradient A: MeCN, 0.1% TFA, Gradient B: H$_2$O, 0.1% TFA, flow rate 0.8 ml/min; detector: NaI (Raytest), DAD 254 nm. Retention time of the labeled product: 9.5-9.9 min.

Radiochemical yield was ≥95%, radiochemical purity was ≥95%, specific activity: 4 MBq/nmol.

Labeling with $^{177}$Lu was performed in analogy to this protocol with similar yields and purity.

Example 32

Imaging and Biodistribution Studies

Radioactively labeled compounds can be detected by imaging methods such as SPECT and PET. Furthermore, the data acquired by such techniques can be confirmed by the direct measurement of radioactivity contained in the individual organs prepared from an animal injected with a radioactively labeled compound of the invention. Thus, the biodistribution of a radioactively labeled compound can be determined and analyzed. This example shows that the compounds of the present invention show a biodistribution appropriate for diagnostic imaging and therapeutic treatment of tumors.

All animal experiments were conducted in compliance with the German animal protection laws. Female CD-1 Nu/Nu mice (6- to 8-week-old, Charles River, Sulzfeld, Germany) were inoculated either with 5×10$^6$ HT-29 cells in one flank and 5×10$^6$ Capan-1 cells in the other flank, or 1×10$^7$ HEK293 cells in the shoulder region. When tumors were palpable (after 14-18 days), mice received 5-50 MBq $^{111}$In-labelled (IIIa) administered intravenously via the tail vein. Images were obtained on a NanoSPECT/CT system (BioScan Ltd., Washington, USA). Fusion of SPECT and CT data was performed with the software OsiriX Imaging Software.

For biodistribution studies, animals were sacrificed by decapitation at different time points after injection (3, 6, 12, and 24 hours post injection) and then dissected. Different organs and tissues were collected and weighed, and the radioactivity was determined by γ-counting. A minimum of three animals were used per time point. Results are expressed as a percentage of injected dose per gram of tissue (% ID/g).

The results of the imaging and biodistribution studies for selected compounds are shown in FIGS. 2-6.

The features of the present invention disclosed in the specification, the claims, the sequence listing and/or the drawings may both separately and in any combination thereof be material for realizing the invention in various forms thereof.

The invention claimed is:

1. A compound, wherein the compound is selected from the group consisting of a compound of formula (IIIa), a compound of formula (IIIb), a compound of formula (IIIc), a compound of formula (IIId), a compound of formula (IIIe), a compound of formula (IIIf), a compound of formula (IIIg), a compound of formula (IVa), a compound of formula (IVb), a compound of formula (Va) and a compound of formula (Vb), wherein the compound of formula (IIIa) is the compound of formula (IIIb) is

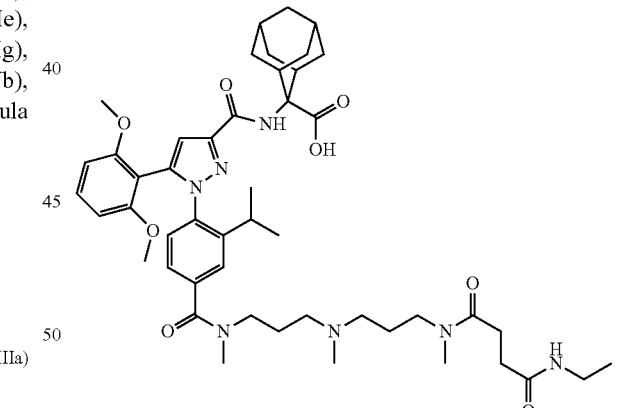

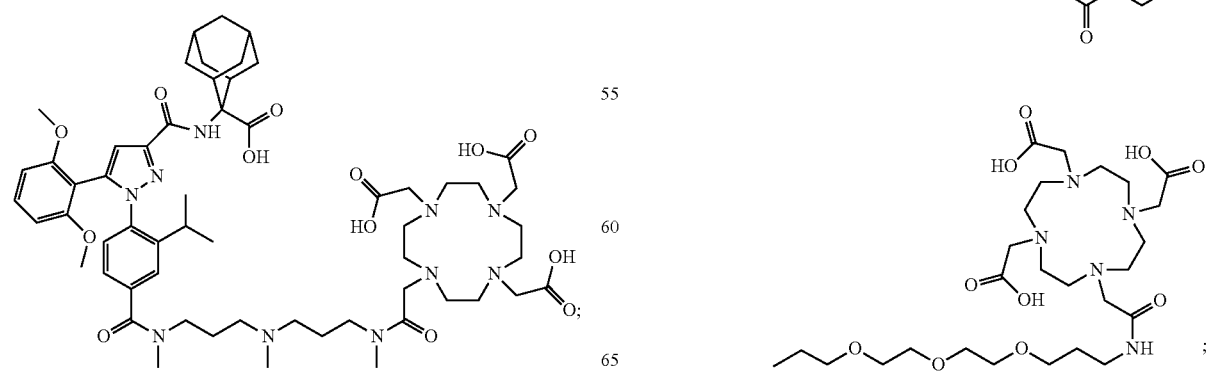

the compound of formula (IIIc) is
(IIIc)
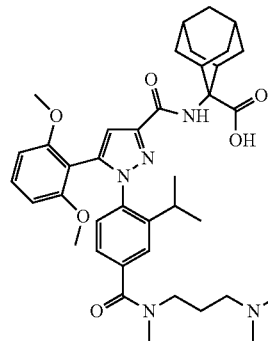 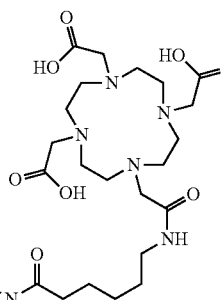
the compound of formula (IIId) is
(IIId)
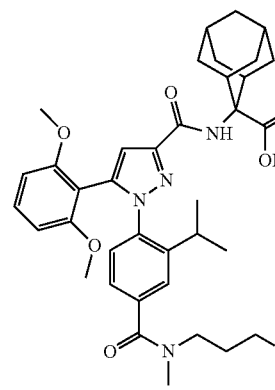 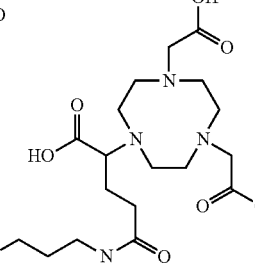
the compound of formula (IIIe) is
(IIIe)
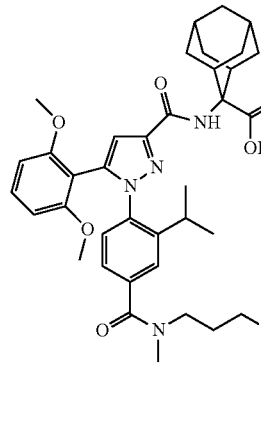
-continued
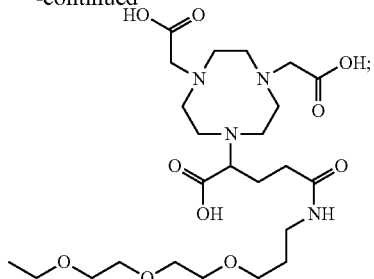
the compound of formula (IIIf) is
(IIIf)
the compound of formula (IIIg) is
(IIIg)
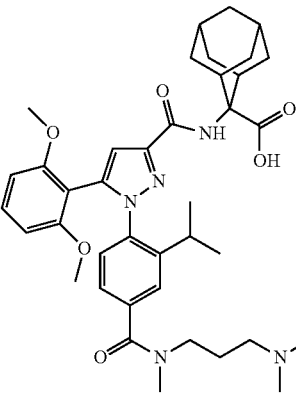

the compound of formula (IVa) is
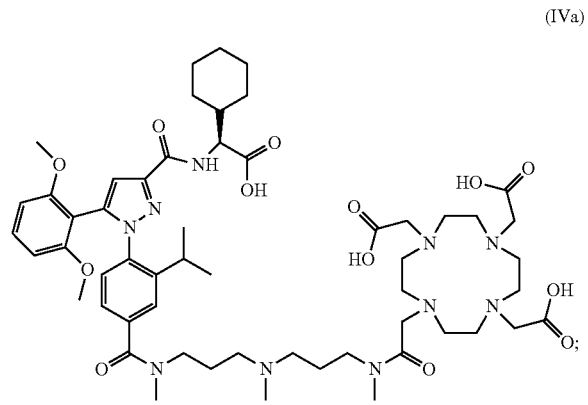 [SMILES: COc1cccc(OC)c1-c1cc(C(=O)N[C@H](C(=O)O)C2CCCCC2)nn1-c1ccc(C(=O)N(C)CCCN(C)CCCN(C)C(=O)CN2CCN(CC(=O)O)CCN(CC(=O)O)CCN(CC(=O)O)CC2)cc1C(C)C]
the compound of formula (IVb) is
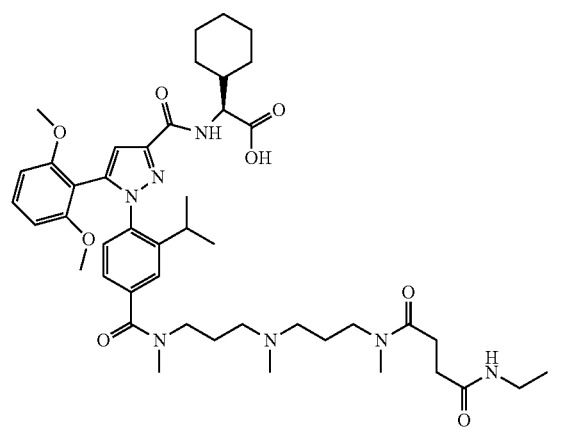
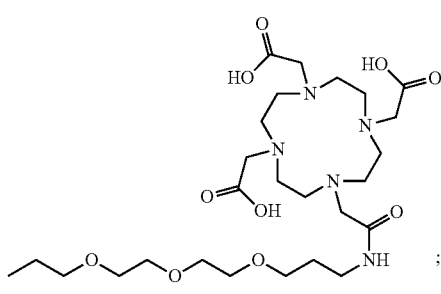
the compound of formula (Va) is
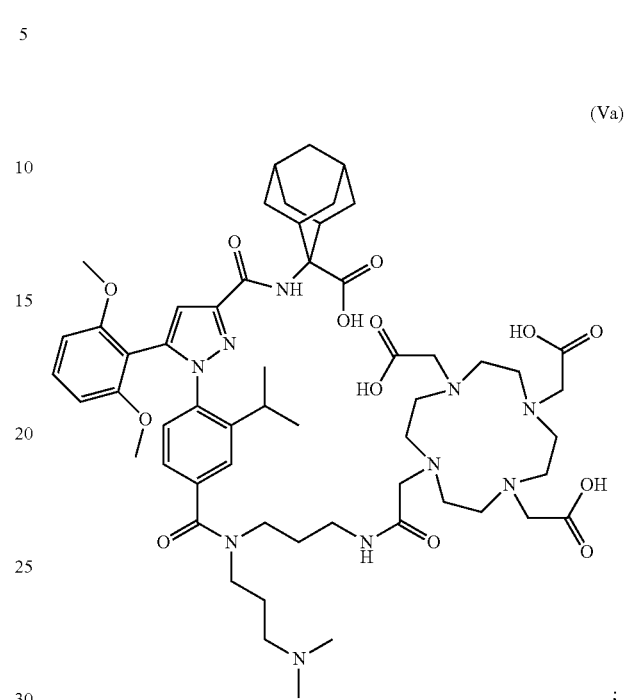
and the compound of formula (Vb) is
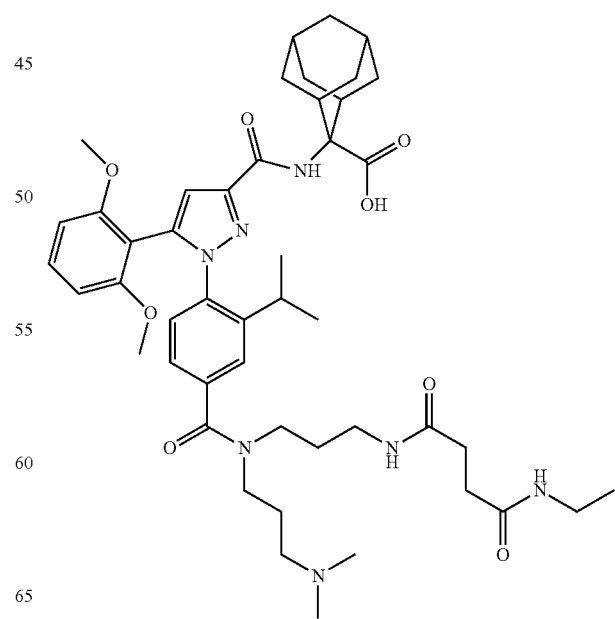

-continued

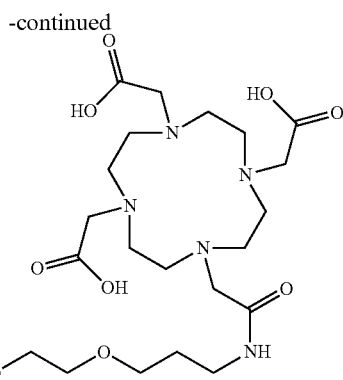

or a pharmaceutically acceptable salt, solvate, or hydrate thereof,
wherein the compound binds to neurotensin receptor 1 (NTR1) and does not cross the blood-brain barrier,
wherein the compound selected from the group consisting of formula (IIIa), (IIIb), (IIIc), (IIId), (IIIe), (IIIf), (IVa), (IVb), (Va), and (Vb) optionally further comprises a diagnostically active metal or a therapeutically active metal chelated by the chelator thereof, and
wherein $^{18}$F is optionally replacing the F atom at the fluorobenzoic acid moiety of the compound of formula (IIIg).

2. The compound of claim 1, wherein the compound is a compound of formula (IIId) and the diagnostically active metal or the therapeutically active metal is chelated by the chelator of formula (IIId).

3. The compound of claim 1, wherein the compound is a compound of formula (IIIe) and the diagnostically active metal is chelated by the chelator of formula (IIIe).

4. The compound of claim 1, wherein the compound is a compound of formula (IIIf) and the diagnostically active metal is chelated by the chelator of formula (IIIf).

5. The compound of claim 1, wherein the compound is a compound of formula (IIIg) and wherein $^{18}$F is replacing the F atom at the fluorobenzoic acid moiety of the compound of formula (IIIg).

6. A pharmaceutical composition, wherein the composition comprises a compound according to claim 1 and a pharmaceutically acceptable excipient.

7. A kit comprising a compound according to claim 1, one or more optional excipient(s) and optionally one or more device(s), whereby the device(s) is/are selected from the group consisting of a labeling device, a purification device, a handling device, a radioprotection device, an analytical device and an administration device.

8. The compound of claim 1, wherein the diagnostically active metal and the therapeutically, active metal is selected from the group consisting of $^{111}$In, $^{177}$Lu, $^{67}$Ga, $^{68}$Ga, $^{64}$Cu and $^{90}$Y.

9. The compound of claim 2, wherein the diagnostically active metal and the therapeutically active metal is selected from the group consisting of $^{67}$Ga and $^{68}$Ga.

10. The compound of claim 3, wherein the diagnostically active metal is selected from the group consisting of $^{67}$Ga and $^{68}$Ga.

11. The compound of claim 4, wherein the diagnostically active metal is $^{89}$Zr.

12. The compound of claim 1, wherein the therapeutically active metal is $^{177}$Lu.

13. The compound of claim 1, wherein the diagnostically active metal is $^{111}$In.

14. The compound of claim 1, wherein the therapeutically active metal is $^{225}$Ac.

15. The compound of claim 1, wherein the compound selected from the group consisting of formula (IIIa), (IIIb), (IIIc), (IIId), (IIIe), (IIIf), (IVa), (IVb), (Va), and (Vb) comprises a diagnostically active metal or a therapeutically active metal chelated by the chelator thereof and wherein $^{18}$F is replacing the F atom at the fluorobenzoic acid moiety of the compound of formula (IIIg).

16. A method for the diagnosis of a disease involving expression of neurotensin receptor on a cell and/or tissue, wherein the method comprises administering a diagnostically effective amount of the compound of claim 15 to a subject to be diagnosed, and imaging the compound, wherein the subject is diagnosed of suffering from the disease if the compound binds to the cell and/or the tissue.

17. A pharmaceutical composition, wherein the composition comprises a compound according to claim 15 and a pharmaceutically acceptable excipient.

18. A kit comprising a compound according to claim 15, one or more optional excipient(s) and optionally one or more device(s), whereby the device(s) is/are selected from the group consisting of, of a labeling device, a purification device, a handling device, a radioprotection device, an analytical device and an administration device.

19. A method for the diagnosis of a cancer, the method comprising administering a diagnostically effective amount of the compound of claim 15 to a subject to be diagnosed, and diagnosing the cancer in the subject.

20. A method for the treatment of a cancer, wherein the method comprises administering a therapeutically effective amount of the compound of claim 15 to a subject to be treated.

21. A compound, wherein the compound is a compound of formula (IIIa), (IIIa)

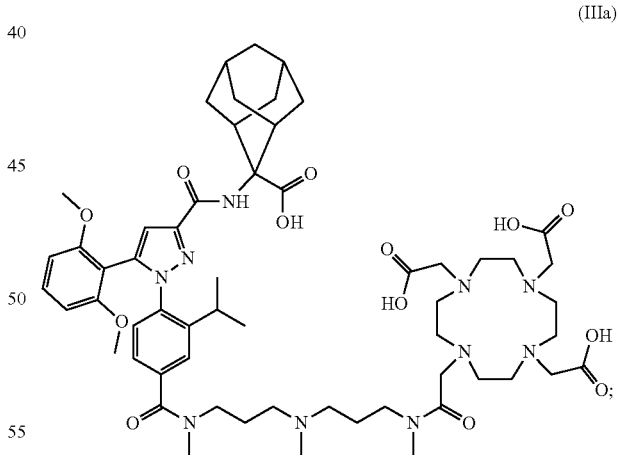

or a pharmacologically acceptable salt thereof,
wherein the compound binds to neurotensin receptor 1 (NTR1) and does not cross the blood-brain barrier; and
wherein the compound optionally further comprises a diagnostically active metal or a therapeutically active metal chelated by the chelator thereof 22. The compound of claim 21, wherein the therapeutically active metal is $^{177}$Lu.

23. The compound of claim 21, wherein the diagnostically active metal is $^{111}$In.

24. The compound of claim 21, wherein the therapeutically active metal is $^{225}$Ac.

25. A pharmaceutical composition, wherein the composition comprises the compound of claim 21 and a pharmaceutically acceptable excipient.

26. A method for the treatment of cancer, wherein the method comprises administering a therapeutically effective amount of the compound of claim 21 to a subject to be treated.

* * * * *